US012799202B2

(12) United States Patent
Ma

(10) Patent No.: US 12,799,202 B2
(45) Date of Patent: Nov. 17, 2026

(54) TUMOR-ACTIVATED ALLOREACTIVE AND XENOREACTIVE T CELLS AND THEIR USE IN IMMUNOTHERAPY AGAINST CANCER

(71) Applicant: THE NEMOURS FOUNDATION, Jacksonville, FL (US)

(72) Inventor: Zhengyu Ma, Garnet Valley, PA (US)

(73) Assignee: THE NEMOURS FOUNDATION, Jacksonville, FL (US)

( * ) Notice: Subject to any disclaimer, the term of this patent is extended or adjusted under 35 U.S.C. 154(b) by 1153 days.

(21) Appl. No.: 17/574,483

(22) Filed: Jan. 12, 2022

(65) Prior Publication Data

US 2022/0125846 A1 Apr. 28, 2022

Related U.S. Application Data

(63) Continuation-in-part of application No. PCT/US2021/040765, filed on Jul. 7, 2021.

(60) Provisional application No. 63/048,881, filed on Jul. 7, 2020.

(51) Int. Cl.

| | |
|---|---|
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C07K 16/28*** | (2006.01) |
| ***C12N 5/0783*** | (2010.01) |

(52) U.S. Cl.

CPC .......... *C07K 16/2809* (2013.01); *A61K 40/11* (2025.01); *A61K 40/31* (2025.01); *A61K 40/4205* (2025.01); *A61K 40/4211* (2025.01); *A61P 35/00* (2018.01); *C07K 14/7051* (2013.01); *C12N 5/0636* (2013.01); *A61K 2239/31* (2023.05); *A61K 2239/38* (2023.05); *A61K 2239/49* (2023.05)

(58) Field of Classification Search

None

See application file for complete search history.

(56) References Cited

U.S. PATENT DOCUMENTS

| | | | | |
|---|---|---|---|---|
| 2014/0234851 | A1 | 8/2014 | Leonard et al. | |
| 2016/0264665 | A1 | 9/2016 | Lim et al. | |
| 2017/0233474 | A1 | 8/2017 | Lim et al. | |
| 2019/0119638 | A1 | 4/2019 | Sadelain et al. | |
| 2020/0109210 | A1* | 4/2020 | Orentas | C07K 14/705 |
| 2021/0107965 | A1 | 4/2021 | Lim et al. | |
| 2023/0016034 | A1* | 1/2023 | Valamehr | A61P 35/00 |
| 2023/0381236 | A1* | 11/2023 | Kim | C07K 14/70521 |
| 2025/0243285 | A1* | 7/2025 | June | C07K 16/30 |

FOREIGN PATENT DOCUMENTS

| | | | |
|---|---|---|---|
| WO | WO-2017/193059 | A1 | 11/2017 |
| WO | WO-2018/039247 | A1 | 3/2018 |
| WO | WO-2019/199689 | A1 | 10/2019 |
| WO | WO-2020/018964 | A1 | 1/2020 |
| WO | WO-2022/011065 | A1 | 1/2022 |

OTHER PUBLICATIONS

International Search Report and Written Opinion mailed Oct. 22, 2021 in International Application No. PCT.US2021/040765.

Roybal et al., 2016, Engineering T Cells with Customized Therapeutic Response Programs Using Synthetic Notch Receptors. *Cell* 167:419-432.

Roybal et al., 2016, Precision Tumor Recognition by T Cells With Combinatorial Antigen-Sensing Circuits. *Cell* 164:770-779.

Yu et al, 2019, Next generation chimeric antigen receptor T cells: safety strategies to overcome toxicity. *Molecular Cancer* 18(1): 1-13.

Kelliher et al, 2018, NOTCH Signaling in T-Cell-Mediated Anti-Tumor Immunity and T-Cell-Based Immunotherapies. *Frontiers in Immunology* Article 1718, vol. 9: 1-6.

Choe et al, 2020, Engineering T Cells to Treat Cancer: The Convergence of Immuno-Oncology and Synthetic Biology. *Annu. Rev. Cancer Biol.* vol. 4: 121-139.

Kloss et al., 2013, Combinatorial antigen recognition with balanced signaling promotes selective tumor eradication by engineered T cells. *Nat Biotechnol.* Jan. 2013;31(1):71-5. Epub Dec. 16, 2012. Author Manuscript available PMC Jul. 11, 2017; PMCID: PMC5505184.

Kolata, Gina. A Cancer Treatment Makes Leukemia Vanish, but Creates More Mysteries. The New York Times, Feb. 2, 2022. Retrieved from the Internet: URL:www.nytimes.com/2022/02/02/health/leukemia-car-t-immunotherapy.htlm.

Weinkove et al., 2019, Selecting costimulatory domains for chimeric antigen receptors: functional and clinical considerations. *Clin Transl Immunology.* 11;8(5):e1049.

Depil et al. 2020, 'Off-the-shelf' allogeneic CAR T cells: development and challenges. *Nat Rev Drug Discov* 19, 185-199 (2020). https://doi.org/10.1038/s41573-019-0051-2.

Morsut et al., 2016, Engineering Customized Cell Sensing and Response Behaviors Using Synthetic Notch Receptors. *Cell.* 164:780-791.

Krenciute et al., 2017, Transgenic Expression of IL 15 Improves Antiglioma Activity of IL13Rα2-CAR T Cells but Results in Antigen Loss Variants. *Cancer Immunol Res.* 5(7):571-581. doi: 10.1158/2326-6066.CIR-16-0376. Epub May 26, 2017. PMID: 28550091; PMCID: PMC5746871.

(Continued)

*Primary Examiner* — Michail A Belyavskyi

(74) *Attorney, Agent, or Firm* — Faegre Drinker Biddle & Reath LLP

(57) ABSTRACT

Provided are tumor-activated alloreactive or xenoreactive T cells that are active only at the tumor sites and methods for the generation of tumor-activated alloreactive or xenoreactive T cells. Also provided are methods for using these tumor-activated alloreactive or xenoreactive T cells to treat tumors and cancers. The alloreactivity or xenoreactivity of the T cells at the tumor sites leads to the killing of tumor cells and stromal cells that express mismatched HLA molecules. The lack of activity of these T cells at non-tumor locations prevents attack on normal tissues. Further related methods and products are provided.

20 Claims, 29 Drawing Sheets

Specification includes a Sequence Listing.

(56) References Cited

OTHER PUBLICATIONS

Barnea et al. 2008, The Genetic Design of Signaling Cascades to Record Receptor Activation. Proc Natl Acad Sci USA. 105(1):64-69.
Torikai et al., 2013, Toward eliminating HLA class I expression to generate universal cells from allogeneic donors. *Blood* 122(8): 1341-1349.
Ren et al, 2017, Multiplex Genome Editing to Generate Universal CAR T Cells Resistant to PD1 Inhibition. *Clin Cancer Res* 23 (9): 2255-2266.
Gornalusse et al, 2017, HLA-E-expressing pluripotent stem cells escape allogeneic responses and lysis by NK cells. *Nat Biotechnol* 35(8):765-772. doi: 10.1038/nbt.3860. Epub May 15, 2017. Author manuscript PMID: 28504668; PMCID: PMC5548598.
Dauer et al., 2003, Mature dendritic cells derived from human monocytes within 48 hours: a novel strategy for dendritic cell differentiation from blood precursors. J Immunol. 170(8):4069-76. doi: 10.4049/jimmunol.170.8.4069. PMID: 12682236.
Cunningham et al., 2020, Recent Advances in Good Manufacturing Practice-Grade Generation of Dendritic Cells. *Transfus Med Hemother* 47:454-463. doi: 10.1159/000512451.
González et al., 2014, Tumor cell lysates as immunogenic sources for cancer vaccine design. *Hum Vaccin Immunother*. 2014;10(11):3261-9. doi: 10.4161/21645515.2014.982996. PMID: 25625929; PMCID: PMC4514089.
Gaj et al., 2016, Genome-Editing Technologies: Principles and Applications. Cold Spring Harb Perspect Biol. 8(12):a023754. doi: 10.1101/cshperspect.a023754. PMID: 27908936; PMCID: PMC5131771.
Hirakawa et al., 2020, Gene editing and CRISPR in the clinic: current and future perspectives. *Biosci Rep*. 40(4):BSR20200127. doi: 10.1042/BSR20200127. PMID: 32207531; PMCID: PMC7146048.
Choi et a., 2019, CRISPR-Cas9 disruption of PD-1 enhances activity of universal EGFRvIII CAR T cells in a preclinical model of human glioblastoma. *j. immunotherapy cancer* 7, 304 (2019). https://doi.org/10.1186/s40425-019-0806-7.
Juillerat et al., 2020, Straightforward Generation of Ultrapure Off-the-Shelf Allogeneic CAR-T Cells, Frontiers in Bioengineering and Biotechnology DOI=10.3389/fbioe.2020.00678.
Lee et al., "High-resolution donor-recipient HLAmatching contributes to the success of unrelated donor marrow transplantation," Blood, vol. 110, No. 13, 2007.
Marcus et al., "Allogeneic adoptive cell transfer therapy as a potent universal treatment for cancer," Oncotarget, vol. 2, No. 7, pp. 525-526, 2011.
Kolb et al., "Graft-versus-leukemia reactions in allogenic chimeras," Blood, vol. 103, No. 3, pp. 767-766, 2004.
Osborn et al., "Evaluation of TCR Gene Editing Achieved by TALENs, CRISPR/Cas9, and megaTAL Nucleases," The American Society of Gene and Cell Theraphy, vol. 24, No. 3, pp. 570-581, 2016.
Chmielewski et al., "CAR T Cells Releasing IL-18 Convert to T-Bethigh FoxO1low Effectors that Exhibit Augmented Activity against Advanced Solid Tumors," Cell Reports, vol. 21, pp. 3205-3219, 2017.
Kaneko et al., "Clinical implication of HLA class I expression in breast cancer," BMC Cancer, vol. 11, No. 454, 2011.
Tsukahara et al., "Prognostic significance of HLA class I expression in osteosarcoma defined by anti-pan HLA class I monoclonal antibody, EMR8-5," Cancer Sci, vol. 97, No. 12, pp. 1374-1380, 2006.
Srivastava et al., "Logic-Gated ROR1 Chimeric Antigen Receptor Expression RescuesTCell-Mediated Toxicity to Normal Tissues and Enables Selective Tumor Targeting," Cancer Cell, vol. 35, pp. 489-503, 2019.
Labrecque et al., "How Much TCR Does a T Cell Need?," Immunity, vol. 15, pp. 71-82, 2001.
Cummins et al., "Chimeric antigen receptor T-cell therapy for acute myeloid leukemia: how close to reality?," Haematologica, vol. 104, No. 7, pp. 1302-1308, 2019.
DeWolf et al., "Quantifying size and diversity of the human T cell alloresponse," Insight.jci.org, https://doi.org/10.1172/jci.insight.121256, pp. 1-17, 2018.
Suchin et al., "Quantifying the Frequency of Alloreactive T Cells in Vivo: New Answers to an Old Question," The Journal of Immunology, vol. 166, pp. 973-981, 2001.
Fennemann et al., "Attacking Tumors From All Sides: Personalized Multiplex Vaccines to Tackle Intratumor Heterogeneity," Frontiers in Immunology, vol. 10, Article 824, pp. 1-9, 2019.
International Search Report and Written Opinion for PCT/US2023/010494, dated May 17, 2023, 12 pages.

* cited by examiner

27A

27B

TUMOR-ACTIVATED ALLOREACTIVE AND XENOREACTIVE T CELLS AND THEIR USE IN IMMUNOTHERAPY AGAINST CANCER

CROSS-REFERENCE TO RELATED APPLICATION

This application is a continuation-in-part of International Application No. PCT/US2021/040765, filed Jul. 7, 2021, which claims the benefit of the filing date of U.S. Provisional Patent Application No. 63/048,881, filed Jul. 7, 2020, each of which is hereby incorporated in its entirety for all purposes.

SEQUENCE LISTING

The instant application contains a Sequence Listing which has been submitted in ASCII format via EFS-Web and is herein hereby incorporated by reference in its entirety. Said ASCII copy, created on Jan. 12, 2022, is named 045009-0053-US-SL.txt and is 24,738 bytes in size.

FIELD

The present disclosure relates to alloreactive and xenoreactive T cells and methods of limiting their alloreactivity or xenoreactivity to tumor or cancer sites in order to kill tumor cells and tumor stromal cells without significant normal tissue damage for the purpose of immunotherapy against cancer.

BACKGROUND

T cell-based Immunotherapy against cancer has made major strides in recent years. T cells engrafted with chimeric antigen receptors (CARs) demonstrated remarkable efficacy in treating B cell malignancies (1-5). FDA approval of the first CAR T cell drug for B cell lymphoma in 2017 marked a major milestone in the fight against cancer. In this approach, autologous T cells from the patient are isolated and genetically modified to express CARs that recognizes the pan-B cell marker CD19. CAR T cells infused back to the patient are able to recognize cancer cells through CAR-CD19 interaction. Signals from CARs lead to T cell activation and cytotoxicity towards cancer cells. Significant challenges remain, however, in developing safe and effective T cell-based immunotherapies for a wider range of cancers, especially for solid tumors and non-B-cell hematopoietic malignancies.

A major challenge for T cell therapy against solid tumors is the heterogeneity of tumor antigen expression. To date, the success of CAR T cell therapy is largely limited to treating B cell cancers. Due to the homogeneous expression of CD19 on all cancerous B cells, complete eradication of cancer cells can be achieved. In fact, normal B cells are eliminated as well but the lack of B cell function is easily compensated with immunoglobulin infusion. In contrast, the expression of most solid tumor antigens is much more heterogeneous in terms of the types of tissues they are expressed in and expression levels among tumor cells. Many tumor antigens can be highly expressed in tumors but may also be expressed in certain normal tissues at lower levels than found in tumors (6). Moreover, tumor antigen expression within tumors is rarely uniform, with only a certain percentage of tumor cells expressing any given type of tumor antigen (7-10). Progresses have been made in minimizing "on-target, off-tumor" targeting of normal tissues by designing CARs that mediate T cell responses only to cells expressing tumor antigens at high levels (11) or cells expressing multiple tumor antigens (12-14). Heterogeneity in tumor antigen expression among tumor cells, however, remains a major roadblock. The challenge was highlighted by a recent clinical study targeting EGFRvIII (epithelial growth factor receptor variant III) for glioblastoma (10). CAR T cells infiltrated the tumors, killed EGFRvIII-positive tumor cells but failed to halt glioblastoma progression, most likely due to the expansion of EGFRvIII-negative tumor cells under the selection pressure from the CAR T cells. Similar results were observed in a study targeting IL13Rα2 for glioblastoma in animal models (15).

The challenge of target antigen heterogeneity also exists for non-B cell blood cancers. The lack of cancer-specific antigen has hampered the efforts to develop CAR T therapy for acute myeloid leukemia (AML) (16). Most targets identified today, such as CD33 and CD123, are also expressed on normal myeloid cells and hematopoietic stem cells (17, 18). Targeting these antigens therefore often requires rescue hematopoietic stem cell transplantation. Heterogeneous expression of target antigens among cancer cells is a main contributor to relapse post CAR T cell therapy. The expression of B-cell maturation antigen (BCMA) in myeloma biopsies, for example, varies in terms of both percentage and level of expression (19).

Therefore, an urgent need remains for effective strategies that can overcome antigen-negative immune escape by broadening the target to include tumor antigen-negative tumor cells and stromal cells that support tumor growth. Approaches that target alternative antigens are also needed to overcome the barriers for non-B cell hematopoietic malignancies. This disclosure addresses these needs.

SUMMARY

The present disclosure relates to alloreactive and xenoreactive T cells and methods of limiting their alloreactivity or xenoreactivity to tumor sites or sites enriched in cancer cells in order to kill tumor cells, tumor stromal cells, and cancer cells without significant damage to normal tissues outside of the sites for the purpose of immunotherapy against cancer.

The present disclosure provides a tumor-activated alloreactive or xenoreactive T cell. The T cell can be used to kill tumor cells, tumor stromal cells, and cancer cells. Advantageously, the T cell should not cause significant normal tissue damage. Thus, a method of treating a patient having a malignancy, in particular, a solid tumor and a non-B cell hematopoietic malignancy, is also provided. A method of preparing the tumor-activated T cell and related kits are also provided.

The therapeutic methods and compositions used in these methods as described herein can be alternatively considered as a use of genetically-modified tumor-activated alloreactive or xenoreactive T cells for use in treating cancer in a patient in therapeutic need thereof, or for use in the preparation of a medicament for treating cancer. The use of the disclosed genetically-modified tumor-activated T cell can be applied to any of the methods and combinations described above and infra.

Provided is a genetically modified T cell comprising: (i) genetic disruption of expression of at least one endogenous gene encoding a molecule necessary for TCR signaling and T cell activation, (ii) an exogenous nucleotide sequence encoding a tumor-sensing receptor that releases or activates a transcription activator in response to direct or indirect binding to molecules enriched on tumor cells, in the tumor microenvironment or in tissues with blood cancer cell accumulation, and (iii) an exogenous nucleotide sequence comprising an expression cassette that expresses a copy of the disrupted endogenous gene of (i) in response to the released or activated transcription activator of (ii).

In some aspects, the at least one disrupted endogenous gene encoding a molecule necessary for TCR signaling and T cell activation encodes a transmembrane protein selected from, for example, one or more of CD3ε, CD3ζ, CD3γ, CD3δ, CD4, CD8α, CD8β, LAT, TRIM, CD45, CD28, LFA-1, CD2, CD54, CD52, CD148, and CD58. In certain embodiments, the endogenous gene disrupted is selected from CD3ε, CD3ζ, CD3γ, and CD3δ. In an embodiment, the endogenous gene disrupted is CD3ε. In some aspects, the at least one disrupted endogenous gene encoding a molecule necessary for TCR signaling and T cell activation encodes an intracellular signaling molecule chosen from Lck, Zap70, calcineurin, PI3K, Fyn, PLCγ, SLP76, PKCθ, AKT, and PDK1.

In aspects of the genetically modified T cell, the tumor-sensing receptor comprises (i) an extracellular domain that binds directly or indirectly to a target molecule enriched on or in at least one of tumor cells, tumor microenvironment, and tissues with blood cancer cell accumulation; and (ii) an intracellular domain that activates or releases a transcription activator in response to extracellular domain binding to the target molecule. The tumor-sensing receptor can be a Synthetic Notch (SynNotch) receptor, a Modular Extracellular Sensor Architecture (MESA) receptor, a Tango receptor, or a chimeric antigen receptor (CAR).

In some aspects, the target molecule is enriched on tumor cells and/or in the tumor microenvironment and is chosen from, for example. one or more of CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, FAP, fibronectin extra domain-B, folate receptor 1, GD2, GD3 ganglioside, glycoprotein 75, GPNMB, HGF, human scatter factor receptor kinase, IGF-1 receptor, IGF-I, IgGl, Ll-CAM, IL-13, IL-6, insulin-like growth factor I receptor, integrin αvβ3, MORAb-009, MS4A1, MUC1, mucin CanAg, N-glycolylneuraminic acid, NPC-IC, PDGF-Ra, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, mesothelin, NKG2D, CD147, NKR2, B7H3, and vimentin. In certain embodiments, the target molecule is selected from Her2/neu, EGFRvIII, CD19, IL-13RR-a2, mesothelin, MUCI, EpCAM, GD2 and CEA. In certain embodiments, target molecule is selected from Her2/neu, EGFRvIII, CD19, IL-13RR-a2, mesothelin, and MUCI. In certain embodiments, the target molecule is selected from Her2/neu, EGFRvIII, and CD19. In an embodiment, the target molecule is Her2/neu.

In some aspects, the target molecule is enriched in a tissue with blood cancer cell accumulation, and wherein the tissue is lymphoid and/or bone marrow tissue. In certain embodiments, the target molecule can be chosen from CD45, CD19, CD20, CD4, CD8, CD2, CCR4, CD58, CD28, CD23, CD69, CD25, CD33, CD123 and CCL-1.

In some aspects, the extracellular domain of the tumor-sensing receptor is a single chain variable fragment (scFv), a Fab fragment, a designed ankyrin repeat protein (DARPin), a nanobody, a TCR, a Fc receptor, a growth factor receptor, a chemokine receptor, or a hormone receptor.

In some aspects, the tumor-sensing receptor is a chimeric antigen receptor, wherein a downstream transcription factor is activated through signaling pathways activated in response to extracellular domain binding to the target molecule.

In certain embodiments, the expression cassette encoding the copy of the disrupted endogenous gene comprises a transcription control element driving expression of the copy of the disrupted endogenous gene is bound by a transcription activator selected from the group consisting of Gal4-VP64, Notch, tet transactivator, NFAT, AP-1, NFκB/Rel, NR4A1 (Nur77), T-Bet, IRF4, STATs and eomesodermin (Eomes). In certain embodiments, the expression cassette is selected from Gal4-CD3-PGK-BFP, NR4A-CD3-PKG-BFP, and NFAT-CD3-PKG-BFP. In certain embodiments, the tumor sensing receptor and expression cassette are selected from SynNotch and Gal4-CD3-PGK-BFP, CAR and NR4A-CD3-PKG-BFP, and CAR and NFAT-CD3-PKG-BFP.

In certain aspects, the sample of T cells is from a donor individual, and wherein the donor individual has at least one HLA allele mismatch relative to an intended recipient and the at least one HLA allele mismatch is located in a locus selected from the group consisting of: HLA-A, HLA-B, HLA-C, HLA-DRB1, HLA-DQA1, HLA-DQB1, HLA-DPA1 and HLA-DPB1, thereby producing tumor-activated alloreactive T cells. In certain embodiments, the at least one HLA allele mismatch is located in a locus selected from the group consisting of: HLA-A, HLA-B, HLA-C, and HLA-DRB1. In certain embodiments, the HLA allele mismatch comprises four alleles of, HLA-A, HLA-B, HLA-C, and HLA-DRB1, six alleles of, HLA-A, HLA-B, HLA-C, and HLA-DRB1 or all eight alleles of HLA-A, HLA-B, HLA-C, and HLA-DRB1. In an embodiment, the HLA allele mismatch comprises all eight alleles of HLA-A, HLA-B, HLA-C, and HLA-DRB1.

In certain embodiments, the endogenous gene disrupted is CD3ε, the target molecule is selected from Her2/neu, EGFRvIII, and CD19, and the tumor sensing receptor is SynNotch or CAR. In certain embodiments, the endogenous gene disrupted is CD3ε, the target molecule is selected from Her2/neu, EGFRvIII, and CD19, the tumor sensing receptor is SynNotch, and the expression cassette is Gal4-CD3-PGK-BFP. In an embodiment, the endogenous gene disrupted is CD3ε, the target molecule is Her2/neu, the tumor sensing receptor is SynNotch, and the expression cassette is Gal4-CD3-PGK-BFP. In an embodiment, the endogenous gene disrupted is CD3ε, the target molecule is Her2/neu, the tumor sensing receptor is CAR, and the expression cassette is NFAT-CD3-PGK-BFP. In an embodiment, the endogenous gene disrupted is CD3ε, the target molecule is Her2/neu, the tumor sensing receptor is CAR, and the expression cassette is NFAT-CD3-PGK-BFP. In an embodiment, the endogenous gene disrupted is CD3ε, the target molecule is CD19, the tumor sensing receptor is SynNotch, and the expression cassette is Gal4-CD3-PGK-BFP.

Further provided is a method for producing tumor-activated alloreactive or xenoreactive T cells. The method comprises a) selecting a sample of T cells from a donor individual, or from a donor animal; b) optionally stimulating the sample of T cells to proliferate; c) abrogating the expression or function of at least one molecule necessary for TCR signaling and T cell activation in the T cells to render the T cells activation-incompetent; and d) modifying the T cells to (i) express a recombinant receptor that specifically binds to a target molecule enriched on or in at least one of tumor cells, tumor microenvironment, and a tissue with blood cancer cell accumulation, wherein binding of the recombinant receptor with the target molecule releases or activates a transcription activator; and (ii) introduce an expression cassette that enables the transcription activator in (i) to drive the expression of the molecule abrogated in c), thereby restores the expression or function of the abrogated molecule, and thereby restores the ability of the T cells to activate through antigen recognition by TCR, thereby producing tumor-activated alloreactive or xenoreactive T cells. In the method, step d) is carried out before step c), step c) is carried out before step d), or steps c) and d) are performed at the same time.

In certain aspects of the method, the sample of T cells is from a donor individual, and wherein the donor individual has at least one HLA allele mismatch relative to an intended recipient and the at least one HLA allele mismatch is located in a locus selected from the group consisting of: HLA-A, HLA-B, HLA-C, HLA-DRB1, HLA-DQA1, HLA-DQB1, HLA-DPA1 and HLA-DPB1, thereby producing tumor-activated alloreactive T cells. In certain embodiments, the at least one HLA allele mismatch is located in a locus selected from the group consisting of: HLA-A, HLA-B, HLA-C, and HLA-DRB1. In certain embodiments, the HLA allele mismatch comprises four alleles of, HLA-A, HLA-B, HLA-C, and HLA-DRB1, six alleles of, HLA-A, HLA-B, HLA-C, and HLA-DRB1 or all eight alleles of HLA-A, HLA-B, HLA-C, and HLA-DRB1. In an embodiment, the HLA allele mismatch comprises all eight alleles of HLA-A, HLA-B, HLA-C, and HLA-DRB1.

In certain aspects of the method, step b) comprises: (i) co-culturing donor T cells with cells from an intended recipient; (ii) co-culturing donor T cells with cells from a second donor that has at least one HLA allele matched with the intended recipient, and (ii) is mismatched with the T cell donor; (iii) co-culturing donor T cells with a cell line expressing a least one HLA allele of the intended recipient; (iv) co-culturing donor T cells with an artificial surface coated with at least one protein encoded by at least one HLA allele of the intended recipient.

In certain embodiments of the method, the cells used to stimulate T cells in step b) comprise: (i) tumor cells isolated from the patient; (ii) PMBCs isolated from the patient; and/or (iii) mature monocyte-derived dendritic cells (MoDCs) generated monocytes isolated from PBMCs of the patient. In an embodiment, the MoDCs are pulsed with the lysate of tumor cells isolated from the patient or pulsed with the lysate of a tumor cell line derived from a tumor of the same type from a different individual.

In certain embodiments of making the T cells, the at least one molecule necessary for TCR signaling and T cell activation is a cell surface molecule chosen from CD3ε, CD3ζ, CD3γ, CD3δ, CD4, CD8α, CD8β, LAT, TRIM, CD45, CD28, LFA-1, CD2, CD54, CD52, CD148, and CD58, or an intracellular signaling molecule chosen from Lck, Zap70, calcineurin, PI3K, Fyn, PLCγ, NFAT, SLP76, PKCθ, NFκB, AKT, and PDK1. In certain embodiments, the endogenous gene disrupted is selected from CD3ε, CD3ζ, CD3γ, and CD3δ. In an embodiment, the endogenous gene disrupted is CD3ε.

In In certain embodiments of the method, the molecule necessary for TCR signaling and T cell activation is disrupted in step b) using a method comprising (i) CRISPR-Cas; (ii) transcription activator-like effector nuclease (TALEN), (iii) megaTALS, (iv) a zinc-finger nuclease; and/or (v) homing endonuclease.

In certain aspects of the method, step d) comprises introducing a nucleic acid encoding a tumor-sensing receptor into T cells, wherein the tumor-sensing receptor comprises (i) an extracellular domain that binds directly or indirectly to a target molecule enriched on or in at least one of tumor cells, tumor microenvironment, and tissues with blood cancer cell accumulation; and (ii) an intracellular domain that activates or releases a transcription activator in response to extracellular domain binding to the target molecule.

In certain aspects of the method, step d) comprises introducing a nucleic acid encoding an expression cassette into T cells, wherein the expression cassette comprises (i) a transcription control element (TCE) that can be bound by the transcription activator activated or released by the tumor sensing receptor; and (ii) a DNA sequence that encodes a copy of the gene disrupted in step c), thereby enables the expression of the disrupted gene in response to tumor sensing receptor binding to target molecule enriched on or in at least one of tumor cells, tumor microenvironment, and tissues with cancer cell accumulation. The DNA sequence that encodes a copy of the gene disrupted in step c) contains one or more silent mutations that do not alter the protein sequence that the DNA encodes but render it resistant to the method used to disrupt the endogenous gene.

In certain embodiments of the method, the DNA sequences encoding the tumor-sensing receptor and the expression cassette are introduced to T cells in step d) using a method comprising (i) retroviral vectors; (ii) lentiviral vectors; and/or (iii) transposon vectors such as Sleeping Beauty (Addgene) and piggyBac (VectorBuilder).

In certain embodiments of making the T cells. the target molecule is enriched on tumor cells and/or in the tumor microenvironment and can be chosen, for example, from CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, FAP, fibronectin extra domain-B, folate receptor 1, GD2, GD3 ganglioside, glycoprotein 75, GPNMB, HGF, human scatter factor receptor kinase, IGF-1 receptor, IGF-I, IgGl, Ll-CAM, IL-13, IL-6, insulin-like growth factor I receptor, integrin αvβ3, MORAb-009, MS4A1, MUC1, mucin CanAg, N-glycolylneuraminic acid, NPC-IC, PDGF-Ra, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, mesothelin, NKG2D, CD147, NKR2, B7H3, and vimentin, or wherein the target molecule is enriched in a tissue with blood cancer cell accumulation, wherein the tissue is lymphoid and/or bone marrow tissue, and wherein the target molecule is chosen from CD45, CD19, CD20, CD4, CD8, CD2, CCR4, CD58, CD28, CD23, CD69, CD25, CD33, CD123 and CCL-1. In certain embodiments, the target molecule is selected from Her2/neu, EGFRvIII, CD19, IL-13RR-a2, mesothelin, MUCI, EpCAM, GD2 and CEA. In certain embodiments, the target molecule is selected from Her2/neu, EGFRvIII, CD19, IL-13RR-a2, mesothelin, and MUCI. In certain embodiments, the target molecule is selected from Her2/neu, EGFRvIII, and CD19. In an embodiment, the target molecule is Her2/neu.

In certain embodiments, the expression cassette encoding the copy of the disrupted endogenous gene comprises a transcription control element driving expression of the copy of the disrupted endogenous gene is bound by a transcription activator selected from the group consisting of Gal4-VP64, Notch, tet transactivator, NFAT, AP-1, NFκB/Rel, NR4A1 (Nur77), T-Bet, IRF4, STATs and eomesodermin (Eomes). In certain embodiments, the expression cassette is selected from Gal4-CD3-PGK-BFP, NR4A-CD3-PKG-BFP, and NFAT-CD3-PKG-BFP. In certain embodiments, the tumor sensing receptor and expression cassette are selected from SynNotch and Gal4-CD3-PGK-BFP, CAR and NR4A-CD3-PKG-BFP, and CAR and NFAT-CD3-PKG-BFP.

In certain embodiments, the endogenous gene disrupted is CD3ε, the target molecule is selected from Her2/neu, EGFRvIII, and CD19, and the tumor sensing receptor is SynNotch. In certain embodiments, the endogenous gene disrupted is CD3ε, the target molecule is selected from Her2/neu, EGFRvIII, and CD19, the tumor sensing receptor is SynNotch, and the expression cassette is Gal4-CD3-PGK-BFP. In an embodiment, the endogenous gene disrupted is CD3ε, the target molecule is Her2/neu, the tumor sensing receptor is SynNotch, and the expression cassette is Gal4-CD3-PGK-BFP. In certain embodiments, the endogenous gene disrupted is CD3ε, the target molecule is selected from Her2/neu, EGFRvIII, and CD19, and the tumor sensing receptor is CAR. In an embodiment, the endogenous gene disrupted is CD3ε, the target molecule is Her2/neu, the tumor sensing receptor is CAR, and the expression cassette is NFAT-CD3-PGK-BFP.

A method of treating cancer in a patient is also provided. The method comprises administering T cells as described above or herein or prepared by any method described above and herein, to a patient in need thereof. In certain aspects, the T cells are tumor-activated alloreactive T cells which are alloreactive with respect to the patient.

BRIEF DESCRIPTION OF THE DRAWINGS

The accompanying drawings are incorporated in and constitute a part of this specification and illustrate various methods and compositions disclosed herein. However, the disclosure not limited to the precise arrangements and instrumentalities of the embodiments depicted in the drawings.

FIG. 2A depicts an illustration of an alloreactive T cell including a schematic of a T cell receptor (TCR)/CD3 complex. A TCR is a heterodimer of an alpha (α) chain and a beta (β) chain. The TCR/CD3 complex comprises two CD3 epsilon (ε) chains, a CD3 gamma (γ) chain, a CD3 delta (δ) chain, and two CD3 zeta (ζ) chains. The gray boxes indicate ITAM domains in the CD3 chains. ITAM: immunoreceptor tyrosine-based activation motif. The alloreactive T cell is genetically altered to disrupt the expression of CD3ε (ε knockout) using techniques such as CRISPR-Cas9 to generate an activation-incompetent T cell. The c knockout T cell is depicted in FIG. 2B and the TCR/CD3 complex comprises a CD3γ chain, a CD3δ chain, and two CD3ζ chains. The activation-incompetent T cell illustrated in FIG. 2B is genetically altered by introducing a tumor-associated antigen (TAA)-specific tumor-sensing receptor (in this embodiment a SynNotch-based tumor-sensing receptor) into the T cell, and a CD3ε expression cassette in the nucleus of the cell. TCE: transcription control element. ε gene: CD3ε gene. These steps produce the tumor-activated alloreactive T-cell depicted in FIG. 2C. FIG. 2D depicts the activities of the tumor-activated alloreactive T-cell (depicted in FIG. 2C) in the presence of a tumor cell expressing the tumor cell expressing the tumor antigen recognized by the TAA-specific tumor-sensing receptor. Upon binding of the tumor antigen and the TAA-specific tumor sensing receptor, the transcription activator is cleaved from the sensor and activates transcription of the CD3ε gene in the expression cassette. Resulting production of CD3ε polypeptides restores functional TCR/CD3 expression on the T cell, which can then recognize and bind to allo-peptide-HLA on the tumor cells. This results in T cell activation and tumor cell killing (the first kill). Expression of TCR/CD3 expression on the T cell is expected to persist for a period of time, although signaling from the tumor sensing receptor will start to decay once the tumor cell is killed. As depicted in FIG. 2E, T cells may therefore be able to kill other HLA+ tumor cells or stromal cells in the vicinity. The alloreactivity of the T cell may be sustained by encountering other TAA-expressing tumor cells. After exiting the tumor, the T cells will lose alloreactivity due to the decay of SynNotch signaling and the loss of CD3ε expression. FIGS. 2A-C illustrate ex vivo e, and FIGS. 2D and E illustrate in vivo activities.

FIG. 4 depicts flow cytometry data for wild type D10 cells and for D10 cells with mouse CD3 zeta (0 knocked out (D10-ζ-KO) using a gRNA with the crRNA sequence 5'-cuccugg-gaaccgcacgugg-3' (SEQ ID NO: 14). Cells were stained with antibodies specific for TCRβ and CD3ε and analyzed using flow cytometry.

FIGS. 7A and 7B show data for the genetically modified primary human $CD8^+$ T cells stimulated with MDA-MB-231 cells. FIG. 7C shows data for the cells modified as in FIG. 7B after CD3ε knockout.

FIG. 8A depicts data for wild type T cells and FIG. 8B depicts data for CD3-KO T cells, three days after electroporation with CRISPR-Cas9 complex (hCD3ε sgRNA Hs.Cas9.CD3E.1.AC and Alt-R Sp Cas9 Nuclease V3). FIG. 8C depicts data for purified CD3-KO cells.

FIG. 22A depicts data for the expression of CD3ε on unsorted and sorted CD3KO-Her2SN-εCS T cells. Sorted CD3KO-Her2SN-εCS T cells showed significantly lower levels of CD3ε expression than WT T cells. FIG. 22B: Sorted CD3KO-Her2SN-εCS T cells were stained with anti-Myc-Tag for SynNotch expression. The presence of CD3ε cassette is indicated by the constitutively expressed blue fluorescence protein (BFP).

FIG. 23A: Wild type MDA-MB-231 cells express low levels of Her2. Cells were stained with anti-CD340/Her2 antibody (Biolegend). FIG. 23B: MDA-Her2 and MDA-luci-Her2 express high levels of Her2. MDA-Her2KO and MDA-luci-Her2KO did not express Her2. To stably express luciferase, the cells were transduced with a pLX313 lentiviral vector encoding firefly luciferase and a hygromycin resistant gene. To stably express luciferase and Her2, the cells were transduced with a pLVx lentiviral vector encoding Her2 and a puromycin resistant gene. The transduced cells were selected in corresponding antibiotics to select stable expressors. For Her2 KO, sgRNA Hs.Cas9.ERBB2.1.AA (IDT) with the crRNA sequence of 5'-CAACUACCUUUC-UACGGACG-3' (SEQ ID NO: 21) was used. FIG. 23C: WT and all modified MDA-MB-231 cells express HLA-I. Cells were stained with anti-human-HLA-A,B,C antibody (Biolegend).

FIG. 27A: The expression of CD3ε on unsorted and sorted CD3KO-Her2CAR-εCS T cells. FIG. 27B: Sorted CD3KO-Her2CAR-εCS T cells were stained with recombinant human Her2 followed by anti-CD340/Her2 for Her2-specific CAR expression. The presence of CD3ε cassette is indicated by the constitutively expressed blue fluorescence protein (BFP).

DETAILED DESCRIPTION

Figure 1:
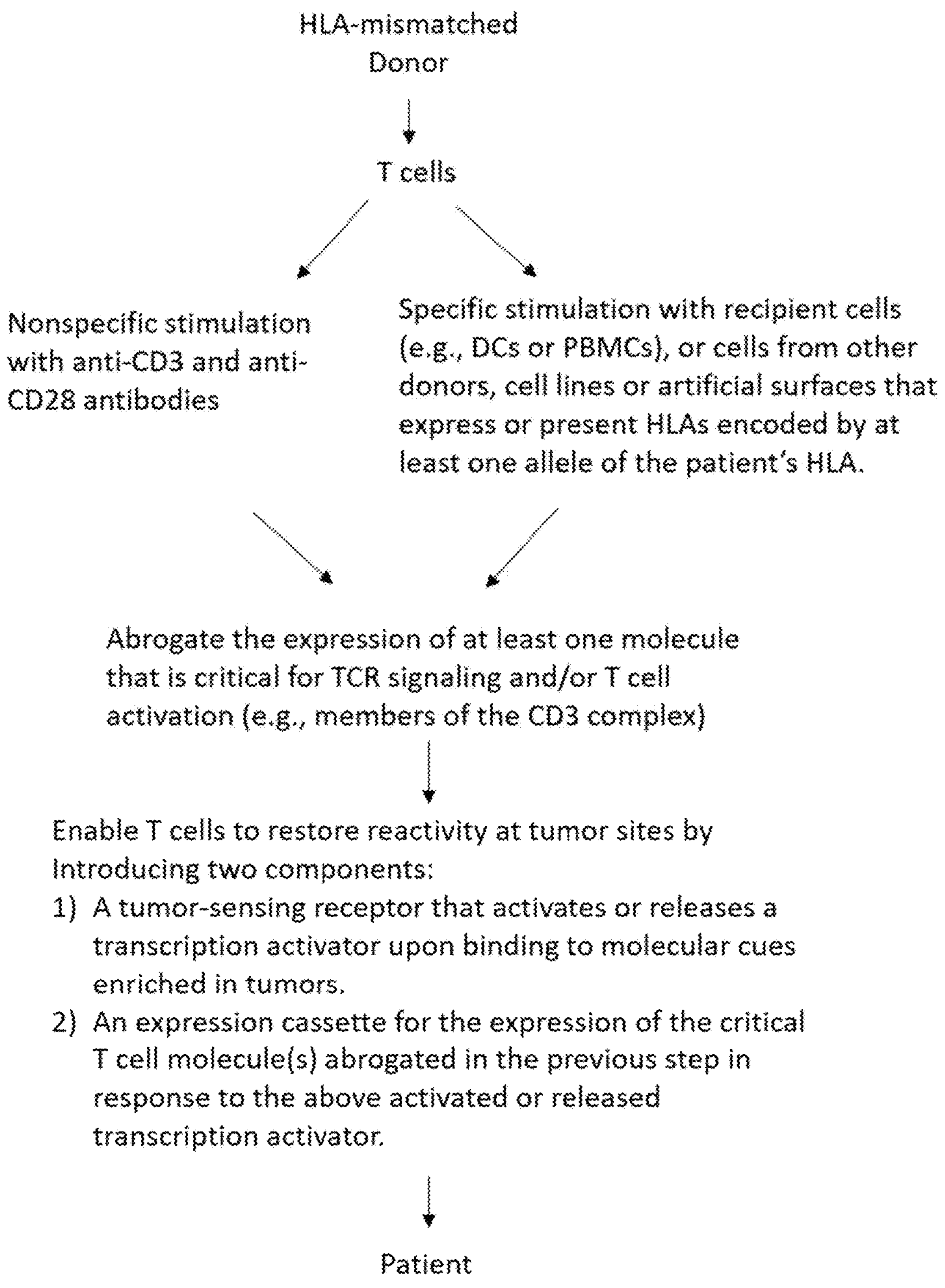
FIG. 1 depicts four steps of generating tumor-activated alloreactive T cells disclosed herein.

The present disclosure is directed to a tumor-activated alloreactive or xenoreactive T cell, a method of making the tumor-activated alloreactive or xenoreactive T cell, and methods of using the tumor-activated alloreactive or xenoreactive T cell.

Definitions & Abbreviations

Unless defined otherwise, all technical and scientific terms used herein generally have the same meaning as commonly understood by one of ordinary skill in the art to which this invention belongs. It is also to be understood that the terminology used herein is for the purpose of describing particular embodiments only, and is not intended to be limiting.

The following abbreviations/acronyms have the following meanings unless otherwise specified:

cDNA complementary DNA
DNA deoxyribonucleic acid
EDTA ethylenediaminetetraacetic acid
kDa kiloDalton
MW molecular weight
NCBI National Center for Biotechnology Information
PEG polyethyleneglycol
pI isoelectric point
ppm parts per million
PVA poly(vinyl alcohol)
PVP poly(vinylpyrrolidone)
RNA ribonucleic acid
SDS-PAGE sodium dodecyl sulfate polyacrylamide gel electrophoresis
w/v weight/volume
w/w weight/weight
v/v volume/volume
wt % weight percent
° C. degrees Centigrade
$H_2O$ water
$dH_2O$ or DI deionized water
$dIH_2O$ deionized water, Milli-Q filtration
g or gm grams
μg micrograms
mg milligrams kg kilograms
μL and μl microliters
mL and ml milliliters
mm millimeters
micrometer
M molar
mM millimolar
micromolar
U units
sec seconds
min(s) minute/minutes
hr(s) hour/hours
ETOH ethanol
eq. equivalents
N normal Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, MOLECULAR CLONING, A LABORATORY APPROACH, Cold Spring Harbor Press, Cold Spring Harbor, NY, and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

As used herein, the term "autologous" is meant to refer to any material derived from the same individual to which it is later to be re-introduced into the individual.

An "effective amount" as used herein, means an amount of a therapeutic compounds or combination thereof, when administered to a patient suffering from a malignancy provides a therapeutic benefit in alleviating one or more manifestations of the malignancy. It is understood, however, that the full therapeutic effect does not necessarily occur by administration of one dose, and may occur only after administration of a series of doses. Thus, an effective amount may be administered in one or more administrations. In the context of therapeutic or prophylactic applications, the amount of active agent administered to the subject will depend on the type and severity of the disease or condition and on the characteristics of the subject, such as general health, age, sex, body weight and tolerance to drugs. It will also depend on the degree, severity and type of disease or condition. The skilled artisan will be able to determine appropriate dosages depending on these and other factors.

As used herein, the term "individual" or "patient" or "subject" (as in the subject of the treatment) refers to any animal (e.g., a mammal), including, but not limited to humans, non-human primates, rodents, and the like. The individual is, in one embodiment, a human being. Typically, the terms "individual", "subject" and "patient" are used interchangeably herein in reference to a human subject.

As used herein, the term "donor" refers to the individual person or animal from whom the T cells to be manipulated and used as therapeutics are obtained.

As used herein, a "recipient" refers to an individual, patient, or subject to whom the T-cells of the disclosure are intended to be administered and/or who receives the T-cells of the disclosure. A "recipient" may refer to a category of individual, patient or subject having a common characteristic, such as a particular HLA profile.

The term "HLA mismatched" refers to the condition that the HLA alleles expressed in the tissues of a first individual person are different from those in the tissues of a second individual person. The term specifically refers to the alleles in the highly polymorphic loci HLA-A, HLA-B, HLA-C, DRB1, DPA1, DPB1, DQA1, and DQB1.

The term "allogeneic" refers to the source of T cells used for manipulation and therapy are taken from a person other than the patient.

The term "alloreactive" refers to the ability of certain T cells of an individual person to react to cells and tissues of another individual person with mismatched HLA through TCR recognition of mismatched HLA and antigens presented by the mismatched HLA molecules.

The term "xenogeneic" refers to the source of T cells used for manipulation and therapy are taken from a non-human animal.

The term "xenoreactive" refers to the ability of certain T cells from an individual of a certain species to react to the cells and tissues of an individual of a different species through TCR recognition of mismatched HLA and antigens presented by mismatched HLA molecules.

As used herein, a "normal subject" or "control subject" refers, depending on the context, to a subject not suffering from a malignancy.

As used herein, a "control sample" refers to a sample from a control subject or a sample representative of a population of control subjects.

To "treat" a disease as the term is used herein, means to reduce the frequency or severity of at least one sign or symptom of a disease or disorder experienced by a subject. Treating may include the postponement of further disease progression, or reduction in the severity of symptoms that have or are expected to develop, ameliorating existing symptoms and preventing additional symptoms.

An "antibody" (Ab) shall include, without limitation, an immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The antibodies may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using ANTIBODIES: A LABORATORY MANUAL, Cold Spring Harbor Laboratory Press, NY; Harlow et al., 1989, ANTIBODIES: A LABORATORY MANUAL, Cold Spring Harbor, New York; Houston et al., 1988, *Proc. Natl. Acad. Sci. USA* 85:5879-5883; Bird et al., 1988, *Science* 242:423-426).

An "antigen binding portion" of an Ab (also called an "antigen-binding fragment") or antigen binding portion thereof refers to one or more sequences of an Ab (full length or fragment of the full length antibody) that retain the ability to bind specifically to the antigen bound by the whole Ab. Examples of an antigen-binding fragment include intrabody, bispecific antibody, Fab, F(ab')2, scFv (single-chain variable fragment), Fab', dsFv, sc(Fv)2, and scFv-Fc.

The term "nanobody" (Nb), as used herein, refers to the smallest antigen binding fragment or single variable domain ($V_{HH}$) derived from naturally-occurring heavy chain antibody and is known to the person skilled in the art. They are derived from heavy chain only antibodies, seen in camelids (Hamers-Casterman et al., 1993; Desmyter et al., 1996). In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a $V_{HH}$ antibody As used herein, the term "variable domain" refers to immunoglobulin variable domains defined by Kabat et al., SEQUENCES OF IMMUNOLOGICAL INTEREST, 5th ed., U.S. Dept. Health & Human Services, Washington, D.C. (1991). The numbering and positioning of CDR amino acid residues within the variable domains is in accordance with the well-known Kabat numbering convention. VH, "variable heavy chain" and "variable heavy chain domain" refer to the variable domain of a heavy chain. VL, "variable light chain" and "variable light chain domain" refer to the variable domain of a light chain.

A "humanized" antibody refers to an Ab in which some, most or all of the amino acids outside the CDR domains of a non-human Ab are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

By the term "synthetic antibody," as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

Reference to the wild-type protein is understood to include the mature form of the protein. A "mature" polypeptide means a wild-type polypeptide sequence from which a signal sequence has been cleaved during expression of the polypeptide. The mature protein can be a fusion protein between the mature polypeptide and a signal sequence polypeptide.

The term "variant," with respect to a polypeptide, refers to a polypeptide that differs from a specified wild-type, parental, or reference polypeptide in that it includes a man-made substitution, insertion, or deletion at one or more amino acid positions. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

The term "recombinant," when used in reference to a subject cell, nucleic acid, protein or vector, indicates that the subject has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell, or express native genes at different levels or under different conditions than found in nature.

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, "hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M $Na_3$ citrate, pH 7.0). Hybridized, duplex nucleic acids are characterized by a melting temperature ($T_m$), where one half of the hybridized nucleic acids are unpaired with the complementary strand. Mismatched nucleotides within the duplex lower the $T_m$. A nucleic acid encoding a variant α-amylase may have a $T_m$ reduced by 1° C.-3° C. or more compared to a duplex formed between the nucleotide of SEQ ID NO: 2 and its identical complement.

As used herein, a "synthetic" molecule is produced by in vitro chemical or enzymatic synthesis rather than by an organism.

As used herein, the terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the term "expression" refers to the process by which a polypeptide is produced based on a nucleic acid sequence. The process includes both transcription and translation.

A "selective marker" or "selectable marker" refers to a gene capable of being expressed in a host cell to facilitate selection of host cells carrying the gene. Examples of selectable markers include but are not limited to antimicrobials (e.g., hygromycin, bleomycin, or chloramphenicol) and/or genes that confer a metabolic advantage over cells that lack the metabolic gene, such as a nutritional advantage on the host cell.

A "vector" refers to a polynucleotide sequence designed to introduce nucleic acids into one or more cell types. Examples of vectors include but are not limited to, linear polynucleotides, polynucleotides associated with ionic or amphiphilic compounds, plasmids, and viruses. Thus, the term "vector" includes an autonomously replicating plasmid or a virus. The term is also construed to include non-plasmid and non-viral compounds which facilitate transfer of nucleic acid into cells, such as, for example, polylysine compounds, liposomes, and the like. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation. A control sequence is also referred to herein as a transcription control element ("TCE"). Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "linker", also referred to as a "spacer" or "spacer domain" as used herein interchangeably, refers to a an amino acid or sequence of amino acids that that is optionally located between two amino acid sequences in a fusion protein.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

As used herein, "biologically active" refer to a sequence having a specified biological activity, such an enzymatic activity.

"Percent sequence identity" means that a variant has at least a certain percentage of amino acid residues identical to a wild-type protein, when aligned using the BLAST algorithm with default parameters. A variant with five amino acid substitutions or deletions of a 617 amino acid polypeptide, for example, would have a percent sequence identity of 99% (612/617 identical residues×100, rounded to the nearest whole number) relative to the mature polypeptide. Such a variant would be encompassed by a variant having "at least 99% sequence identity" to the mature polypeptide.

As used herein, the term "fusion protein" or "fusion polypeptide" is a polypeptide comprised of at least two polypeptides, optionally also comprising a linking sequence, and that are operatively linked into one continuous protein. The two polypeptides linked in a fusion protein are typically derived from the at least two independent sources (i.e., not from the same parental polypeptide), and therefore a fusion protein comprises the at least two linked polypeptides not normally found linked in nature. Typically, the at least two polypeptides can be operably attached directly by a peptide bond, or may be connected by a linking group, such as a spacer domain. An example of a fusion polypeptide is a polypeptide that functions as a receptor for an antigen, wherein an antigen binding polypeptide forming an extracellular domain is fused to a different polypeptide, forming a "chimeric antigen receptor". Also contemplated herein are fusion proteins comprising 3, 4, 5, 6, 7, 8, 9, or 10 or more heterologous polypeptides.

As used herein, "abrogating the expression" of a gene refers to the disruption the expression of the gene.

As used herein "abrogating the function" of a gene product refers to disrupting the function and activity of the gene product.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

An "isolated" compound as used herein means that the compound is removed from at least one component with which the compound is naturally associated with in nature.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DESCRIPTION

Embodiments of the present invention are described below. It is, however, expressly noted that the present invention is not limited to these embodiments, but rather the intention is that modifications that are apparent to the person skilled in the art and equivalents thereof are also included.

This disclosure exploits the alloreactivity or xenoreactivity of allogeneic T cells to broadly target cancer cells and stromal cells in tumors or tissues with blood cancer cell accumulation. Each T cell naturally expresses a unique type of T cell receptor (TCR) on the cell surface to recognize a specific antigen on target cells. In humans, the antigen is a short peptide (~10 amino acid residues) in complex with a cell surface protein termed human leukocyte antigen (HLA). HLA class I (HLA-I) proteins comprise an a heavy chain and a β2 microglobulin (β2M). Only the α-chain participates in peptide binding and TCR interaction. The α chain is encoded by three gene loci: HLA-A, B, and C, leading to the expression of three gene products on cell surfaces. All three loci are highly polymorphic, each with hundreds to thousands of different alleles among the human population. HLA-I molecules are expressed on virtually all human cells including many tumor cells. Peptide-HLA-I antigens are recognized by TCRs expressed on $CD8^+$ cytotoxic T cells, which kill antigen-expressing cells upon activation. HLA class II (HLA-II) molecules are αβ heterodimers and both chains take part in peptide presentation and TCR binding. HLA-II molecules are encoded by six gene loci (HLA-DRA1, DRB1, DPA1, DPB1, DQA1 and DQB1), all of which are high polymorphic except DRA1. HLA class II are mostly expressed on B cells and specialized antigen presenting cells (APCs) but can also be induced on epithelial cells and on a variety of solid tumor cells (20). Peptide-HLA-II antigens activate $CD4^+$ helper T cells, which release inflammatory cytokines and help the survival and function of $CD8^+$ T cells. Due to the many polymorphisms in each HLA gene locus in the human population, it is rare for any two individuals to express the same set of HLA genes. A significant proportion (1-10%) of T cells of an individual can recognize and respond to cells from another individual through TCR recognition of mismatched HLAs and the antigen presented by the mismatched HLA molecules (21, 22). T cell alloreaction, i.e., reaction to cells and tissues from a different individual of the same species, plays a critical role in organ transplant rejection through host vs. graft (HvG) activity (23). If the recipient of transplantation is immunocompromised and cannot eliminate T cells from the graft through HvG, the grafted T cells may attack the recipient's tissues and cause severe, sometimes lethal graft vs host (GvH) disease (24). For these reasons, close matches in HLA genes between the organ donor and the recipient are necessary for successful transplantation. Matches at the HLA-A, HLA-B, HLA-C and HLA-DRB1 loci have been found to be most critical for successful transplantation, suggesting their higher degree of involvement in alloreactions than HLA-DP and HLA-DQ (25). Because of the diploid nature of human genome, a match at all eight HLA-A, HLA-B, HLA-C and HLA-DRB1 loci (8/8 match) has the best chance of success in transplantation. T cell reaction to cells from a different species, i.e., xenoreaction, tends to be stronger than alloreaction (26) and is the main roadblock for using animals such as pigs as sources of organs for human transplantation. It should be noted that the term "allogeneic" refers to the source of T cells being from an individual that is different from the recipient. "Alloreactive" may refer to the reactivity of transplanted allogeneic T cells to the recipient's tissues in GvH or the reactivity of the recipient's T cells to transplanted tissues, including transplanted allogeneic T cells, in HvG. Not all allogeneic T cells have alloreactivity to the recipient's tissues. On the other hand, the alloreactive T cells used for cancer treatment in this disclosure are all allogeneic in nature. Since the T cells of this disclosure are administered to a recipient with cancer, the terms "recipient" and "patient" are used interchangeably depending on the context.

Alloreactive T cells have been used for treating cancer in special settings. Donor lymphocyte infusion (DLI) is a well-established treatment for patients who have received an allogeneic stem cell transplant for a hematological malignancy but have residual disease. In such cases, the patient receives strong chemotherapy or radiation therapy to kill cancer cells. Stem cells from a donor with partially matched HLAs are used to restore normal hematopoietic activity damaged by the radiation or chemotherapy. T cells from the same donor are then infused to eliminate residual cancer cells through alloreactions. Approximately 70% of these patients develop GvH diseases, which is correlated with lower risk of relapse of their malignancy (27, 28). A unique factor in this case is that the infused allogeneic T cells are unlikely to be eliminated by the patient through HvG because patient T cells are derived from stem cells of the same donor and tolerated to donor HLAs.

Using alloreactive or xenoreactive T cells to treat tumors therefore must overcome two main hurdles. The first is to avoid or minimize the patient's HvG activities to the allogeneic and xenogeneic T cells in order to allow the cells to survive and execute anti-tumor activities. In this regard, lympho-depletion caused by radiation or chemotherapy received by cancer patients compromises the patients' immune system and may create a window of reduced HvG activities for treatment using allogeneic T cells (29). Progresses have also been made in making allogeneic T cells "stealthy" to the recipient's immune system. Using gene-editing technologies such as CRISPR-Cas9, HLA expression can be knocked out in allogeneic T cells, making them "invisible" to recipients' T cells (30, 31). The cells can be further modified to express non-classical HLA-I molecules such as HLA-E and HLA-G to protect them from natural killer (NK) cells (32), which kill cells that do not express any HLA. The second hurdle is to restrict the destructive alloreactivity or xenoreactivity of T cells to tumor sites so that damages to normal tissues are minimized and severe GvH diseases are avoided.

This disclosure describes a method of generating genetically modified T cells with alloreactivities or xenoreactivities restricted to tumor sites or tissues with blood cancer cell accumulation. The method comprises abrogating the ability of T cells to activate through TCR and introducing a mechanism that restores the ability at the tumor sites in response to molecular cues enriched on tumor cells or in the tumor microenvironment. This disclosure further describes the genetically modified T cells made and therapeutic uses thereof.

I. Method of Generating Tumor-Activated Alloreactive or Xenoreactive T Cells

The disclosure describes the methods of generating tumor-activated alloreactive or xenoreactive T cells and their use in treating patients with cancer. The T cells are generated in four main steps (FIG. 1, depicting alloreactive T cells only for simplicity).

The first step is T cell collection. T cells are isolated from the blood of an HLA mismatched donor. The degree of HLA mismatch is determined by comparing the alleles of the donor and the recipient at the HLA-A, HLA-B, HLA-C, DRB1, DPA1, DPB1, DQA1 and DQB1 loci. Donors with at least one HLA allele mismatched with that of the recipient or patient are selected. Preferably the mismatch allele is at one of the HLA-A, HLA-B, HLA-C, DRB1 loci. Donors with mismatches at higher numbers of loci are preferred for strong T cell alloreactivities. Xenogeneic T cells are isolated from an animal such as a pig. Total T cells as a mixture of $CD4^+$ and $CD8^+$ T cells, $CD4^+$ T cells alone, or $CD8^+$ T cells alone, can be isolated from the donor's blood using conventional methods known in the art or by using commercially available kits using purification columns or magnetic beads.

The second step is stimulation, which activates the T cells and drives them to proliferate (i.e., drive the cells into cell cycle). This step aids genetic manipulation of the T cells in the following steps and expands the T cells. T cells can be stimulated nonspecifically or specifically. For nonspecific stimulation, T cells can be cultured with anti-CD3 and antibody and anti-CD28 antibodies coated on beads or plastic surfaces to activate all T cells regardless of their alloreactivity or xenoreactivity. For specific stimulation, T cells can be co-cultured with cells from the patient, including peripheral blood mononuclear cells (PBMCs), cultured monocyte-derived dendritic cells (DCs), and cells isolated from resected tumors. Alternatively, T cells can be cultured with PBMCs or DCs from another donor who shares at least one common HLA allele with the patient. Alloreactive T cells proliferate in response to PBMC from an HLA-mismatched individual as a result of T cell stimulation by antigen presenting cells (APCs) in PBMCs though TCR-HLA interaction. This is the basis for mixed lymphocyte reaction (MLR), which has been used to determine the alloreactivity of T cells since 1964) (33). To expand alloreactive T cells for the current disclosure, T cells from an HLA-mismatched donor can be labeled with the cell division tracking fluorescent dye carboxyfluorescein succinimidyl ester (CFSE) and cultured with PBMCs from the patient. Prior to the culture, the patient PBMCs are treated with irradiation (2,500 rads) or chemotherapy drugs, such as mitomycin C to abrogate their proliferation potential. Proliferated donor T cells with low CFSE levels are sorted using flow cytometry and used as the source of alloreactive T cells for downstream genetic manipulations. The efficiency of alloreactive T cell expansion can be increased by using DCs. As professional antigen presenting cells (APCs), DCs express high levels of HLA-I, HLA-II and a host of costimulatory molecules such as CD40, CD80 and CD86. T cells expanded by DCs may also strongly activate T cells through engaging TCR and costimulatory receptors such as CD28. Monocyte-derived DCs (MoDCs) have been tested for immunotherapies against cancer, autoimmune and other disease for decades. As of August 2019, 120 human clinical trials were listed on ClinicalTrials.gov. MoDCs have been shown to efficiently stimulate the expansion of alloreactive T cells (34-36). Generation of MoDCs involves culturing enriched monocytes from an apheresis collection of PBMCs in the presence of granulocyte-macrophage colony-stimulation factor (GM-CSF) and interleukin-4 (IL-4) (34-42). The processes of enriching monocyte, generating and cryopreserving MoDCs are well established (43, 44) and a number of commercial kits are available for generating clinical grade MoDCs. To enhance the ability of T cells to recognize and kill tumor cells, T cells may be stimulated by MoDCs in the presence of lysate generated with tumor cells from the patient or with a tumor cell line derived from a tumor of the same type from another individual (45-47).

T cells can also be expanded by culturing with cell lines that express HLA proteins encoded by at least one of the patient's HLA alleles or artificial surfaces such as plastics that are coated with HLA proteins encoded by at least one of the patient's HLA alleles. Specific stimulation leads to selective activation and expansion of T cells that are alloreactive or xenoreactive to patient HLAs. Stimulated and expanded T cells can be cryo-preserved, for instance in DMSO at a suitable percentage, such as 10% DMSO or 7.5% DMSO, and thawed later for downstream genetic manipulations. The activation step may be omitted if genetic manipulations in the following steps can be achieved without T cell activation and T cell activation and expansion after infusion into the patients are preferred.

Figures 2A, 2B, 2C:
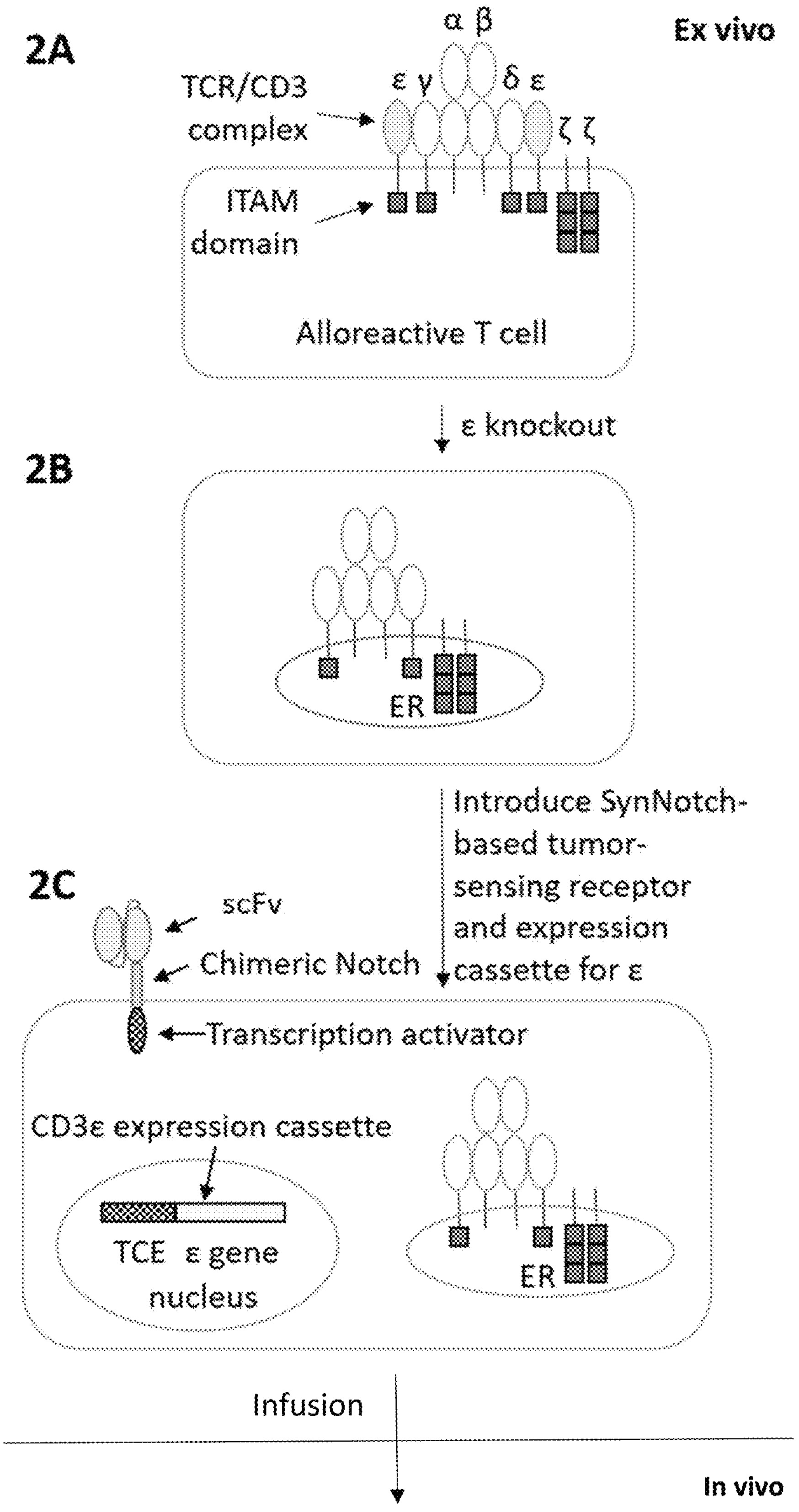
FIGS. 2A-2E illustrate the generation and use of a tumor-activated alloreactive T-cell that uses a SynNotch-based tumor-sensing receptor and a CD3ε expression cassette.

The third step is to abrogate the ability of T cells to activate through TCR signaling, thus making the T cells activation-incompetent. This is achieved through disrupting the expression or function of at least one molecule that is necessary for TCR signaling and T cell activation (FIG. 1 and FIGS. 2A and 2B). For instance, the expression of a gene encoding a critical protein can be disrupted using gene-editing technologies such as CRISPR-Cas9, transcription activator-like effector nuclease (TALENs), megaTALS, zinc-finger nucleases, or homing endonucleases (48). The disruption occurs on both copies of the target gene in a cell, leading to complete lack of expression in the cell and its progenies. In recent years, CRISPR-cas9 has become a routine technology in research labs and has seen numerous clinical applications (49) including in immunotherapies (50). A myriad of commercial products are available for guide RNA (gRNA) design and synthesis, recombinant cas9 proteins, and tools for delivering gRNA and cas9 into many cell types. For primary human T cells, electroporation of gRNA-cas9 ribonucleoprotein (RNP) has become the method of choice for highly efficient gene knockout (51, 52). Genes that encode polypeptides that are necessary for TCR signaling and T cell activation can be transmembrane proteins. Exemplary transmembrane proteins expressed on the plasma membrane include CD3ε, CD3ζ, CD3γ, CD3δ, CD4, CD8α, CD8β, LAT, TRIM, CD45, CD28, LFA-1, CD2, CD54, CD52, CD148, and CD58. Genes that encode polypeptides that are necessary for TCR signaling and T cell activation can encode intracellular signaling molecules involved in TCR signaling and T cell activation. Exemplary intracellular signaling molecules include but are not limited to Lck, Zap70, calcineurin, PI3K, Fyn, PLCγ, SLP76, PKCθ, AKT, NcK, and PDK1. The sequences of these exemplary molecules are readily available in public databases, such as National Institutes of Health GenBank® (U.S. Department of Health and Human Services) and UniProt. A number of free online tools are available for designing gRNA sequences to target any specific gene in the human genome. For example: URL:https://www.idtdna.com/site/order/designtool/index/CRISPR CUSTOM, URL:https://zlab.bio/guide-design-resources, and URL:https://www.synthego.com/products/bioinformatics/crispr-design-tool. Predesigned gRNAs for specific gene targets are also available from commercial sources, for example: URL: https://www.idtdna.com/site/order/designtool/index/CRISPR PREDESIGN.

The fourth step is to generate tumor-activated alloreactive or xenoreactive T cells by equipping the activation-incompetent T cells with the ability to restore activation competency at tumor sites (FIG. 1 and FIG. 2C). This is achieved by introducing a tumor-sensing receptor and an expression cassette for the disrupted gene. The tumor-sensing receptor comprises an extracellular domain that binds to molecules enriched on tumor cells or in the tumor microenvironment and leads to the release or activation of a transcription activator from the intracellular domain. The extracellular domain can be, for instance, a single chain variable fragment (scFv), a Fab fragment, a designed ankyrin repeat protein (DARPin), a nanobody, a TCR, an Fc receptor, a growth factor receptor, a chemokine receptor, or a hormone receptor. The types of molecules the receptors recognize include, for example, tumor associated antigens (TAAs) expressed on tumor cells, including CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, and the like. Cancer-associated antigens also include, e.g., 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, FAP, fibronectin extra domain-B, folate receptor 1, GD2, GD3 ganglioside, glycoprotein 75, GPNMB, HGF, human scatter factor receptor kinase, IGF-1 receptor, IGF-I, IgG1, Ll-CAM, IL-13, IL-6, insulin-like growth factor I receptor, integrin αvβ3, MORAb-009, MS4A1, MUC1, mucin CanAg, N-glycolylneuraminic acid, NPC-IC, PDGF-Ra, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, mesothelin, NKG2D, CD147, NKR2, B7H3, and vimentin. The tumor-sensing receptor can also recognize soluble factors enriched in the tumor microenvironment such as chemokines (53), growth factors, and growth hormone (54). In an alternative embodiment, the tumor sensing receptor recognizes molecules enriched in tissues with accumulation of blood cancer cells. For example, acute myeloid leukemia (AML) and myeloma cells tend to accumulate in bone marrow and lymphoid organs. The tumor sensing receptor may recognize molecules expressed on hematopoietic cells, especially lymphocytes that are abundant in these tissues. These molecules include CD45, CD19, CD20, CD4, CD8, CD2, CCR4, CD58, CD28, CD23, CD69, CD25, CD33, CD123 and CCL-1.

Figure 15:
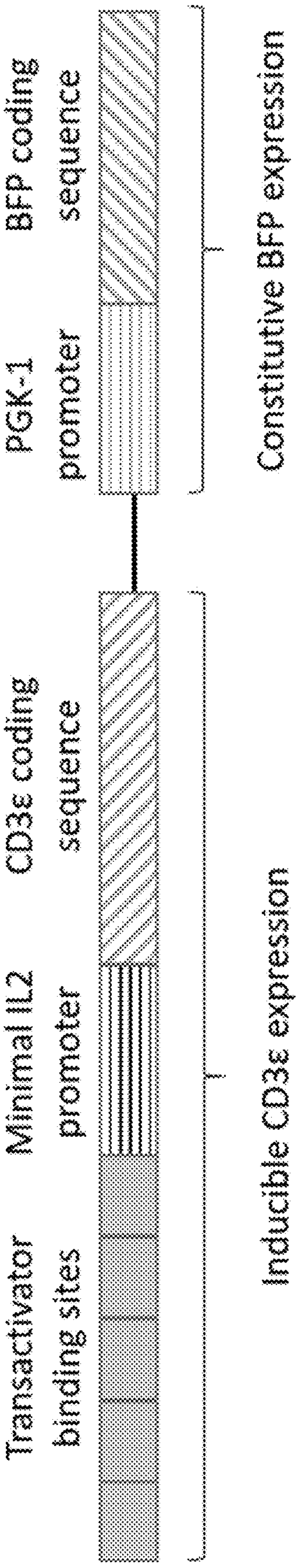
FIG. 15 depicts a CD3ε expression cassette containing sequences for constitutive BFP expression. The first (left) part of the cassette drives the inducible expression of CD3ε, consisting of multiple copies of trans activator binding sites, followed by a minimal IL2 promoter and a CD3ε coding sequence. The second (right) part of the cassette drives the constitutive expression of BFP, consisting of a PGK-1 promoter followed by a BFP coding sequence. The constitutive expression of GFP can be used as a marker for the presence of the whole cassette in the cell.

The expression cassette comprises DNA sequences of a promoter-like transcriptional control element (TCE) operably linked to a DNA sequence encoding a copy of the disrupted gene (FIG. 15). Binding of the transcription activator to the transcriptional control element drives the expression of the gene disrupted in the third step and restores the T cell's ability to activate and respond to antigens. Specifically, the TCE comprises multiple binding sites for the transactivation activator and a minimal promoter. Downstream of the TCE is the coding sequence of the gene disrupted in step 3. The coding sequence should encode the polypeptide of the gene but needs to be modified so that, for example, the gRNA used to disrupt the original gene using the CRISPR/Cas9 approach can no longer function. This can be achieved by creating multiple silent mutations on the sequence targeted by the gRNA, especially the PAM sequence. The expression cassette can additionally contain a coding sequence for a fluorescence protein such as BFP driven by a constitutively active promoter. The expression of the fluorescence protein serves as an indicator for the existence of the expression cassette in the cell.

Two types of engineered receptors can be employed as tumor-sensing receptors. The first type releases a transcription activator from the intracellular domain upon ligand binding. The transcription activator then translocates to the nucleus where it activates the expression cassette. These receptors include, by way of example, synthetic Notch (SynNotch) (14, 55) and (US patent publication US20160264665A1 and U.S. Pat. No. 9,834,608B2), Modular Extracellular Sensor Architecture (MESA) (56) (US patent publication US20140234851A1), and Tango (57). A SynNotch receptor exploits the ability of Notch to, upon ligand binding, cleaves and release its intracellular domain, which acts as a transcription factor after translocating to the nucleus. A SynNotch receptor is constructed by replacing the extracellular recognition domain of the Notch with a binding domain for a specific target and replacing intracellular domain with a transcription activator that can bind to the TCE in the expression cassette and drive the expression of gene of interest. DNA constructs for the patented SynNotch receptors with the Gal4-VP64 transcription activator and extracellular binders for CD19 (Addgene Cat. #79125) and Her2 (Addgene Cat. #85424) can be readily modified to construct SynNotch receptors with other binding specificities and/or transcription activators. DNA construct for the patented expression cassette with the Gal4-VP64 TCE is also available from Addgene (Cat. #79123) and can be used to for expression of gene of interest in response to SynNotch activation. A CD3ε expression cassette (Gal4-CD3-PKG-BFP) with an additional BFP coding sequence controlled by a constitutively active PGK-1 promoter is shown in SEQ ID NO: 1. Since SynNotch activation relies on surface-anchored ligands, it can be used to sense tumor antigens expressed on tumor cell surfaces such as Her2.

MESA can be used to sense soluble factors in the tumor microenvironment such as vascular endothelial growth factor (VEGF) or soluble tumor antigen shed from tumor cells. Target binding leads to receptor dimerization, which brings a protease on the intracellular domain of one monomer close to its substrate sequence on the other monomer. Cleavage of the substrate sequence leads to the release of a transcription activator linked to the cytosolic domain of the second monomer though the substrate sequence.

Tango is similar to MESA except that the protease is linked to an intracellular signaling molecule that is recruited to the receptor intracellular domain upon ligand binding. Therefore, Tango can be used to sense a variety of soluble factors in the tumor microenvironment, including chemokines (53), growth factors, and growth hormone (54).

Figure 14:
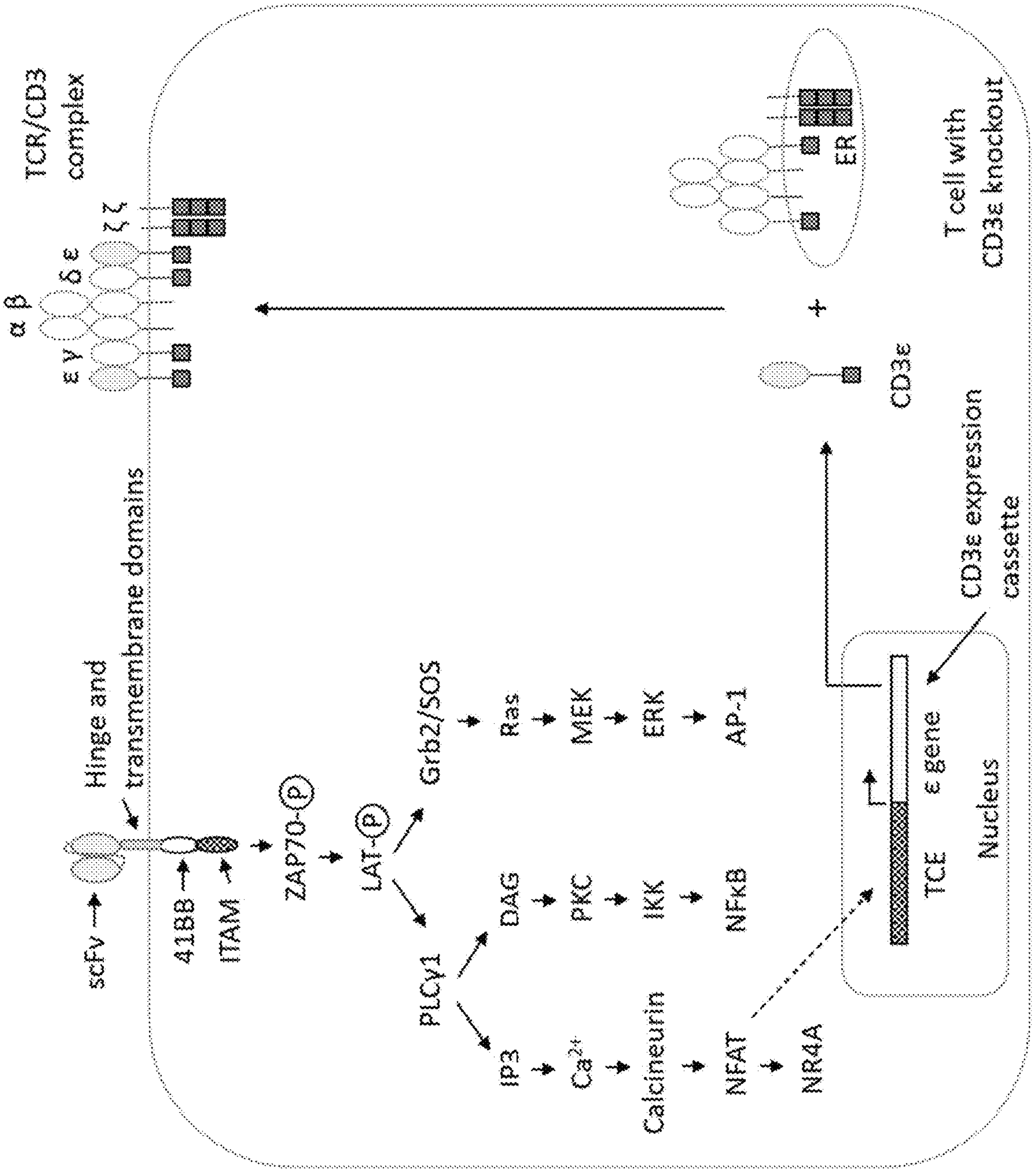
FIG. 14 illustrates a CAR-based tumor sensing receptor that restores the expression of CD3ε in an alloreactive CD3O T cell through signaling pathways and the activation of the transcription factor NFAT. The transcription control element (TCE) in the CD3 expression cassette consists of NFAT binding sequences. CD3 expression cassettes with TCEs containing binding sequences for other activated transcription factors NR4A, NFκB and AP-1 can also be used. The re-expression of CD3ε restores the surface expression of TCR/CD3 complex.

The second type of engineered tumor sensing receptors activates an endogenous transcription factor in T cells through signaling pathways. For example, a typical CAR with intracellular Immunoreceptor tyrosine-based activation motif (ITAM) domains can, in response to ligand binding, initiate multiple signaling pathways that lead to the activation of transcription factors NFAT, AP-1, NFκB/Rel, or NR4A1 (Nur77) (FIG. 14). Expression cassettes using TCE sequences containing binding sequence of these transcription factors to drive the expression of luciferase or GFP have been widely used in T cell activation reporter systems. The expression cassettes NFAT-CD3-PKG-BFP (SEQ ID NO: 2) AP1-CD3-PKG-BFP (SEQ ID NO: 3), NFκB-CD3-PKG-BFP (SEQ ID NO: 4) and NR4A-CD3-PKG-BFP (SEQ ID NO: 5) can be generated by replacing the Gal4 binding sites in the cassette Gal4-CD3-PKG-BFP with the binding sites for these transcription factors (TABLE 1). These expression cassettes can be used to drive the expression of downstream gene of interest as a result of ligand recognition by the CAR. The combination of CAR and transcription factor-driven expression cassette has been used to develop TRUCK (T cell redirected for universal cytokine-mediated killing), which secretes pro-inflammatory cytokines in response to CAR signaling to enhance CAR T cell function (58-60). TRUCK T cells have also entered clinical stage studies (NCT02498912 and NCT03721068).

TABLE 1

Transcription factor binding sites in expression cassettes for CAR based tumor sensing receptors.

| Transcription factor | Transcription factor binding motif | Transcription factor binding site in TCE | Number of motif repeats |
|---|---|---|---|
| AP-1 | TTGAGTCA (SEQ ID NO: 6) | TTGAGTCAAGATTGAGTCATCGTTGAGTC AGACTTGAGTCACTATTGAGTCAACTTTG AGTCATGCTTGAGTCAGTATTGAGTCA (SEQ ID NO: 7) | 8 |
| NFAT | GGAGGAAAA ACTGTTTCAT ACAGAAGGC GT (SEQ ID NO: 8) | GGAGGAAAAACTGTTTCATACAGAAGGC GTGGAGGAAAAACTGTTTCATACAGAAG GCGTGGAGGAAAAACTGTTTCATACAGA AGGCGTGGAGGAAAAACTGTTTCATACA GAAGGCGTGGAGGAAAAACTGTTTCATA CAGAAGGCGTGGAGGAAAAACTGTTTCA TACAGAAGGCGT (SEQ ID NO: 9) | 6 |
| NR4A1 | AAAGGTCAC (SEQ ID NO: 10) | AAAGGTCACAGAAAAGGTCACTCGAAAG GTCACGACAAAGGTCACCTAAAAGGTCA CACTAAAGGTCACTGCAAAGGTCACGTA AAAGGTCAC (SEQ ID NO: 11) | 8 |
| NFκB | GGGGAAATT CCCCT (SEQ ID NO: 12) | GGGGAAATTCCCCTAGAGGGGAAATTCC CCTTCGGGGGAAATTCCCCTGACGGGGA AATTCCCCTCTAGGGGAAATTCCCCTACT GGGGAAATTCCCCTTGCGGGGAAATTCC CCTGTA (SEQ ID NO: 13) | 7 |

DNA sequences for the tumor-sensing receptor and the expression cassette will be introduced into T cells using retroviral or lentiviral vectors, or transposon vectors such as Sleeping Beauty (Addgene) and piggyBac (VectorBuilder), to facilitate their stable integration into the T cell genome. In practice, step three and step four can be carried out at the same time or in reverse order. T cells non-specifically or specifically stimulated may be restimulated. T cells may be cryopreserved after stimulation/expansion, after step 3, or after step 4. The tumor-activated alloreactive T cells can therefore be generated in a number of ways. Three examples are: (i) stimulation/expansion→SynNotch and expression cassette introduction→CD3ε KO→(cryopreservation)→treatment; (ii) stimulation/expansion→cryopreservation→restimulation→SynNotch and expression cassette introduction→CD3ε KO→(cryopreservation)→treatment; and (iii) stimulation/expansion→CD3ε KO→cryopreservation→restimulation with PMA and ionomycin→SynNotch and expression cassette introduction→(cryopreservation)→treatment.

II. Tumor-Activated Alloreactive or Xenoreactive T Cells

The present disclosure provides a tumor-activated alloreactive or xenoreactive T-cell. The T-cell originates from a healthy donor for whom the genotype of at least one of the HLA-A, B, C and DRB1 loci is known to mismatch that of the patient. The T cell is modified to be activation-incompetent. Specifically, the T cell is genetically modified to disrupt expression of at least one endogenous gene encoding a molecule that is critical for TCR signaling and T cell activation. The gene to be disrupted can encode a transmembrane protein expressed on the plasma membrane. Non-limiting examples of exemplary transmembrane proteins include CD3ε, CD3ζ, CD3γ, CD3δ, CD4, CD8α, CD8β, LAT, TRIM, CD45, CD28, LFA-1, CD2, CD54, CD52, CD148, and CD58. The gene to be disrupted can encode an intracellular signaling molecule involved in TCR signaling and T cell activation. Non-limiting examples of exemplary intracellular signaling molecules include Lck, Zap70, calcineurin, PI3K, Fyn, PLCγ, SLP76, PKCθ, AKT, NcK and PDK1.

The activation-incompetent T cell further comprises an expression cassette comprising a copy of the gene encoding the molecule disrupted in the T cell. The expression vector comprises a transcriptional control element (TCE) operably linked to the gene, wherein binding of a cognate transcription activator to TCE results in expression of the gene encoding the molecule disrupted in the T cell. The T cell further comprises an exogenous tumor-sensing receptor. Binding of the tumor-sensing receptor to its cognate tumor antigen results in the release or activation of a transcriptional activator. A tumor antigen, as used herein, can be a tumor cell surface molecule, such as Her2, or a soluble factor present in a tumor microenvironment, such as vascular endothelial growth factor (VEGF), or a tumor antigen that is shed from tumor cells. In an alternative embodiment, the tumor-sensing receptor recognizes molecules enriched in tissues with accumulation of blood cancer cells. These include molecules expressed on hematopoietic cells that are abundant in bone marrow and lymphoid organs, The genetically modified T cell comprising the above-described features are contemplated to provide at least one of the following beneficial properties of confined alloreactivity at tumor sites or tissues with blood cancer cell accumulation and being able to target both tumor cells and tumor stromal cells that express HLA.

In certain embodiments of the tumor-activated alloreactive or xenoreactive T-cell and the method of making the same, the endogenous gene disrupted is selected from CD3ε, CD3ζ, CD3γ, CD3δ and CD8α. In an embodiment, the endogenous gene disrupted is CD3ε.

In certain embodiments, the target molecule is selected from Her2/neu, EGFRvIII, CD19, IL-13RR-a2, mesothelin, MUCI, EpCAM, GD2 and CEA. In certain embodiments, target molecule is selected from Her2/neu, EGFRvIII, CD19, IL-13RR-a2, mesothelin, and MUCI. In certain embodiments, the target molecule is selected from Her2/neu, EGFRvIII, and CD19. In an embodiment, the target molecule is Her2/neu. In an embodiment, the target molecule is CD19.

In certain embodiments, the expression cassette is selected from Gal4-CD3-PGK-BFP, NR4A-CD3-PKG-BFP, and NFAT-CD3-PKG-BFP. In certain embodiments, the tumor sensing receptor and expression cassette are selected from SynNotch and Gal4-CD3-PGK-BFP, CAR and NR4A-CD3-PKG-BFP, and CAR and NFAT-CD3-PKG-BFP.

In certain aspects, the sample of T cells is from a donor individual, and wherein the donor individual has at least one HLA allele mismatch relative to an intended recipient and the at least one HLA allele mismatch is located in a locus selected from the group consisting of: HLA-A, HLA-B, HLA-C, HLA-DRB1, HLA-DQA1, HLA-DQB1, HLA-DPA1 and HLA-DPB1, thereby producing tumor-activated alloreactive T cells. In certain embodiments, the at least one HLA allele mismatch is located in a locus selected from the group consisting of: HLA-A, HLA-B, HLA-C, and HLA-DRB1. In certain embodiments, the HLA allele mismatch comprises four alleles of, HLA-A, HLA-B, HLA-C, and HLA-DRB1, six alleles of, HLA-A, HLA-B, HLA-C, and HLA-DRB1 or all eight alleles of HLA-A, HLA-B, HLA-C, and HLA-DRB1. In an embodiment, the HLA allele mismatch comprises all eight alleles of HLA-A, HLA-B, HLA-C, and HLA-DRB1.

In certain embodiments, the endogenous gene disrupted is CD3ε, the target molecule is selected from Her2/neu, EGFRvIII, and CD19, and the tumor sensing receptor is SynNotch.

In certain embodiments, the endogenous gene disrupted is CD3ε, the target molecule is selected from Her2/neu, EGFRvIII, and CD19, the tumor sensing receptor is SynNotch, and the expression cassette is Gal4-CD3-PGK-BFP. In an embodiment, the endogenous gene disrupted is CD3ε, the target molecule is Her2/neu, the tumor sensing receptor is SynNotch, and the expression cassette is Gal4-CD3-PGK-BFP. In an embodiment, the endogenous gene disrupted is CD3ε, the target molecule is CD19, the tumor sensing receptor is SynNotch, and the expression cassette is Gal4-CD3-PGK-BFP. In an embodiment, the endogenous gene disrupted is CD3ε, the target molecule is Her2/neu, the tumor sensing receptor is CAR, and the expression cassette is NFAT-CD3-PGK-BFP.

III. Therapeutic Methods and Uses

Tumor-activated alloreactive or xenoreactive T cells will be expanded in culture supplemented with cytokines such as IL-2 and IL-7. The T cells will be introduced to patients or cryo-preserved for later use. T cells from different donors or stimulations may be used for the same patient to achieve the best results.

A number of additional steps may be taken to reduce HvG and enhance T cell survival in the patient. First, the patient may be conditioned with lympho-depleting radiation or chemotherapy agent prior to infusion to suppress the immune system.

Second, T cells may be obtained from donors with partially matched HLAs to reduce HvG. For example, T cells from a donor with a 5/8 match of the HLA-A, B, C, and DRB1 loci may be stimulated with patient cells or cell lines expressing the patient's alleles at the three mismatched loci to expand T cells that are alloreactive to these alleles. Third, T cells may be additionally modified to become "stealthy" to the patient's immune system. For example, the expression of HLA-A, B or C on T cells may be disrupted using CRISPR-Cas9. It should be noted that only the mismatched HLA gene(s) needs to be disrupted. Alternatively, the expression of all HLA-I molecules on cell surfaces may be abrogated by knocking out the shared β2M component, which is required for HLA-I to reach plasma membrane. This will be followed by introducing the α chain of HLA-E or HLA-G that is fused with β2M in step four (25). HLA-E and HLA-G are non-classical HLA molecules that are not involved in alloreactions but can inhibit attacks from natural killer (NK) cells.

Finally, for a patient with blood cancer and have received allogeneic hematopoietic stem cell transplantation, T cells may be obtained from the stem cell donor. In this case, the T cells will be tolerated by the patient's immune system. Moreover, in this case, T cells with restored alloreactivity will target only the patient's cells including cancer cells but avoid hematopoietic cells derived from the donor stem cells.

Figures 2D, 2E:
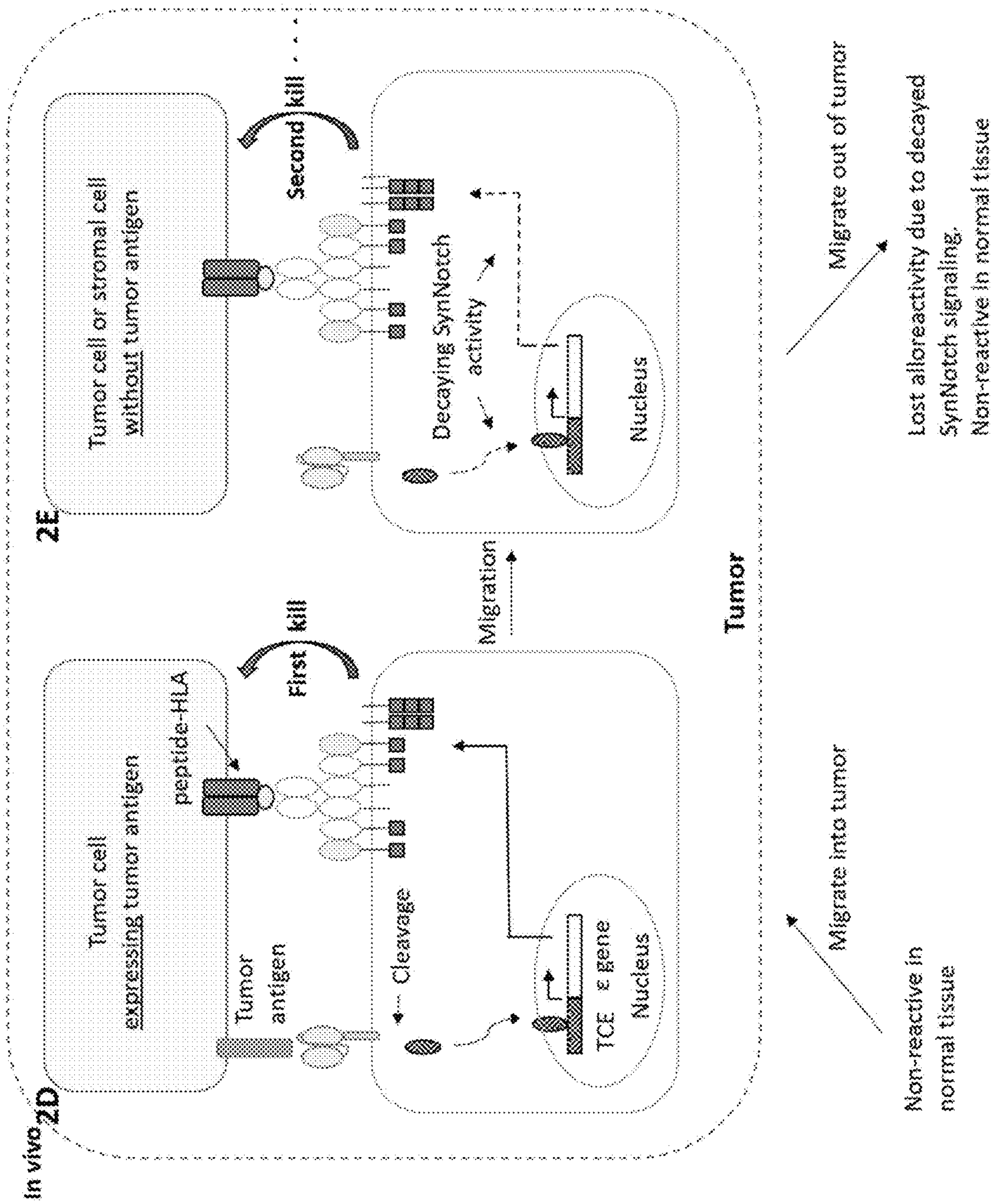

In the patient, due to deficiencies in critical components for TCR signaling, tumor-activated alloreactive or xenoreactive T cells cannot react to HLAs in normal tissues and should not cause GvH diseases. After migrating into tumors or tissues with blood cancer cell accumulation, however, engagement of tumor-sensing receptors by cue molecules enriched on in the tumor or target tissues will restore the T cells' alloreactivity or xenoreactivity, leading to T cell killing of HLA-expressing tumor cells and stromal cells (FIGS. 2D and 2E). The duration of reactivity depends on two factors. The first is the decaying rate of signals generated by the tumor sensing receptor, which determines how long the re-expression of the knocked out molecule can last after the receptor is disengaged from cue molecules. The half-life of expression driven by SynNotch receptors, for example, is around 8 hrs. The second is the distribution of tumor cue molecules within the tumor, which determines how often the tumor sensing receptor can be reengaged and activated. FIGS. 2A-2E illustrate the reactivity of an alloreactive T cell with CD3ε expression controlled by a TAA-specific tumor sensing receptor. CD3ε is a member of the TCR/CD3 complex. Loss of CD3ε expression leads to the retention of other components in the endoplasmic reticulum (61). In this case, a tumor-activated alloreactive T cell enters a tumor in which only a fraction of tumor cells expressing TAA. The T cell's ability to activate will be restored by one of the $TAA^+$ tumor cells through the interaction between TAA and the tumor-sending receptor that leads to CD3ε expression from the cassette, which restores surface expression of the TCR/CD3 complex. A partial restoration of TCR/CD3 expression level may be sufficient to restore T cell alloreactivity (62) Alloreactivity to HLAs on the tumor cells will activate the T cell and leads to the killing of the tumor cell (cis killing). Assuming that at least 50% CD3ε expression is required for the T cell to retain alloreactivity, the T cell will be able to kill other TAA-negative tumor cells (trans killing) for 8 hrs before losing its killing activity. The T cell may regain alloreactivity if it encounters other $TAA^+$ tumor cells before exiting the tumor. After exiting the tumor, the T cell will lose alloreactivity due to the decay of signaling from the tumor sensing receptor and CD3ζ expression, although it may cause limited damage to the surrounding normal tissue because of residual CD3ε expression. The scenario described above is consistent with a study of T cells expressing CD19-binding SynNotch that drives the expression of CARs specific tumor antigen ROR1 (63). When the T cells were administered into immunodeficient mice with bone marrow dissemination of lymphoma cells expressing both CD19 and ROR1, T cells expressed ROR1-specific CARs as the result of SynNotch-CD19 engagement and killed lymphoma cells (cis killing) in the mice. The T cells, however, killed $CD19^-/ROR^+$ bone marrow stromal cells (trans killing) as well. demonstrating that T cell toxicity extended to cells in the vicinity of SynNotch ligand-expressing cells. In another example of SynNotch-mediated trans killing, T cells expressing EGFRvIII-specific SynNotch that drives the expression of an EphA2-specific CAR were shown to kill both $EGFRvII^+EphA2^+$ and $EGFRvII^-EphA2^+$ tumor cells in mice (64).

The potency and specificity of tumor-activated alloreactive or xenoreactive T cells can be optimized in a number of ways. First, the potency of the cells may be controlled by selecting the level of HLA-mismatch between the donor and patient. For example, mismatches at all six HLA-I loci are expected to elicit stronger alloreaction than mismatch at only one.

Second, the ability of T cells to selectively target tumors and avoid normal tissues may be optimized by tuning the sensitivity of tumor-sensing receptors so that signals are generated only in response to high levels of tumor cue molecules. This may be achieved by adjusting the expression level, affinity, and extracellular linker length of the receptors.

Third, tumor selectivity of the T cells may be further controlled by using two tumor-sensing receptors, one releasing the DNA-binding domain of the transcription activator and another one releasing the activation domain of the transcription activator. This way, only cells expressing both tumor antigens can restore the expression of the key molecule, thus the reactivity of the T cells. Alternatively, tumor selectivity may be controlled by using multiple tumor-sensing receptors each directing the expression of a distinct component critical for TCR signaling. For instance, both CD3ζ and CD3ε may be knocked out and two tumor-sensing receptors will be introduced: one recognizes Her2 and directs the expression of CD3ζ; another recognizes a different tumor antigen MUC1 and directs the expression of CD3ε. Since both CD3ζ and CD3ε are required for cell surface expression of the TCR/CD3 complex, only cells expressing both tumor antigens can activate the T cells.

Fourth, the balance between tumor cell killing and normal tissue damage may be tweaked by adjusting the duration of alloreactivity. This can be achieved by manipulating the stability of mRNA transcripts for the re-expressed key molecule or by using degrons (65) to control its rate of protein degradation. The balance may also be adjusted by enhancing or reducing T cell survival through controlling the degree of lympho-depletion in the patient, thus the HvG activity against the allogeneic or xenogeneic T cells. Finally, the potency and specificity of tumor-activated alloreactive or xenoreactive T cells may be controlled by using a "universal" tumor-sensing receptor with an extracellular domain that binds to a peptide or chemical tag on a tumor antigen-binding soluble factor or with an extracellular domain derived from an Fc receptor that binds to tumor antigen-specific IgA, IgG or IgE antibodies. The tumor-sensing receptor will be activated by the soluble factor or the antibodies bound on tumor cells. The level of alloreactivity or xenoreactivity of the T cells can be manipulated by controlling the type and dose of the tumor-binding soluble factor or antibody.

Tumor-activated alloreactive or xenoreactive T cells are believed to have a number of advantages over CAR T cells in terms of efficacy and cost. First, once activated at the tumor site, allogenic T cells attack not only tumor cells expressing the tumor antigen, but also other tumor cells expressing HLA-I. Even though HLA-I downregulation is a common mechanism employed by tumor cells to escape immune surveillance, HLA-I expression is well preserved in many cancers. For example, 68% in gastric cancer (66), 57% in esophageal cancer (67), 45% in osteosarcoma (68), 34% in breast cancer (69), and 30% in lung cancer (70).

Second, alloreactive or xenoreactive T cells also attack HLA-I-expressing stromal cells such as carcinoma-associated fibroblasts, angiogenic vascular cells (71) and myeloid-derived suppressor cells (72) that play important roles in supporting tumor growth and in creating an immunosuppressive tumor microenvironment. Stromal cells have been found to strongly and uniformly express HLA-I even when tumor cells are HLA-negative (73-75). These two features make it possible to use tumor-activated alloreactive or xenoreactive T cells to treat tumors with a low percentage of tumor antigen-expressing cells that may be considered unsuitable for CAR T cells. In this sense, tumor antigen-expressing cells not only serve as targets, but also designate the whole tumor for attacks by therapeutic T cells.

Third, since the sources of T cells are healthy donors, tumor-activated alloreactive T cells that recognize certain popular HLA alleles or haplotypes may be produced in large quantities, cryo-preserved and offered as off-the-shelf products. T cell products with alloreactivities to each of the patient's HLA alleles can be selected, combined and administered for treatment. This will lower cost and enable repeated administration for better efficacy.

Taken together, tumor-activated alloreactive or xenoreactive T cells have the potential to be more effective for a broader range of tumors than CAR T cells.

The T cells are administered to a subject in need of treatment for a cellular proliferative disorder, including but not limited to, cancer. The T cells may be administered either alone, or as a pharmaceutical composition in combination with one or more pharmaceutically acceptable carriers, diluents or excipients and/or with other components, such as cytokines or other cell populations. Such compositions may comprise pharmaceutically acceptable buffers such as neutral buffered saline, phosphate buffered saline and the like; pharmaceutically acceptable carbohydrates such as glucose, mannose, sucrose or dextrans, mannitol; proteins; polypeptides or amino acids such as glycine; pharmaceutically acceptable antioxidants; pharmaceutically acceptable chelating agents such as EDTA or glutathione; pharmaceutically acceptable adjuvants (e.g., aluminum hydroxide); and pharmaceutically acceptable preservatives. Compositions are preferably formulated for intravenous administration.

Cancers that may be treated or prevented according to the present disclosure include a broad range of tumor types, including but not limited to: ovarian cancer, cervical cancer, breast cancer, prostate cancer, testicular cancer, lung cancer, renal cancer, colorectal cancer, skin cancer, brain cancer, and tumors that may arise from hematological malignancies such as leukemias, including acute myeloid leukemia (AML), chronic myeloid leukemia (CIVIL), acute lymphoid leukemia and chronic lymphoid leukemia. More particularly, cancers that may be treated by the compounds, compositions and methods of the disclosure include, but are not limited to, the following: cardiac cancers, lung cancers, gastrointestinal cancers, genitourinary tract cancers, liver cancers, bone cancers, nervous system cancers, gynecological cancers, hematologic cancers, skin cancers, and adrenal gland cancers.

Cancers may comprise solid tumors that may or may not be metastatic. Cancers may also occur as a diffuse tissue. Thus, the term "tumor cell," as provided herein, includes a cell afflicted by any one of the above identified disorders.

The T cells or pharmaceutical composition thereof may be administered by a route that results in the effective delivery of an effective amount of cells to the patient for pharmacological effect. Administration is typically parenteral. Intravenous administration is the preferred route, using infusion techniques that are commonly known in immunotherapy (see, e.g., Rosenberg et al., *New Eng. J. Med.* 319: 1676, 1988). The quantity of T cells and frequency of administration are determined by such factors as the condition of the patient, and the type and severity of the patient's disease, although appropriate dosages may be determined by clinical trials. An "effective amount" is determined by a physician with consideration of individual differences in age, weight, disease state, and disease severity of the patient. Generally, the amount of T cells given in a single dosage will range from about $10^6$ to $10^9$ cells/kg body weight, including all integer values within those ranges. The T cells may be administered multiple times at these dosages. The optimal dosage and treatment regime for a particular patient can readily be determined by one skilled in the art of medicine by monitoring the patient for signs of disease and adjusting the treatment accordingly.

The T cells or composition comprising the T cells compositions may be provided in a pharmaceutical pack or kit comprising one or more containers or compartments filled with one or more compositions. Optionally associated with such container(s) is a notice in the form prescribed by a governmental agency regulating the manufacture, use or sale of pharmaceuticals or biological products, which notice reflects approval by the agency of manufacture, use or sale for human administration. Also optionally included with such container(s) are instructions for carrying out the methods of the disclosure.

The instructional material may comprise a publication, a recording, a diagram, or any other medium of expression which can be used to communicate the usefulness of the method. The package insert may comprise text housed in any physical medium, e.g., paper, cardboard, film, or may be housed in an electronic medium such as a diskette, chip, memory stick or other electronic storage form. The instructional material of the kit of the disclosure may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

EXEMPLARY EMBODIMENTS

Among the embodiments provided herein are:

Embodiment 1. A method for producing tumor-activated alloreactive or xenoreactive T cells, said method comprising:

a) selecting a sample of T cells from an HLA-mismatched donor individual, or from a donor animal;

b) optionally stimulating the sample of T cells to proliferate;

c) abrogating the expression or function of at least one molecule necessary for TCR signaling and T cell activation in the T cells to render the T cells activation-incompetent; and d) modifying the T cells to (i) express a recombinant receptor molecule that specifically binds to a target molecule enriched on or in at least one of tumor cells, tumor microenvironment, and a tissue with blood cancer cell accumulation, wherein binding of the recombinant receptor with the target molecule releases or activates a transcription activator; and (ii) introduce an expression cassette that enables the transcription activator in (i) to drive the expression of the molecule abrogated in c), wherein step c) is performed before step d), step d) is performed before step c), or steps c) and d) are performed at the same time, and wherein binding of the recombinant receptor with the target molecule restores the expression or function of the abrogated molecule, and thereby restores the ability of the T cells to activate through antigen recognition by TCR, thereby producing tumor-activated alloreactive or xeno-reactive T cells.

Embodiment 2. The method of Embodiment 1, wherein step b) is not performed.

Embodiment 3. The method of Embodiment 1, wherein step b) is performed.

Embodiment 4. The method of any one of Embodiments 1 to 3, wherein step d) is carried out before step c).

Embodiment 5. The method of any one of Embodiments 1 to 3, wherein step c) is carried out before step d).

Embodiment 6. The method of any one of Embodiments 1 to 4, wherein steps c) and d) are performed at the same time.

Embodiment 7. The method of any one of Embodiments 4 to 6, wherein the T cell stimulation step comprises culturing donor T cells with antibodies specific for CD3 and CD28.

Embodiment 8. The method of any one of Embodiments 1 to 7, wherein the sample of T cells is from a donor individual, and wherein the donor individual has at least one HLA allele mismatch relative to an intended recipient and the at least one HLA allele mismatch is located in a locus selected from the group consisting of: HLA-A, HLA-B, HLA-C, HLA-DRB1, HLA-DQA1, HLA-DQB1, HLA-DPA1 and HLA-DPB1, thereby producing tumor-activated alloreactive T cells.

Embodiment 9. The method of any one of Embodiments 1-8, wherein step b) comprises co-culturing donor T cells with cells from an intended recipient.

Embodiment 10. The method of Embodiment 9, where the cells from the intended recipient are peripheral blood mononuclear cells, dendritic cells, tumor cells, or a mixture of thereof.

Embodiment 11. The method of Embodiment 9 and 10, where donor T cells are co-cultured with dendritic cells pulsed with lysate of tumor cells isolated from the patient or pulsed with the lysate of a tumor cell line derived from a tumor of the same type from a different individual.

Embodiment 12. The method of any one of Embodiments 1-8, wherein step b) comprises co-culturing donor T cells with cells from a second donor that (i) has at least one HLA allele matched with the intended recipient, and (ii) is mismatched with the T cell donor.

Embodiment 13. The method of Embodiment 12, where the cells from the second donor are peripheral blood mononuclear cells, dendritic cells, tumor cells, or a mixture of thereof.

Embodiment 14. The method of any one of Embodiments 1-8, wherein step b) comprises co-culturing donor T cells with a cell line expressing a least one HLA allele of the intended recipient.

Embodiment 15. The method of any one of Embodiments 9 to 14, the cells co-cultured with the donor T cells are treated with radiation or chemicals to block cell proliferation. Embodiment 16. The method of any one of Embodiments 1-8, wherein step b) comprises co-culturing donor T cells with an artificial surface.

Embodiment 17. The method of Embodiment 16, wherein the artificial surface is a plastic coated with at least one protein encoded by at least one HLA allele of the intended recipient.

Embodiment 18. The method of any one of Embodiments 1 to 17, wherein step c) comprises abrogating the expression of at least one protein critical for TCR signaling and T cell activation by disrupting the gene encoding the protein.

Embodiment 19. The method of Embodiment 18, wherein disrupting the gene uses a gene editing technology chosen from CRISPR-Cas, a transcription activator-like effector nuclease (TALEN), megaTALS, a zinc-finger nuclease, or a homing endonuclease.

Embodiment 20. The method of any one of Embodiments 1 to 19, wherein the at least one molecule necessary for TCR signaling and T cell activation is a cell surface molecule chosen from CD3ε, CD3ζ, CD3γ, CD3δ, CD4, CD8α, CD8β, LAT, TRIM, CD45, CD28, LFA-1, CD2, CD54, CD52, CD148, and CD58.

Embodiment 21. The method of any one of Embodiments 1 to 19, wherein the at least one molecule necessary for TCR signaling and T cell activation is an intracellular signaling molecule chosen from Lck, Zap70, calcineurin, PI3K, Fyn, PLCγ, NFAT, SLP76, PKCθ, NFκB, AKT, and PDK1.

Embodiment 22. The method of any one Embodiments 1 to 21, wherein the activation-incompetent T cells of step c) are purified by first staining the cells using antibodies specific for the surface molecules, and then isolating the cells lacking antibody binding by flow cytometry, magnetic beads, and/or purification columns.

Embodiment 23. The method of any one Embodiments 1 to 21, wherein the activation-incompetent T cells of step c) are purified by using a live cell-specific DNA imaging technique.

Embodiment 24. The method of Embodiment 23, wherein the live cell-specific DNA imaging technique is CRISPR LiveFish.

Embodiment 25. The method of any one of Embodiments 1 to 21, wherein the activation-incompetent T cells of step c) are purified by selecting T cells unable to activate and proliferate after further stimulation through TCR.

Embodiment 26. The method of any one of Embodiments 1 to 25, wherein step d) comprises introducing a nucleic acid encoding a tumor-sensing receptor into T cells using, for instance, lentiviral vectors, retroviral vectors, or transposon vectors such as Sleeping Beauty and piggyBac.

Embodiment 27. The method of Embodiment 26, wherein the tumor-sensing receptor comprises (i) an extracellular domain that binds directly or indirectly to a target molecule enriched on or in at least one of tumor cells, tumor microenvironment, and tissues with blood cancer cell accumulation; and (ii) an intracellular domain that activates or releases a transcription activator in response to extracellular domain binding to the target molecule.

Embodiment 28. The method of any one of Embodiments 1 to 27, wherein the target molecule is enriched on tumor cells and/or in the tumor microenvironment and is chosen from CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, FAP, fibronectin extra domain-B, folate receptor 1, GD2, GD3 ganglioside, glycoprotein 75, GPNMB, HGF, human scatter factor receptor kinase, IGF-1 receptor, IGF-I, IgG1, Ll-CAM, IL-13, IL-6, insulin-like growth factor I receptor, integrin αvβ3, MORAb-009, MS4A1, MUC1, mucin CanAg, N-glycolylneuraminic acid, NPC-IC, PDGF-Ra, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, mesothelin, NKG2D, CD147, NKR2, B7H3, and vimentin.

Embodiment 29. The method of any one of Embodiments 1 to 27, wherein the target molecule is enriched in a tissue with blood cancer cell accumulation, and wherein the tissue is lymphoid and/or bone marrow tissue.

Embodiment 30. The method of Embodiment 29, wherein the target molecule is chosen from CD45, CD19, CD20, CD4, CD8, CD2, CCR4, CD58, CD28, CD23, CD69, CD25, CD33, CD123 and CCL-1.

Embodiment 31. The method of any one of Embodiments 27 to 30, wherein the extracellular domain of the tumor-sensing receptor is a single chain variable fragment (scFv), a Fab fragment, a designed ankyrin repeat protein (DARPin), a TCR, a nanobody, a Fc receptor, a growth factor receptor, a chemokine receptor, or a hormone receptor.

Embodiment 32. The method of any one of Embodiments 27 to 30, wherein the tumor-sensing receptor is a version of the Synthetic Notch (SynNotch), Modular Extracellular Sensor Architecture (MESA), or Tango technology, wherein a transcription activator is released from the intracellular domain of the receptor in response to extracellular domain binding to the target molecule.

Embodiment 33. The method of any one of Embodiments 27 to 30, wherein the tumor-sensing receptor is a chimeric antigen receptor, wherein a downstream transcription factor is activated through signaling pathways activated in response to extracellular domain binding to the target molecule.

Embodiment 34. The method of any one of Embodiments 26 to 33, the nucleic acid comprises an expression cassette comprising a transcription control element operably linked to a DNA sequence encoding a functional copy of the at least one molecule necessary for TCR signaling and T cell activation abrogated in step c), wherein binding of a transcription activator activates and/or releases from the tumor-sensing receptor to the transcription control element activates transcription of the encoded functional copy of the at least one molecule necessary for TCR signaling and T cell activation.

Embodiment 35. The method of Embodiment 34, wherein the transcription control element is bound by a transcription activator selected from the group consisting of Gal4-VP64, Notch, tet transactivator, NFAT, AP-1, NFκB/Rel, NR4A1 (Nur77), T-Bet, IRF4, STATs and eomesodermin (Eomes).

Embodiment 36. The method of any one of Embodiments 1 to 35, wherein the potency and specificity of the tumor-activated alloreactive or xenoreactive T cells are regulated by controlling the affinity, specificity and expression level of tumor-sensing receptors or controlling the mRNA or protein stability of the critical molecule for T cell activation.

Embodiment 37. The method of any one of Embodiments 1 to 36, further comprising modifying the T cells to reduce the potential of being detected and eliminated through HvG by the patient's immune system.

Embodiment 38. The method of Embodiment 37, wherein modifying the T cells comprises abrogating T cell expression of HLA alleles mismatched with the recipient by disrupting the genes encoding HLA class I α heavy chain.

Embodiment 39. The method of Embodiment 38, wherein disrupting the genes encoding the HLA class I α heavy chain uses a gene editing technology chosen from CRISPR-Cas, a transcription activator-like effector nuclease (TALEN), megaTALS, a zinc-finger nuclease, or a homing endonuclease.

Embodiment 40. The method of Embodiment 37, wherein modifying the T cells comprises abrogating T cell expression of all HLA class Ion cell surface by disrupting the genes encoding beta-2-microglobulin ((32M) thereby.

Embodiment 41. The method of Embodiment 40, wherein disrupting the genes encoding beta-2-microglobulin uses a gene editing technology chosen from CRISPR-Cas, a transcription activator-like effector nuclease (TALEN), megaTALS, a zinc-finger nuclease, or a homing endonuclease, and further comprising introduction of HLA-G or HLA-E α chain fused with β2M using a non-viral or viral vector.

Embodiment 42. The method of any one of Embodiments 1 to 41, further comprising cryopreserving the tumor-activated T cells for later use.

Embodiment 43. A method of treating cancer in a patient by administering T cells prepared by the method of any one of Embodiments 1 to 42.

Embodiment 44. The method of Embodiment 43, wherein T cells generated from different donors or using different stimulations are administered to the same patient.

Embodiment 45. The method of Embodiment 43 or Embodiment 44, wherein prior to the administration of the T cells, the patient is conditioned with IFNγ (interferon gamma) to upregulate the expression of HLA on tumor cells and stromal cells.

Embodiment 46. The method of Embodiment 43 or Embodiment 44, wherein prior to the administration of the T cells, the patient is conditioned with lymphodepleting radiation or chemotherapy agent to suppress the immune system.

Embodiment 47. A genetically modified T cell (or a population thereof) comprising:

(i) genetic disruption of expression of at least one endogenous gene encoding a molecule necessary for TCR signaling and T cell activation, (ii) an exogenous nucleotide sequence encoding a tumor-sensing receptor that releases or activates a transcription activator in response to direct or indirect binding to molecules enriched on tumor cells, in the tumor microenvironment or in tissues with blood cancer cell accumulation, and (iii) an exogenous nucleotide sequence comprising an expression cassette that expresses a copy of the disrupted endogenous gene of (i) in response to the released or activated transcription activator of (ii).

Embodiment 48. The genetically modified T cell of Embodiment 47, wherein the at least one disrupted endogenous gene encoding a molecule necessary for TCR signaling and T cell activation encodes a transmembrane protein selected from CD3ε, CD3ζ, CD3γ, CD3δ, CD4, CD8α, CD8β, LAT, TRIM, CD45, CD28, LFA-1, CD2, CD54, CD52, CD148, and CD58, or encodes an intracellular signaling molecule chosen from Lck, Zap70, calcineurin, PI3K, Fyn, PLCγ, SLP76, PKCθ, AKT, and PDK1.

Embodiment 49. The genetically modified T cell of Embodiment 47 or Embodiment 48, wherein the tumor-sensing receptor comprises (i) an extracellular domain that binds directly or indirectly to a target molecule enriched on or in at least one of tumor cells, tumor microenvironment, and tissues with blood cancer cell accumulation; and (ii) an intracellular domain that activates or releases a transcription activator in response to extracellular domain binding to the target molecule.

Embodiment 50. The genetically modified T cell of Embodiment 49, wherein the tumor-sensing receptor is Synthetic Notch (SynNotch) receptor, a Modular Extracellular Sensor Architecture (MESA) receptor, or a Tango receptor.

Embodiment 51. The genetically modified T cell of Embodiment 49 or Embodiment 50, wherein the target molecule is enriched on tumor cells and/or in the tumor microenvironment and is chosen from CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, FAP, fibronectin extra domain-B, folate receptor 1, GD2, GD3 ganglioside, glycoprotein 75, GPNMB, HGF, human scatter factor receptor kinase, IGF-1 receptor, IGF-I, IgG1, L1-CAM, IL-13, IL-6, insulin-like growth factor I receptor, integrin αvβ3, MORAb-009, MS4A1, MUC1, mucin CanAg, N-glycolylneuraminic acid, NPC-IC, PDGF-Ra, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, mesothelin, NKG2D, CD147, NKR2, B7H3, and vimentin.

Embodiment 52. The genetically modified T cell of Embodiment 49 or Embodiment 50, wherein the target molecule is enriched in a tissue with blood cancer cell accumulation, and wherein the tissue is lymphoid and/or bone marrow tissue.

Embodiment 53. The genetically modified T cell of Embodiment 52, wherein the target molecule is chosen from CD45, CD19, CD20, CD4, CD8, CD2, CCR4, CD58, CD28, CD23, CD69, CD25, CD33, CD123 and CCL-1.

Embodiment 54. The genetically modified T cell of any one of Embodiments 49 to 53, wherein the extracellular domain of the tumor-sensing receptor is a single chain variable fragment (scFv), a Fab fragment, a designed ankyrin repeat protein (DARPin), a TCR, a nanobody, a Fc receptor, a growth factor receptor, a chemokine receptor, or a hormone receptor.

Embodiment 55. The genetically modified T cell of Embodiment 47 or Embodiment 49 wherein the tumor-sensing receptor is a chimeric antigen receptor, wherein a downstream transcription factor is activated through signaling pathways activated in response to extracellular domain binding to the target molecule.

Embodiment 56. The genetically modified T cell of any one of Embodiments 47 to 55, wherein the transcription control element driving expression of the copy of the disrupted endogenous gene is bound by a transcription activator selected from the group consisting of Gal4-VP64, Notch, tet transactivator, NFAT, AP-1, NFκB/Rel, NR4A1 (Nur77), T-Bet, IRF4, STATs and eomesodermin (Eomes).

Embodiment 57. A pharmaceutical composition comprising an effective amount of genetically modified T cells of any one of Embodiments 47 to 56 and a pharmaceutically acceptable carrier.

Embodiment 58. A kit comprising genetically modified T cells of any one of Embodiments 47 to 56 and instructional material for the use of the cells in a therapeutic method.

Embodiment 59. A method of treating cancer in a patient by administering T cells of any one of Embodiments 47 to 56 or the pharmaceutical composition of Embodiment 56.

Embodiment 60. The method of Embodiment 59, wherein T cells generated from different donors or using different stimulations are administered to the same patient.

Embodiment 61. The method of Embodiment 59 or Embodiment 60, wherein prior to the administration of the T cells, the patient is conditioned with INFγ to upregulate the expression of HLA on tumor cells and stromal cells.

Embodiment 62. The method of Embodiment 59 or Embodiment 60, wherein prior to the administration of the T cells, the patient is conditioned with lymphodepleting radiation or chemotherapy agent to suppress the immune system.

Embodiment 63. Use of a genetically modified T cell according to any one of Embodiments 47 to 56 in the treatment of cancer in a patient in need thereof.

Embodiment 64. Use of a genetically modified T cell according to any one of Embodiments 47 to 56 in the manufacture of a medicament to treat cancer.

Further embodiments provided herein are:

Embodiment P1: A method for producing tumor-activated alloreactive or xenoreactive T cells, said method comprising:

a. selecting a sample of T cells from an HLA-mismatched donor individual or from a donor animal;
b. stimulating the said T cells to drive the cells into cell cycle (proliferate);

c. generating activation-incompetent T cells by abrogating the expression or function of at least one molecule critical for TCR signaling and T cell activation; and d. generating tumor-activated alloreactive or xenoreactive T cells by introducing a mechanism that recognizes molecules enriched on tumor cells or in the tumor microenvironment, and as the result of the recognition, restores the expression or function of the molecule abrogated in the previous step, thus restores the ability of T cells to activate through antigen recognition by TCR.

Embodiment P2: The method of Embodiment P1, wherein steps c) and d) are carried out at the same time or in reverse order.

Embodiment P3: The method of Embodiment P1, wherein T cell samples are from donor individuals with HLA genes mismatched with the patient at a single locus or at multiple loci selected from the group consisting of: HLA-A, HLA-B, HLA-C, HLA-DRB1, HLA-DQA1, HLA-DQB1, HLA-DPA1 and HLA-DPB1 locus.

Embodiment P4: The method of Embodiment P1, wherein the T cell stimulation step comprises culturing donor T cells with antibodies specific for CD3 and CD28.

Embodiment P5: The method of Embodiment P1, wherein the T cell stimulation step comprises co-culturing donor T cells with cells from the patient, including peripheral blood mononuclear cells, dendritic cells, tumor cells, or a mixture of these cells.

Embodiment P6: The method of Embodiment P1, wherein the T cell stimulation step comprises culturing donor T cells with peripheral blood mononuclear cells, dendritic cells, or a mixture of these cells from another donor who has at least one HLA allele matched with the patient but mismatched with the T cell donor.

Embodiment P7: The method of Embodiment P1, wherein the T cell stimulation step comprises culturing donor T cells with cell lines expressing at least one HLA allele of the patient.

Embodiment P8: The method of Embodiment P1, wherein the T cell stimulation step comprises culturing donor T cells with artificial surfaces such as plastics coated with proteins encoded by at least one HLA allele of the patient.

Embodiment P9: The method of Embodiments P5, P6, or P7, wherein the stimulator cells (not the T cells) are treated with radiation or chemicals to block cell proliferation.

Embodiment P10: The method of Embodiment P1, wherein the step of generating activation-incompetent T cells comprises abrogating the expression of at least one protein critical for TCR signaling and T cell activation by disrupting the gene encoding the protein using gene-editing technologies including CRISPR-Cas, transcription activator-like effector nuclease (TALENs), megaTALS, zinc-finger nucleases, and homing endonucleases.

Embodiment P11: The method of Embodiment P10, wherein the proteins critical for TCR signaling and T cell activation include cell surface molecules CD3ε, CD3ζ, CD3γ, CD3δ, CD4, CD8α, CD8β, LAT, TRIM, CD45, CD28, LFA-1, CD2, CD54, CD52, CD148, and CD58, and intracellular signaling molecules Lck, Zap70, calcineurin, PI3K, Fyn, PLCγ, NFAT, SLP76, PKCθ, NFκB, AKT, and PDK1.

Embodiment P12: The method of Embodiment P10, wherein T cells with abrogated expression of surface molecules are purified by staining the cells using antibodies specific for the surface molecules, followed by isolation of cells without antibody binding using technologies including flow cytometry, magnetic beads, and purification columns.

Embodiment P13: The method of Embodiment P10, wherein T cells with abrogated expression of intracellular signaling molecules are isolated using live cell specific DNA imaging techniques including CRISPR LiveFISH.

Embodiment P14: The method of Embodiment P10, wherein T cells with at least one molecule critical for TCR signaling and activation disrupted are purified based on the inability of the T cells to activate and proliferate after further stimulation through TCR.

Embodiment P15: The method of Embodiment P1, wherein the generating tumor-activated alloreactive or xenoreactive T cells step comprises introducing nucleic acids for a tumor-sensing receptor into T cells.

Embodiment P16: The method of Embodiment P15, wherein the tumor-sensing receptor comprises an extracellular domain that binds directly or indirectly to molecules enriched on tumor cells or in the tumor microenvironment and an intracellular domain that, in response to extracellular domain binding, activates or releases a transcription activator.

Embodiment P17: The method of Embodiment P16, wherein the extracellular domain of the tumor-sensing receptor is a single chain variable fragment (scFv), a Fab fragment, a designed ankyrin repeat protein (DARPin), a TCR, a nanobody, a Fc receptor, a growth factor receptor, a chemokine receptor, or a hormone receptor.

Embodiment P18: The method of Embodiment P15, where the tumor-sensing receptor is based on the Synthetic Notch (SynNotch), Modular Extracellular Sensor Architecture (MESA), or Tango technology.

Embodiment P19: The method of Embodiment P1, wherein the step of generating tumor-activated alloreactive or xenoreactive T cells comprises introducing nucleic acids for an expression cassette into T cells, wherein the expression cassette comprises a transcription control element operably linked to a DNA sequence that encodes the gene disrupted in Embodiment P10 and Embodiment P11, wherein binding of the transcription activator activated and/or released from the tumor-sensing receptor in Embodiment P16 to the transcription control element activates the transcription of the disrupted gene.

Embodiment P20: The method of Embodiment P1, wherein the potency and specificity of the tumor-activated alloreactive or xenoreactive T cells are regulated by controlling the affinity, specificity and expression level of tumor-sensing receptors or controlling the mRNA or protein stability of the critical molecule for T cell activation.

Embodiment P21: The method of Embodiment P1, wherein the tumor activated alloreactive or xenoreactive T cells are further modified to reduce the potential of being detected and eliminated through HvG by the patient's immune system.

Embodiment P22: The method of Embodiment P21 wherein T cell expression of HLA alleles mismatched with the patient are abrogated by disrupting the genes encoding HLA class I α heavy chain using gene-editing technologies including CRISPR-Cas, transcription activator-like effector nuclease (TALENs), megaTALS, zinc-finger nucleases, and homing endonucleases.

Embodiment P23: The method of Embodiment P21 wherein the expression of all HLA class I on cell surface is abrogated by disrupting the genes encoding β2M using gene-editing technologies, followed by the introduction of HLA-G or HLA-E α chain fused with β2M using non-viral or viral vectors.

Embodiment P24: The method of Embodiment P1, wherein the tumor-activated alloreactive or xenoreactive T cells are cryopreserved for later use.

Embodiment P25: A method of treating cancer in a patient by administering T cells prepared by the method of Embodiment 1.

Embodiment P26: The method of Embodiment P25, wherein T cells generated from different donors or using different stimulations are administered to the same patient.

Embodiment P27: The method of Embodiment P25, wherein prior to the administration of the T cells, the patient is conditioned with INFγ to upregulate the expression of HLA on tumor cells and stromal cells.

Embodiment P28: The method of Embodiment P25, wherein prior to the administration of the T cells, the patient is conditioned with lympho-depleting radiation or chemotherapy agent to suppress the immune system.

Embodiment P29: A genetically modified tumor-activated alloreactive or xenoreactive T cell.

Embodiment P30: The T cell of Embodiment P29, comprising a genetic modification to disrupt expression of at least one endogenous gene encoding a molecule that is critical for TCR signaling and T cell activation.

Embodiment P31: The T cell of Embodiment P30, wherein the at least one endogenous gene disrupted encodes a transmembrane protein or an intracellular signaling molecule.

Embodiment P32: The T cell of Embodiment P31, wherein the disrupted endogenous gene is a transmembrane protein selected from CD3ε, CD3ζ, CD3γ, CD3δ, CD4, CD8α, CD8β, LAT, TRIM, CD45, CD28, LFA-1, CD2, CD54, CD52, CD148, and CD58.

Embodiment P33: The T cell of Embodiment P31, wherein the disrupted endogenous gene is an intracellular signaling molecule selected from Lck, Zap70, calcineurin, PI3K, Fyn, PLCγ, NFAT, SLP76, PKCθ, NFκB, AKT, NcK and PDK1.

Embodiment P34: A pharmaceutical composition comprising an effective amount of genetically modified tumor-activated T cells of Embodiment P29 and a pharmaceutically acceptable carrier.

Embodiment P35: A method of treating cancer in a patient by administering genetically modified tumor-activated T cells of Embodiment P29.

Embodiment P36: The method of Embodiment P35, wherein T cells generated from different donors or stimulations are administered to the same patient.

Embodiment P37: The method of Embodiment P35, wherein prior to the administration of the T cells, the patient is conditioned with INFγ to upregulate the expression of HLA on tumor cells and stromal cells.

Embodiment P38: The method of Embodiment P35, wherein prior to the administration of the T cells, the patient is conditioned with lympho-depleting radiation or chemotherapy agent to suppress the immune system.

Embodiment P39: A kit comprising genetically modified tumor-activated T cells of Embodiment P29 and instructional material for the use of the cells in a therapeutic method.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: T Cell Alloreactivity to U266 Myeloma Cells

The cytotoxicity of alloreactive T cells to U266 myeloma cells was determined as followed. T cells from a healthy donor were activated with anti-CD3/CD28 beads for 72 hrs and expanded for additional 5 days in medium supplemented with 100 U/ml recombinant human IL2. $2.5\times10^5$ T cells were incubated with $2.5\times10^4$ U266 cells expressing luciferase at a 10:1 ratio for 16 hrs in the absence or presence of 10 μg/ml CD8-specific monoclonal antibody SK1. Luciferase activities in the remaining live U266-luciferase cells were determined using the Bright-Glo™ luciferase assay system (Promega, Madison, WI). The luciferase activities of $2.5\times10^4$ U266-luciferase cells cultured without T cells were determined as the maximum activity. Specific killing was calculated as {1−(sample activity)/(max activity)}×100.

Figure 3:
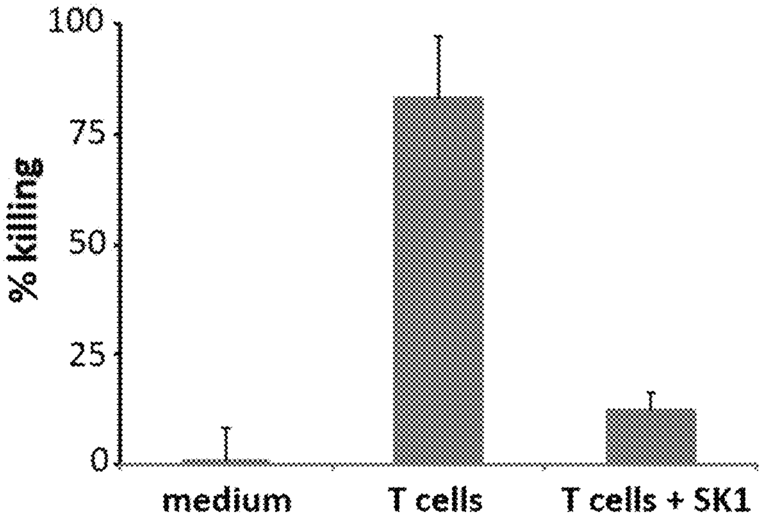
FIG. 3 depicts data for cytotoxicity of alloreactive T cells to U266 myeloma cells. SK1: CD8-specific monoclonal antibody SK1. % killing: specific killing calculated as [1−(sample activity)/(max activity)]×100. Data represents Mean±SD (n=3).

The data are shown in FIG. 3. U266, a cell line established from an IgE myeloma patient, expresses high levels of HLA class I (76). Co-culturing U266 cells with pre-activated HLA-I-mismatched primary human CD8+ T cells led to significant killing of U266 cells. The killing was largely inhibited by the anti-CD8 antibody SK1, which has been shown to effectively block T cell activation through TCR-HLA class I interaction, in which CD8 is critically involved (77, 78).

Example 2: Reduced TCR/CD3 Complex Expression on Mouse D10 T Cells after CD3ζ Knockout Using CRISPR-Cas9

The experiment was carried out as follows. CD3ζ is required for the assembly and cell surface expression of TCR/CD3 complex, which also consists of TCRα, TCRβ, CD3γ and CD3ε chains. Guide RNA (gRNA) designed to target the extracellular domain of mouse CD3ζ was synthesized using a GeneArt™ Precision gRNA Synthesis Kit (Invitrogen). The gRNA and Cas9 ribonucleoproteins (RNPs) were introduced into D10 cells using an electroporation-based Neon Transfection System (Invitrogen). Cells were stained with antibodies specific for TCRβ and CD3ε and analyzed using flow cytometry.

Figure 4:
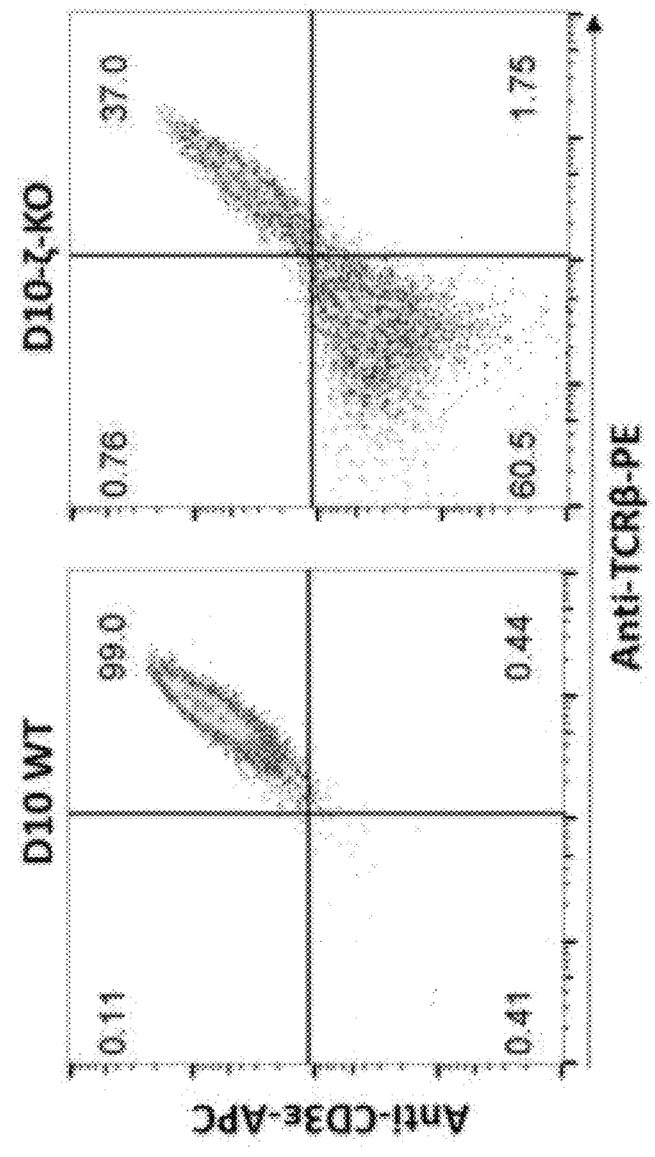
FIG. 4 depicts data for expression of TCRβ and CD3ε on modified D10 cells and wild type D10 cells.

The data are shown in FIG. 4. CD3ζ was knocked out in more than 60% of D10 cells, as indicated by the much lower surface expression levels of TCRβ and CD3ε.

Example 3: Non-Specific Primary T Cell Activation and Expansion Using Anti-CD3/CD28 Magnetic Beads Five hundred thousand (500,000) purified primary human CD8+ T cells were cultured with human T-activator CD3/CD28 Dynabeads (Life Technologies) at a 1:1 cell to bead ratio in a 48-well plate. The cells were cultured in OpTmizer culture medium (Thermo Fisher; CTS™ OpTmizer™ T cell Expansion SFM, 6 mM GlutaMAX™, and 2% CTS™

Immune Cell SR) supplemented with 10 ng/ml recombinant human IL2 (rhIL-2; R&D Systems). Beads were removed after 3 days of stimulation.

The T cells were maintained at $0.5\times10^6$/ml to $2\times10^6$/ml with change of medium and rhIL2 every 1 to 2 days.

Figure 5:
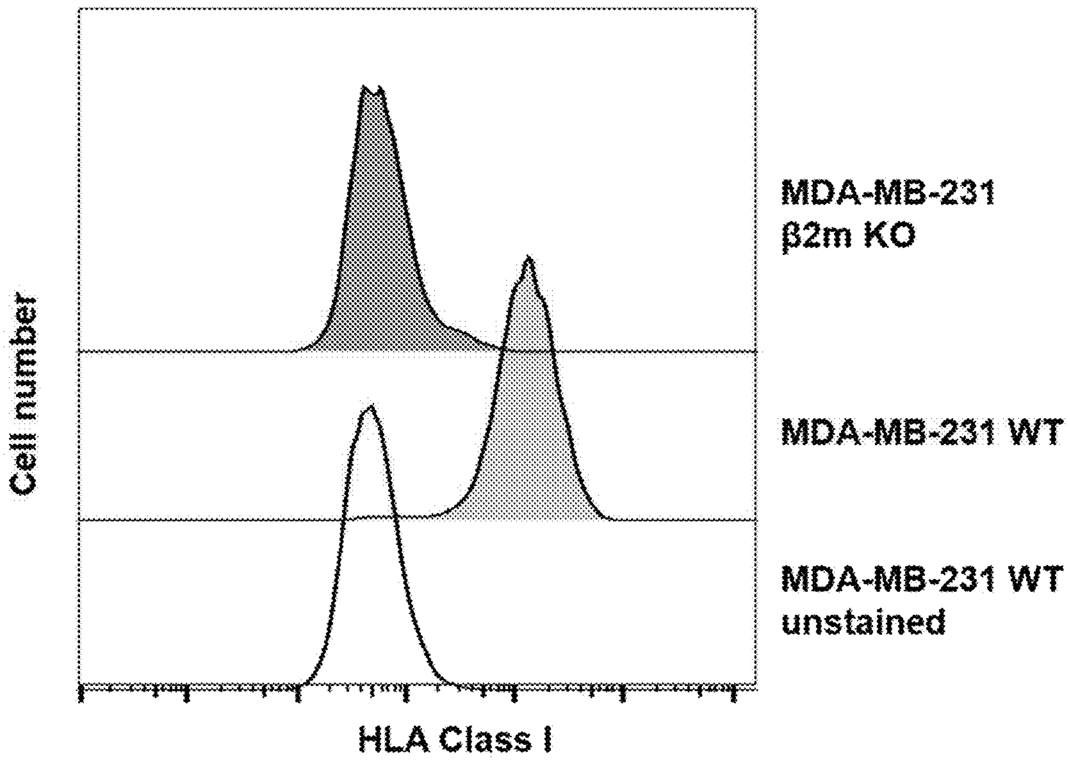
FIG. 5 depicts HLA-I expression on wild-type MDA-MB-231 cells and MDA-MB-231 cells with β2m knocked out. MDA-MB-231: human breast cancer cell line. β2m KO: beta 2 microglobulin knock out. WT: wild type. Cells were stained with FITC-labeled anti-HLA-I monoclonal antibody clone W6/32.

Example 4: Specific Stimulation and Expansion of Alloreactive T Cells Using the Human Breast Cancer Cell Line MDA-MB-231 Cell Line The human breast cancer cell line MDA-MB-231 (ATCC) expresses relatively high levels of HLA-I (A02:17; A02:01; B41:01; B40:02; C17:01; C02:02) (79). (FIG. 5, MDA-MB-231 WT). To generate a negative control without HLA-I expression, beta-2-microglobulin (β2m) was knocked out by transfecting the cells with *Streptococcus pyogenes* (S.p.) Cas9 nuclease V3 (IDT) and single guide RNA (sgRNA; IDT Hs.Cas9.B2M.1.AA; crRNA sequence: 5'-CGUGAGUAAACCUGAAUCUU-3' SEQ ID NO: 15) using a Neon Transfection System (ThermoFisher). MDA-MB-231 cells with β2m knocked out showed minimal levels of HLA-I expression (FIG. 5, MDA-MB-231 β2m KO).

To specifically stimulate and expand alloreactive T cells, $0.125\times10^6$ MDA-MB-231 cells were seeded in a 48 well plate and cultured overnight. $0.75\times10^6$ purified primary human CD8 T cells from a donor with mismatched HLA-I (A 34:02, A 68:02; B 07:02, B 57:03; C 07:01, C 07:02) were added and cultured in OpTmizer™ (Thermo Fisher Scientific) culture medium supplemented with 10 ng/ml rhIL-2 and 1 μg/ml Ultra-LEAF™ purified anti-CD28 monoclonal antibody (Biolegend, clone CD28.2). After 5 days of culture, T cells were moved to a flask and cultured at a density of $0.5\times10^6$ to $2\times10^6$ cells/ml.

Figures 6A, 6B:
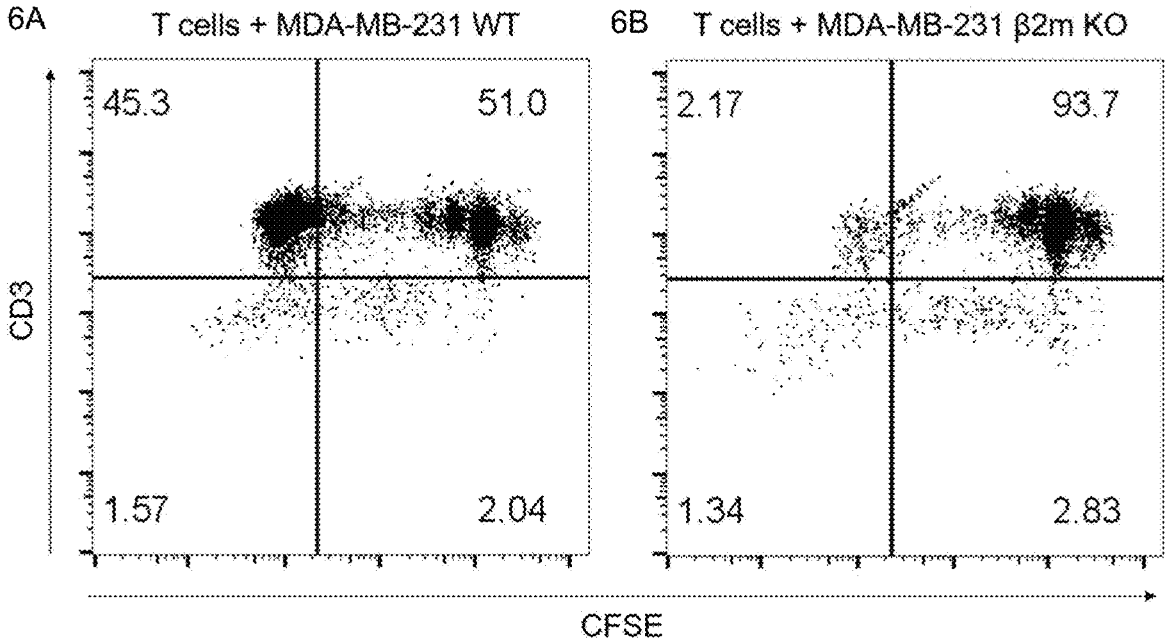
FIGS. 6A and 6B depict flow cytometry data for proliferation of T cells co-cultured with MDA-MB-231 cells (wild type in FIG. 6A or with beta 2 microglobulin knock out in FIG. 6B). MDA-MB-231: human breast cancer cell line. β2m KO: beta 2 microglobulin knock out. WT: wild type. CFSE: carboxyfluorescein diacetate succinimidyl ester.

The data are shown in FIGS. 6A and 6B. CFSE (carboxyfluorescein diacetate succinimidyl ester) labeled T cells proliferated rapidly when co-cultured with WT MDA cells but showed limited proliferation with MDA cells with HLA-I knocked out. See FIGS. 6A and 6B, respectively.

Example 5: Lentiviral Transduction of Primary Human T Cells to Introduce Anti-CD19 SynNotch and CD3ε Expression Cassette Lentiviral vectors for anti-CD19 SynNotch were packaged using the transfer vector pHR_PGK_antiCD19_synNotch_Gal4VP64 (Addgene Cat. #79125). The vector drives the expression of anti-CD19 SynNotch receptor downstream of a constitutively active PGK-1 promoter. The anti-CD19 SynNotch receptor comprises a N-terminal MycTag followed by a CD19-specific extracellular single chain variable fragment (scFv), a Notch core sequence including the transmembrane domain, and an intracellular domain containing a cleavable artificial transcription activator Gal4-VP64, which consists of a Gal4 DNA binding domain and a VP64 transcription activation domain (14, 55).

To prepare lentiviral vectors for the CD3ε expression cassette, the transfer vector pHR_Gal4UAS_IRES_mC_pGK_tBFP (Addgene #79123) (14, 55) was modified by inserting a human CD3ε coding sequence downstream the Gal4 binding sites and removing the IRES-mCherry sequence. The human CD3ε coding sequence was codon optimized so that the target-specific sequence of the gRNA for CD3ε knockout no longer functions through recognizing the CD3ε coding sequence in the cassette and working with Cas9 to cleave it. The resulting transfer vector encodes a Gal4-CD3-PKG-BFP cassette (SEQ ID NO: 1) in which CD3ε expression is controlled by the Gal4 binding sequence and the expression of blue fluorescence protein (BFP) is driven by a constitutively active PGK-1 promotor (FIG. 15). BFP expression therefore serves as a marker for the presence the cassette in transduced cells.

Lentiviral vectors were packaged in Lenti-X 293T cells (Takara) and concentrated 100-fold using the Lentivirus Precipitation Solution (ALSTEM). To transduce T cells, 50 μl concentrated lentiviral vectors each for anti-CD19 SynNotch and Gal4-CD3-PKG-BFP cassette were added to T cells stimulated by anti-CD3/CD28 beads or MDA-MB-231 cells at day 1 post stimulation. After 24 hours of incubation in the presence of 10 μg/ml protamine, media were changed to dilute protamine sulfate and 10 ng/ml rhIL-2 was added. For co-culture with MDA-MB-231 cells, anti-human CD28 antibody (Biolegend, clone CD28.2) was added to 1 μg/ml. Anti-CD19 synNotch expression was analyzed by staining with PE-conjugated anti-MycTag (Cell Signaling Technology, clone 9B11). The presence of CD3ε expression cassette in T cells was marked by the expression of BFP.

Figures 7A, 7B, 7C:
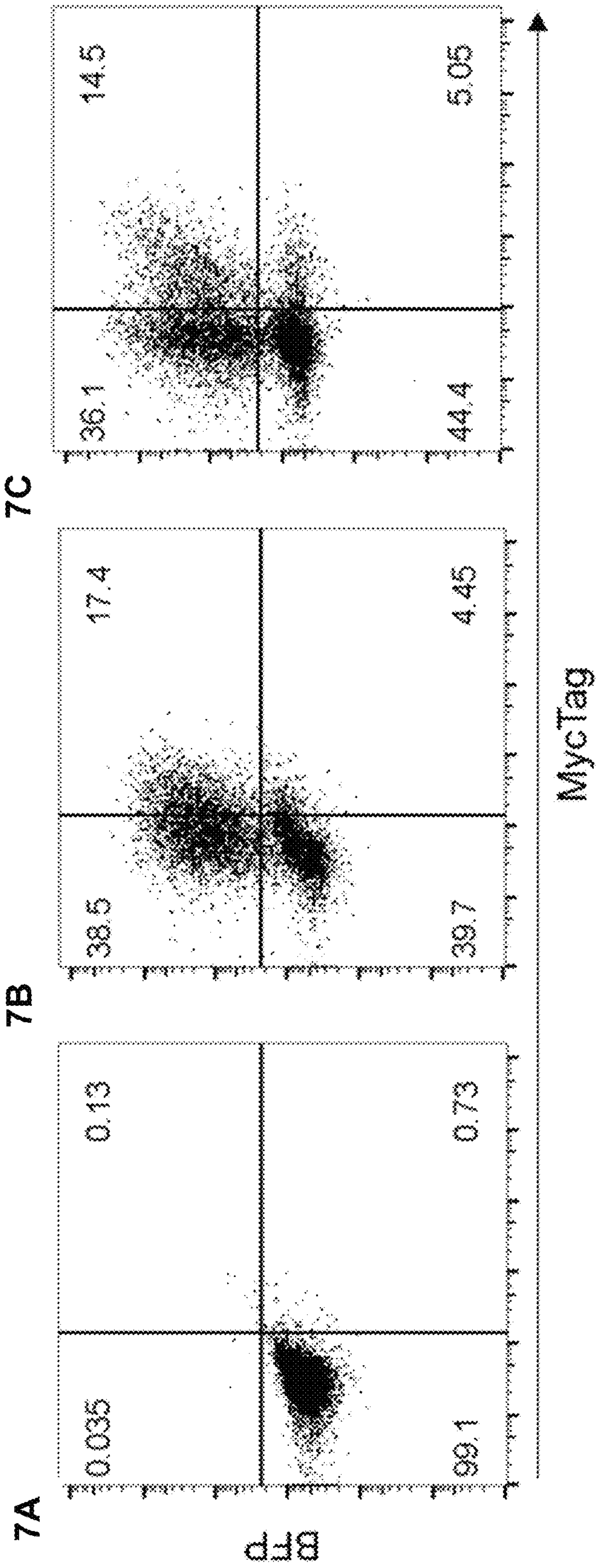
FIGS. 7A-7C depicts flow cytometry data for CD3ε and anti-CD19 SynNotch expression in primary human CD8+ T cells genetically modified to comprise anti-CD19 SynNotch receptor and CD3ε expression cassettes. The anti-CD19 SynNotch receptor contains a cleavable artificial transcription activator Gal4-VP64; expression of the anti-CD19 SynNotch receptor is driven by a constitutively active PGK-1 promoter. The CD3ε expression cassette includes a blue fluorescence protein (BFP)-encoding sequence driven by a constitutively active PGK-1 promoter. The genetically modified T cells were stimulated by co-culture with MDA-MB-231 cells; anti-human CD28 antibody was added to the co-culture with MDA-MB-231 cells. Anti-CD19 SynNotch expression was analyzed by staining with PE-conjugated anti-MycTag (Cell Signaling Technology, clone 9B11) (X-axis). The presence of CD3ε expression cassette in T cells were marked by the expression of blue fluorescence protein (BFP) (Y-axis).

As shown in FIGS. 7A and 7B, 7 days after the transduction of primary human CD8+ T cells stimulated with MDA-MB-231 cells, more than 50%, 20% and 17% of cells expressed the Gal4-CD3-PKG-BFP alone, anti-CD19 SynNotch alone, and both, respectively.

Figures 8A, 8B, 8C:
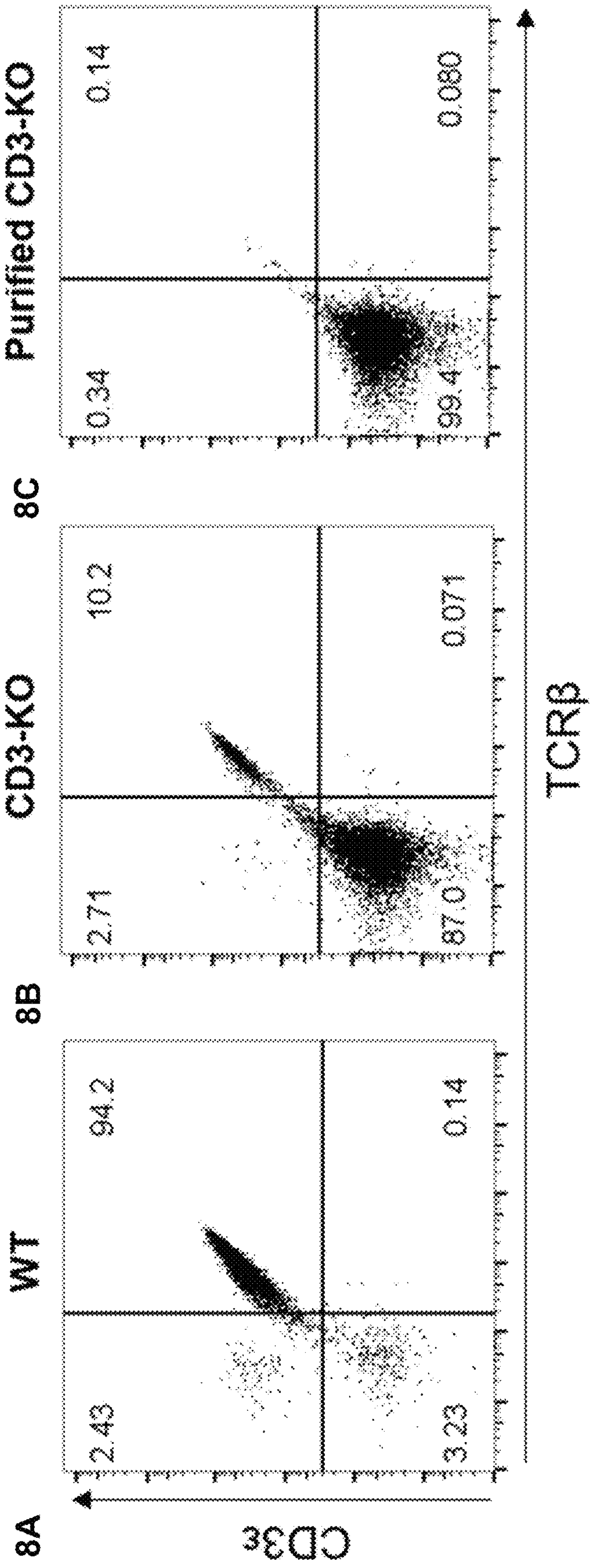
FIGS. 8A-8C depict flow cytometry data for CD3ε and TCRβ expression of human CD8+ T cell. CD3ε expression was knocked out (KO) in primary human CD8+ T cells using CRISPR-Cas9, and CD3ε knocked out (CD3-KO) cells were purified using magnetic separation.

Example 6: CD3ε Knockout (KO) Using CRISPR-Cas9 and Isolation Purification of CD3-KO Cells Using Magnetic Separation To knock out CD3ε expression, 4 to 5 days after stimulation with anti-CD3/CD28 beads or MDA-MB-231 cells, primary human CD8+ T cells were electroporated using the Neon Transfection System (ThermoFisher). Specifically, ribonucleoprotein (RNP) was formed by incubating 7.5 pmol of hCD3ε Alt-R CRISPR-Cas9 single guide RNA (sgRNA, IDT #Hs.Cas9.CD3E.1.AC, crRNA sequence: 5'-agggcaugtcaauauuacug-3'; SEQ ID NO: 16) and 7.5 pmol of Alt-R S.p Cas9 Nuclease V3 (IDT) in 5 μl Buffer R for 15 mins. The RNP was then mixed with $0.2\times10^6$ T cells in Buffer R, loaded into a 10 μl tip and electroporated using the program #24 (1600 v, 10 ms, 3 pulses). As shown in FIG. 8A and FIG. 8B, three days post electroporation, ~94% T cells were stained negative for both CD3ε and TCRβ, indicating efficient knockout of CD3ε and the intracellular retention of the TCR/CD3 complex. To purify the CD3-KO cells, the CD3+ T cells were removed using an EasySep Human CD3 Positive Selection Kit II (StemCell Technologies). The purity of CD-KO cells reached to more than 99% after two rounds of removal with the kit (FIG. 8C).

To determine whether the lack of CD3ε expression impacts the T cells' proliferation potential, CD3ε knockout was performed as described above but without removing CD3+ T cells and the mixed WT and CD3-KO T cells were cultured for 25 days.

Figure 9:
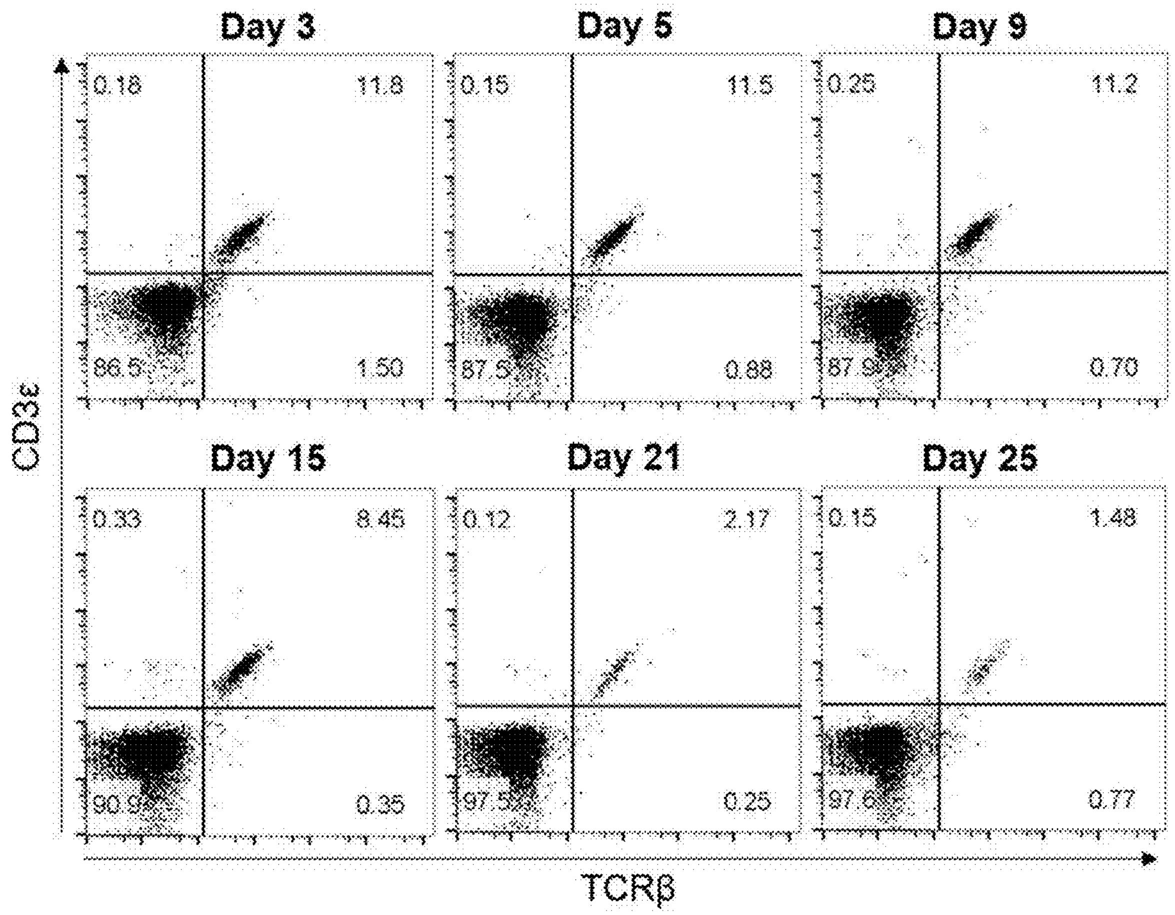
FIG. 9 depicts a time course of flow cytometry data assessing proliferation of T cells subjected to CD3ε knockout (CD3-KO cells). Primary human T cells were subjected to CD3ε knockout via CRISPR. After knockout, the $CD3^+$ T cells (i.e., wild type T cells) were not removed from the mixture. The mixed WT and CD3-KO T cells were cultured for 25 days and periodically assessed for CD3ε and TCRβ expression.

As shown in FIG. 9, the ratio of CD3-KO to WT T cells stayed relatively constant over time, indicating that CD3-KO T cells had the similar proliferation potential as WT T cells. As shown in FIG. 7C, CD3 knockout did not significantly impact the expression of SynNotch and expression cassette in transduced T cells.

Example 7: CD3 Knockout Abrogated T Cell Alloreactive Killing

To determine the cytotoxicity of alloreactive T cells and the impact of CD3 knockout, T cells from an HLA-mismatched donor (A29:02, A30:01; B35:01, B53:01; C04:01) were stimulated with MDA-MB-231 cells and electroporated to knock out CD3ε as in EXAMPLE 6. Wild type (WT; intact CD3ε) or purified CD3KO cells were co-cultured with MDA-MB-231 cells expressing firefly luciferase (MDA-MB-231-luci) at a 3:1 ratio for 6 hrs. MDA-MB-231-luci cells cultured alone were used as controls. The luciferase activities of the cultures were determined using the Bright-Glo reagent (Promega) and read on a Victor plate reader (PerkinElmer). The percentages of specific % killing were calculated as 100×[1−(luciferase activity of sample/luciferase activity of control)].

Figure 13:
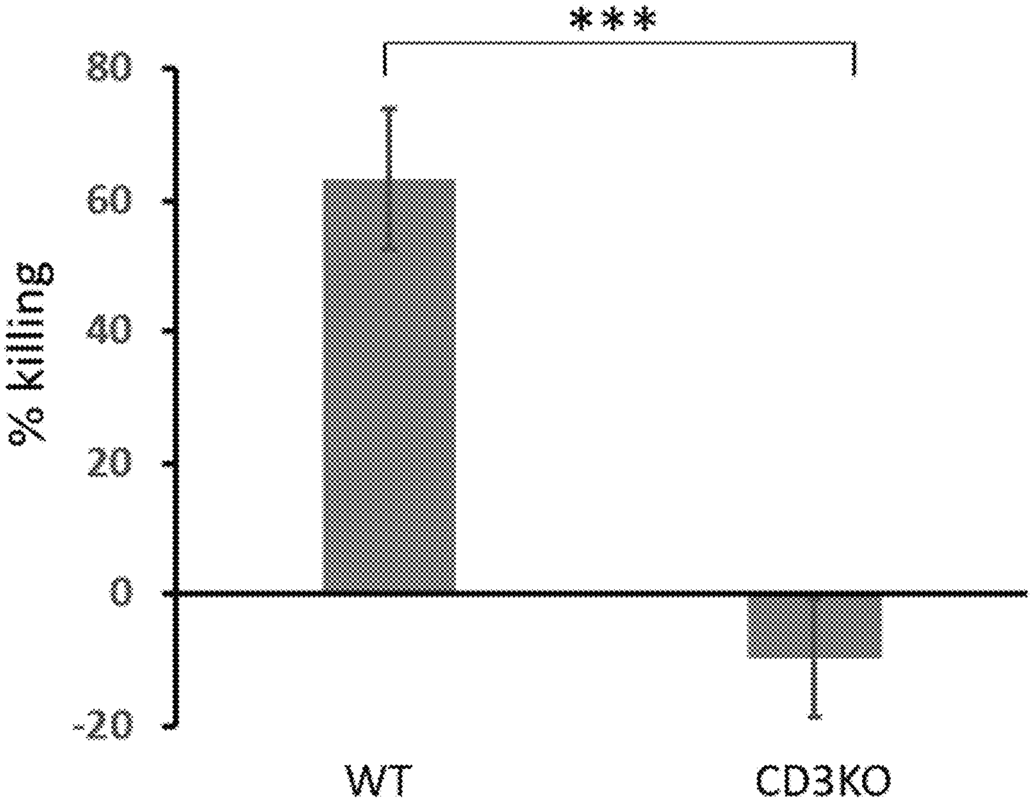
FIG. 13 depicts data for cytotoxicity of alloreactive wide type (WT) and CD3ε knockout (CD3KO) T cells to MDA-MB-231 cells. Data are represented as mean±SD (n=3). ***: P<0.001, Student's t-test.

As shown FIG. 13, the WT T cells showed >60% specific killing of MDA-MB-231 cells. In contrast, a negative percentage of specific killing was seen for CD3KO cells. The negative value was a result of slightly more luciferase activities in the co-cultured cells than in the control cells.

Figure 10:
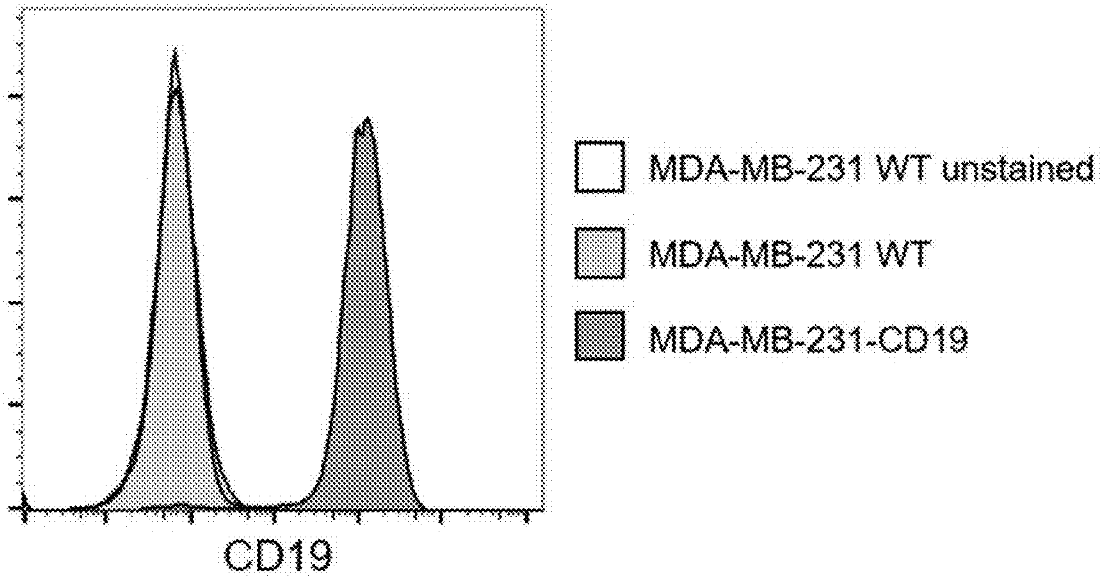
FIG. 10 depicts CD19 expression on wild type MDA-MB-231 cells (MDS-MG-231 WT) and modified MDA cells (MDA-MB-231-CD19).

Example 8: Engagement of Anti-CD19 SynNotch Restored CDR Expression on CD3-KO T Cells Expressing Anti-CD19 SynNotch and Gal4-CD3-PKG-BFP Cassette and Enabled the Cells to Activate in Response to Anti-CD3 Stimulation To generate CD3-KO T cells expressing anti-CD19 SynNotch and Gal4-CD3-PKG-BFP cassette (CD3KO-19SN-εCS T cells), primary human CD8+ T cells were stimulated with MDA-MB-231 cells, transduced with lentiviral vectors encoding the anti-CD19 SynNotch and Gal4-CD3-PKG-BFP cassette, electroporated to knockout CD3ε, and CD3-negative T cells were purified as described in EXAMPLES 4, 5 and 6. To test the cells' ability to restore CD3 expression and react to anti-CD3 stimulation, 200,000 CD3KO-19SN-εCS T cells were stimulated for 16 hours with 80,000 WT MDA-MB-231 cells or MDA-MB-231 cells expressing human CD19 (FIG. 10) in a 96-well tissue culture plate. The T cells were then transferred to a separate well containing anti-CD3/CD28 Dynabeads (Life Technologies) at a 1:1 bead to T cell ratio and incubated for 6 hours in the presence of monensin (Biolegend) and FITC-conjugated anti-human-CD107a antibody (Biolegend, clone H4A3). Beads were then removed, and the cells were fixed in 4% formaldehyde, permeabilized with permeabilization buffer (0.5% BSA, 0.1% saponin, in DPBS/azide), stained with anti-human-CD3 and anti-human-IFNγ (Biolegend clone 4S.B3) antibodies and analyzed using a NovoCyte Quanteon flow cytometer.

Figures 11A, 11B:
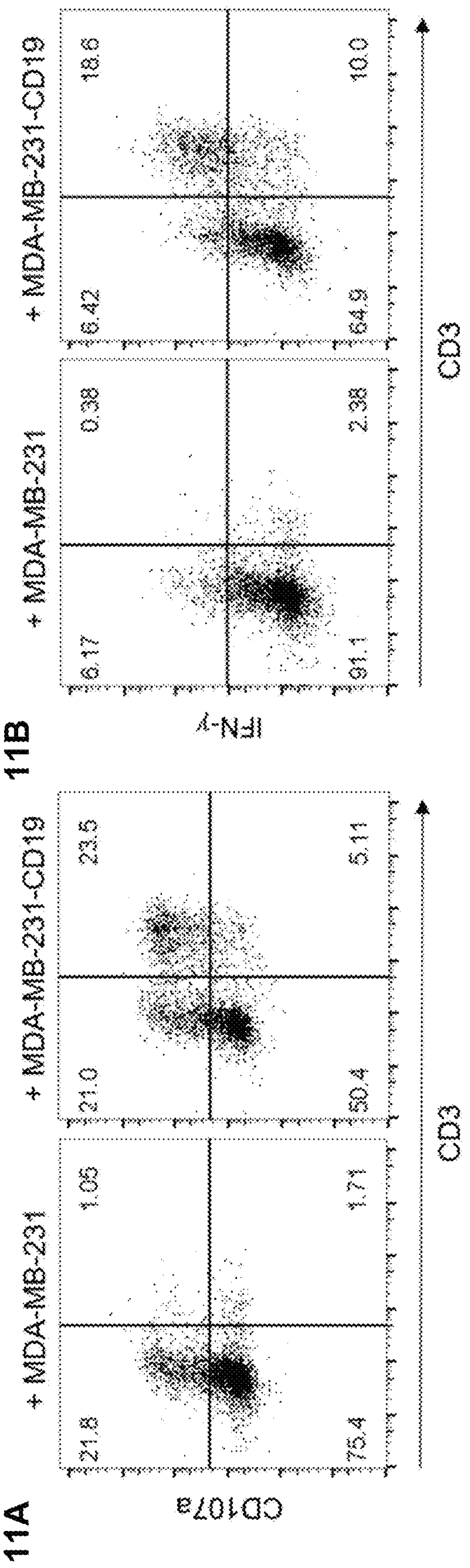
FIGS. 11A and 11B depict flow cytometry data illustrating engagement of anti-CD19 SynNotch restores CD3 expression on CD3KO-19SN-εCS T cells and enables the cells to activate in response to anti-CD3 antibody stimulation in terms of degranulation (CD107a) and IFNγ production (FIGS. 11A and 11 B respectively). Cells were gated on BFP+ population.

The data are shown in FIG. 11A significant number of BFP+CD3KO-19SN-εCS T cells restored CD3 expression in response to MDA-MB-231-CD19 cells but not to WT MDA-MB-231 cells. Among the T cells with restored CD3 expression, most degranulated as indicated by the positive CD107a staining (FIG. 11A) and produced IFNγ (FIG. 11B). The result demonstrated that engagement of anti-CD19 SynNotch on CD3KO-19SN-εCS T cells restored CD3 expression and the cells' ability to activate through TCR/CD3 signaling.

Example 9: Alloreactive Killing of CD19+ Target Cells by CD3KO-19SN-εCS T Cells in Cis To determine the cytotoxicity of alloreactive CD3KO-19SN-εCS T cells against target cells expressing CD19, primary CD8+ T cells from a donor with HLA-I (A11:01, A30:02; B18:01, B51:01; C05:01, C15:02) mismatched with MDA-MB-231 cells were stimulated with MDA-MB-231 cells, transduced and electroporated to knock out CD3ε as described in EXAMPLES 4, 5 and 6. The cells were sorted and $CD3\varepsilon^{-}BFP^{+}MycTag^{+}$ cells were collected as CD3KO-19SN-εCS T cell. T cells were cultured with either MDA-MB-231 expressing firefly luciferase (MDA-MB-231-luci) or MDA-MB-231-CD19 expressing firefly luciferase (MDA-MB-231-CD19-luci) at a 1.5:1 ratio for 16 hrs. MDA-MB-231-luci and MDA-MB-231-CD19-luci cultured alone were used as respective controls. The luciferase activities of the cultures were determined using the Bright-Glo reagent (Promega) and read on a Victor plate reader (PerkinElmer). The percentages of specific % killing were calculated as 100×[1−(luciferase activity of sample/luciferase activity of control)].

Figure 12:
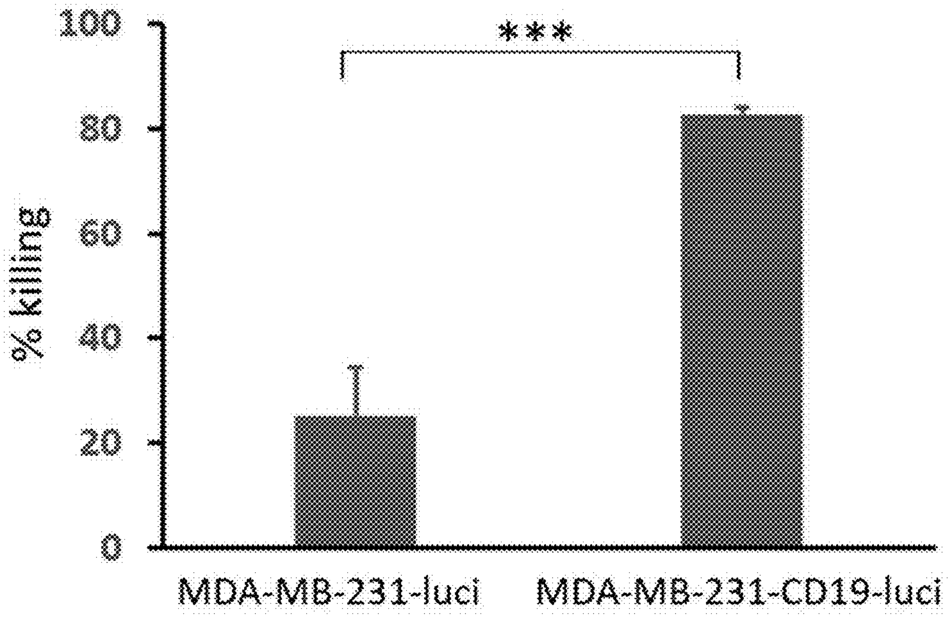
FIG. 12 depicts data for cytotoxicity of alloreactive CD3KO-195N-εCS T cells to MDA-MB-231 cells expressing CD19. Alloreactive CD3KO-195N-εCS T cells display significant higher cytotoxicity toward MDA-MB-231 cells expressing CD19 (MDA-MB-231-CD19-luci) than toward WT MDA-MB-231 cells (MDA-MB-231-luci). Data are represented as mean±SD (n=3). ***: P<0.001, Student's t-test.

As shown FIG. 12, alloreactive CD3KO-195N-εCS T cells displayed a significant higher level of cytotoxicity to MDA-MB-231 cells expressing CD19 than the WT cells. Taken together with FIG. 11, the data demonstrate the ability of alloreactive CD3KO-19SN-εCS T cells to restore TCR/CD3 expression in response to SynNotch engagement and to kill HLA-I mismatched target cells through alloreaction.

Example 10: Alloreactive T Cell Stimulation and Expansion Using Patient PBMCs or MoDCs Stimulated with TNF-α for Maturation Based on a previously published protocol (80), peripheral blood mononuclear cells (PBMCs) will be isolated from a patient leukapheresis using density-gradient centrifugation over Ficoll-Paque (MP Biomedicals, Aurora, OH, USA) and washed in OpTmizer™ culture medium (Thermo Fisher Scientific). To generate MoDCs, PBMCs from the patient will be resuspended in culture medium at a final concentration of 3 to $5\times10^{6}$ cells/mL and incubated in a standard tissue culture flask for 2 hours at 37° C. in a 5% CO2-containing atmosphere. Nonadherent cells will be removed by vigorous pipetting. The remaining adherent cells will be cultured in medium supplemented with 200 ng/mL recombinant human GM-CSF (R&D Systems, Minneapolis, MN, USA) and 4 ng/mL recombinant human interleukin IL-4 (R&D Systems). Fresh cytokines will be added every 2 to 3 days. For the maturation of DCs, culture medium will be replaced on day 6, and 1100 U/mL recombinant human TNF-α (R&D Systems) is added for 24 hours. The PBMCs and DCs will be irradiated (2500 rads) using a RS2000 irradiator (Radsource) prior to co-culture with T cells. T cells will be purified from the PBMCs of an HLA-mismatched donor using an EasySep human T cell enrichment kit (StemCell Technologies). The T cells will be labeled with 2.5 μM CFSE in labeling buffer (DPBS with 5% FBS) for 5 mins at room temperature and washed with labeling buffer three times. To stimulate and expand alloreactive T cells, CFSE-labeled T cells will be mixed with either PBMCs or matured DCs at a 1:1 ratio and cultured for 4 days in the presence of 10 ng/ml rh IL2 (R&D Systems). The cells will be harvested, stained with anti-CD3-APC and sorted for the $CD3^{+}$ $CFSE^{low}$ w population. The cells will be further expanded in culture, used for downstream genetic manipulations immediately, or cryopreserved for future use.

Example 11: Method of In Vivo Functional Study of Tumor-Activated Alloreactive T Cells in NSG Mouse Models To study the efficacy and toxicity of tumor activated alloreactive T cells for tumors in vivo, MDA-MB-231 cells will be used to form subcutaneous tumors in severely immunocompromised NSG™ mice (JAX®). To mimic the heterogeneity of TAA expression in tumor tissues, the tumors will be formed with a mixture of MDA-MB-231 expressing firefly luciferase and tumor antigen Her2 and MDA-MB-231 cells expressing luciferase only at varying ratios. Tumor development will be monitored by imaging the luciferase activity of the tumors using a IVIS Lumina LT imager (PerkinElmer). After the tumors become detectable, the mice will be treated with tumor activated alloreactive T cells (CD3KO-Her2SN-εCS T cells), conventional Her2-specific 2$^{nd}$ generation CAR T cells, anti-CD4/CD28 beads-activated but unmodified T cells or left untreated. Tumor activated alloreactive T cells will be prepared using primary human T cells from a donor with HLA-I that mismatches the HLA-I of MDA-MB-231 cells. The T cells will be stimulated with MDA-MB-231 cells, transduced with lentiviral vectors encoding Her2-specific SynNotch and Gal4-CD3-PKG-BFP cassette, and electroporated to knock out CD3ε as described in EXAMPLES 4, 5 and 6. The T cells will be administered through i.v. (intravenous) injection and their efficacy in controlling tumor growth will be monitored by imaging the tumor luciferase activities over time and by comparing the survival curves of each treatment. The CD3KO-Her2SN-εCS T cells are predicted to be the most effective in controlling tumor growth, followed by conventional Her2-specific 2$^{nd}$ generation CAR T cells, and followed by anti-CD3/CD28 beads-activated but unmodified T cells. To monitor GvH side effects caused by the therapeutic T cells, non-tumor tissues from the skin, liver, lung and heart will be examined for T cell infiltration using immunohistochemistry. The GvH side effects will also be compared by treating NSG mice without tumors with tumor activated alloreactive T cells, conventional Her2-specific 2$^{nd}$ generation CAR T cells, anti-CD3/CD28 beads-activated but unmodified T cells or left untreated. Weight loss and survival will be monitored and the levels of serum inflammatory cytokine including INFγ, IL2, IL-12, IL-17, IL5 and TNF-α will be monitored and compared. Mice treated with CD3KO-Her2SN-εCS T cells are predicated to display lower levels of GvH than mice treated with conventional Her2-specific 2$^{nd}$ generation CAR T cells or anti-CD3/CD28 beads-activated but unmodified T cells.

Example 12: Alloreactive T Cell Stimulation and Expansion Using MoDCs Stimulated with Cytokine Cocktail for Maturation and Pulsed with Tumor Cell Lysate Based on a previously published protocols (34-42), to generate MoDCs, peripheral blood mononuclear cells (PBMCs) isolated from an HLA-A2+ healthy donor using density-gradient centrifugation over Ficoll-Paque (MP Biomedicals, Aurora, OH, USA) were culture in AIM V serum-free medium (Thermo Fisher) in a tissue culture dish at the density of 106/cm2 for 2 hours at 37° C. in a humidified atmosphere of 5% CO2. Non-adherent cells were removed by washing with warm DPBS without calcium chloride and without magnesium chloride three times. The adherent cells were cultured in AIM V medium supplemented with 100 ng/mL recombinant human GM-CSF (Peprotech) and 100 ng/ml recombinant human IL-4 (Peprotech) for 3 days and the medium was replaced with fresh AIM V medium with the same concentrations of GM-CSF and IL-4. The cells were cultured for another 2 days and loosely adherent or non-adherent immature DCs were harvested and transferred to another dish and cultured at a concentration of 1×106 cells/ml in AIM V medium supplemented with 100 ng/ml recombinant human GM-CSF and 100 ng/ml recombinant human IL-4. The next day, maturation cocktail was added to the final concentrations of 10 ng/ml TNF-α (Peprotech), 10 ng/ml IL-1β (Peprotech), 10 ng/ml IL-6 (Peprotech), and 1 μg/ml PGE2 (Sigma). In addition, MDA-MB-231 tumor cells lysate was added to DCs at a ratio of 3 tumor cell equivalents to 1 MoDC. To prepare tumor cell lysate, MDA-MB-231 cells were heat-shocked by incubating at 42° C. for 25 minutes (45-47). Cells were harvested, washed with phosphate-buffered saline (PBS), and resuspended in DPBS at 1×107 cells/ml, before 5 cycles of freezing and thawing (ethanol with dry ice and 56° C.). Solid debris was then spun down at 1700 g for 5 minutes and the supernatant was collected to be used as tumor cell lysate immediately or stored at −80° C.

Figure 16:
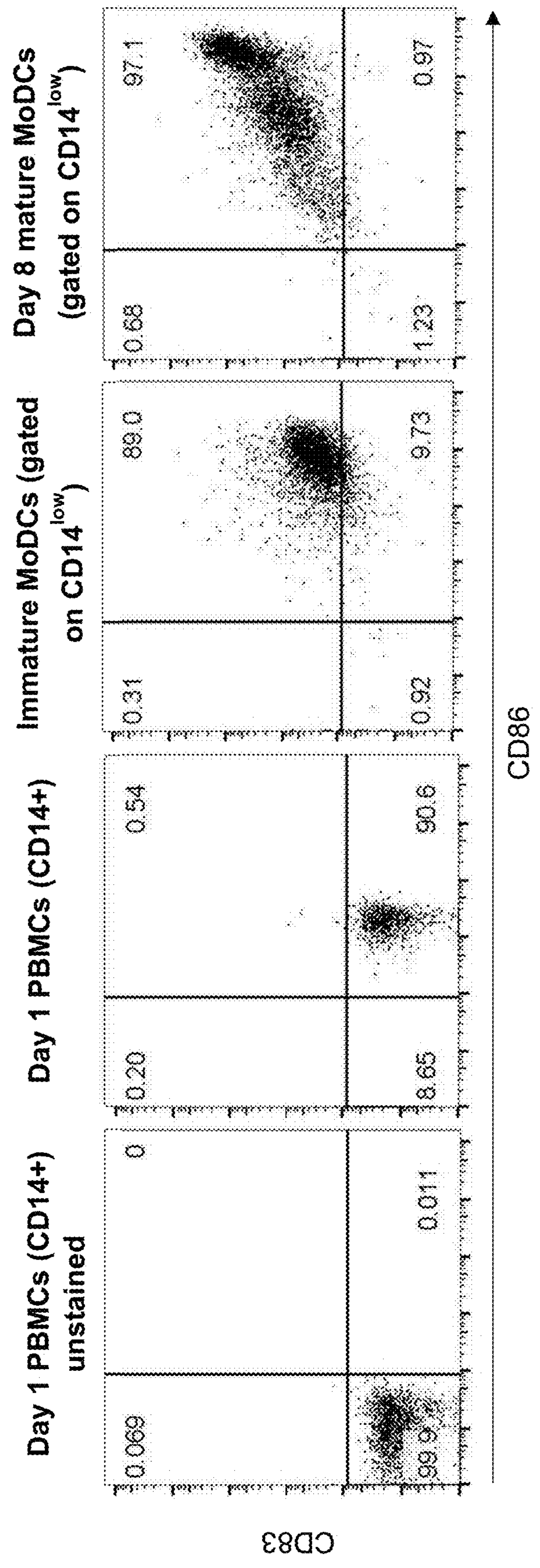
FIG. 16 depicts flow cytometry data showing the phenotypes of PBMCs, immature monocyte-derived dendritic cells (MoDCs), and mature MoDCs. PBMCs were cultured in AIM V medium containing 100 ng/ml GM-CSF and 100 ng/ml IL-4 for 6 days to generate immature MoDCs. The cells were then stimulated with the maturation cocktail for 2 days. Compared with immature MoDCs, mature MoDCs showed increased levels of CD83 and CD86 expression. PBMCs: peripheral blood mononuclear cells (PBMCs). MoDCs: monocyte-derived dendritic cells.

Two days after the addition of maturation cocktail and tumor cell lysate, the mature MoDCs were analyzed for the expression of surface markers CD14, CD83 and CD86 by flow cytometry. As shown in FIG. 16, compared with immature MoDCs, mature MoDCs showed increased levels of CD83 and CD86 expression.

Figure 17:
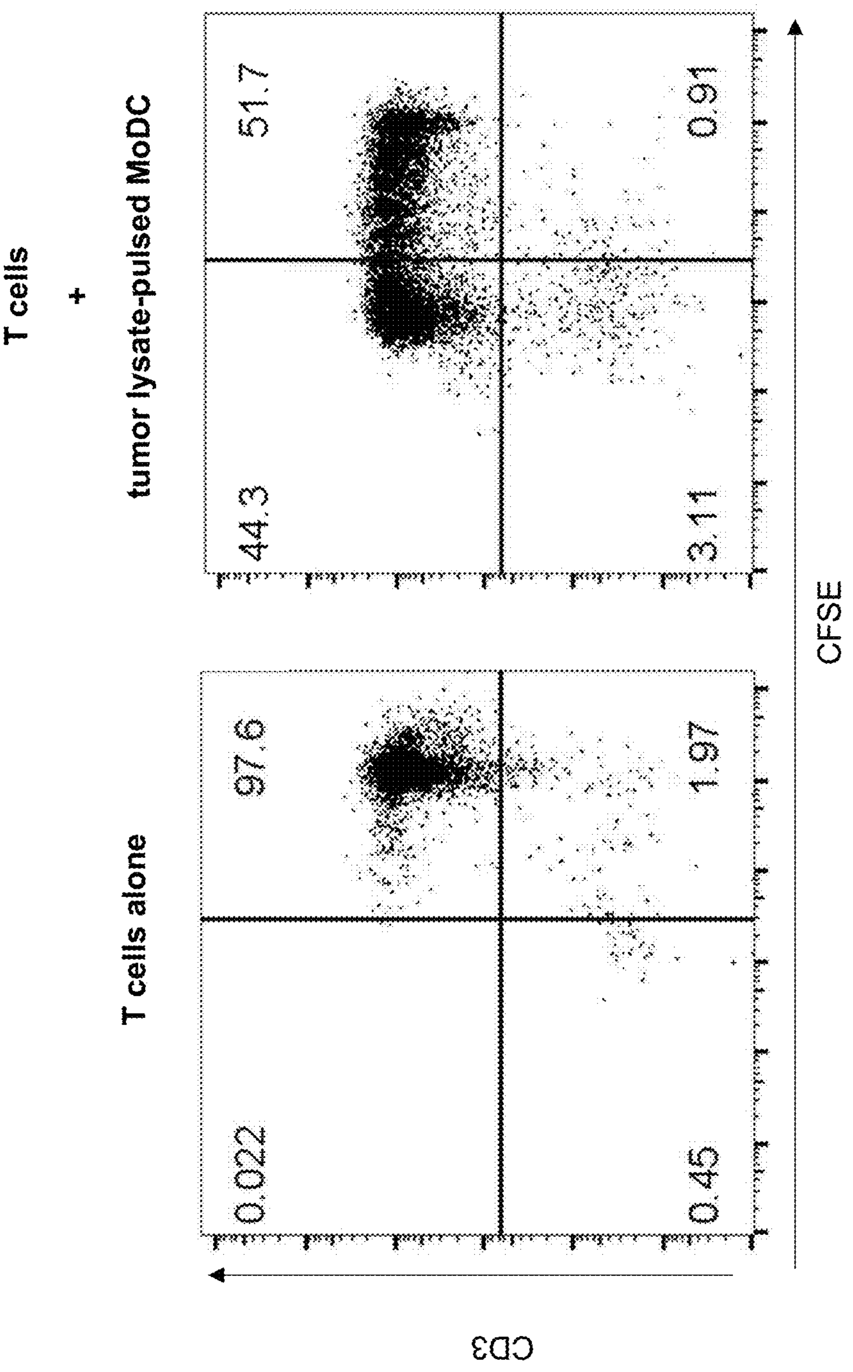
FIG. 17 depicts the flow cytometry data showing the proliferation of T cells stimulated with HLA-mismatched monocyte-derived dendritic cells (MoDCs). MoDCs were generated with PBMCs from an $HLA\text{-}A2^+$ donor, matured with the maturation cocktail and pulsed with MDA-MB-231 tumor cell lysate. Mature MoDCs were cultured with CF SE-labeled T cells from an HLA-A2-donor at a 1:3 ratio for 9 days. T cell proliferation were analyzed by flow cytometry. Carboxyfluorescein diacetate succinimidyl ester (CFSE)-labeled T cells cultured alone were used as a control.

Example 13: Alloreactive T Cell Expansion by MoDCs and the Cytotoxicity of Expanded Alloreactive T Cells Toward Tumor Cells To determine the ability of tumor lysate-pulsed mature MoDCs to expand alloreactive T cells, MoDCs as described in Example 12 were cultured with carboxyfluorescein diacetate succinimidyl ester (CFSE)-pulsed T cells from an HLA-A2$^-$ donor at a 1:3 ratio for 9 days. Significant T cell proliferation was observed (FIG. 17) and the CFSE$^-$ T cells represent expanded alloreactive T cells.

To determine the ability of the expanded alloreactive T cells to kill HLA-A2$^+$ MDA-MB-231 tumor cells, the T cells were cultured with MDA-MB-231 cells expressing luciferase (MDA-luci) or HLA-I$^-$ MDA-MB-231 cells (β2m knocked out which results in the loss of HLA-I surface expression) expressing luciferase (MDA-β2m-KO-luci) at a 3:1 ratio for 16 hrs. The MDA-β2m-KO-luci cells were generated by transducing MDA-MB-231 β2m KO cells (FIG. 5) with a pLX313 lentiviral vector encoding firefly luciferase and selected with hygromycin for stable expressors. The killing of MDA-MB-231 cells was determined using a luciferase-based assay. See FIG. 18 description.

Figure 18:
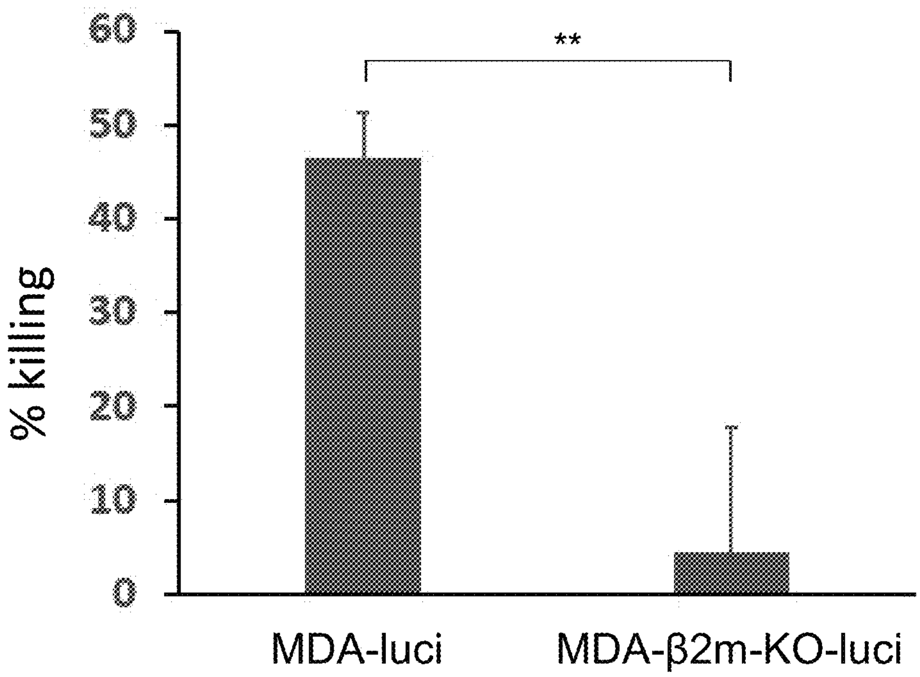
FIG. 18 depicts data of the cytotoxicity of monocyte-derived dendritic cell (MoDC)-expanded alloreactive T cells against tumor cells. T cells from an $HLA\text{-}A2^-$ donor were expanded with MoDCs derived from an $HLA\text{-}A2^+$ donor. The MoDCs were matured with the maturation cocktail and pulsed with MDA-MB-231 cell lysate. Expanded T cells were cultured with MDA-MB-231 cells expressing luciferase (MDA-luci) or MDA-MB-231 cells that have β2m knocked out (which leads to the loss of HLA-I surface expression) and express luciferase (MDA-β2m-KO-luci) at a 3:1 ratio for 16 hrs. MDA-luci and MDA-β2m-KO-luci cells culture alone were used as controls. The luciferase activities of the remaining live MDA-MB-231 cells were determined using a Bright-Glo kit (Promega) and % killing was calculated 100×[1−(luciferase activity of sample/luciferase activity of control)]. Data are represented as mean±SD (n=3). **: p<0.01, Student's t-test.

As shown in FIG. 18, the alloreactive T cells displayed significant cytotoxicity toward wild type MDA-MB-231 cells but largely spared MDA-MB-231 cells that do not express HLA-I. These data demonstrate the alloreactive nature of the killing.

Example 14: CD3γ, CDδ, CD3ζ and CD8α Knockout (KO) Using CRISPR-Cas9

To knock out CD3γ, CDδ, CD3ζ or CD8α expression in human T cells, primary human CD8$^+$ T cells were stimulated with anti-CD3/CD28 beads for 4 to 5 days, and then were electroporated using the Neon Transfection System (ThermoFisher) to prepare four different populations each with a single knock out. Specifically, ribonucleoprotein (RNP) was formed by incubating 7.5 pmol of single guide RNA (sgRNA) and 7.5 pmol of Alt-R S.p Cas9 Nuclease V3 (IDT) in 5 μl Buffer R for 15 mins. The crRNA sequences of the sgRNA sequences used are: for CD3γ, Hs.Cas9.CD3G.1.AH (5'-GUAAUGCCAAGGACCCUCGA-3'; SEQ ID NO: 17); for CDδ, Hs.Cas9.CD3D.1.AB (5'-CCCCUUCAAGAUACCUAUAG-3'; SEQ ID NO: 18); for CD3ζ, Hs.Cas9.CD247.1.AC (5'-GAUGGAAUCCUCUUCAU-CUA-3'; SEQ ID NO: 19); and for CD8α, Hs.Cas9.CD8A.1.AA (5'-GCUGCUGUCCAACCCGACGU-3'; SEQ ID NO: 20). The RNP was then mixed with $0.2\times10^6$ T cells in Buffer R, loaded into a 10 μl tip and electroporated using the program #24 (1600 v, 10 ms, 3 pulses).

Figure 19:
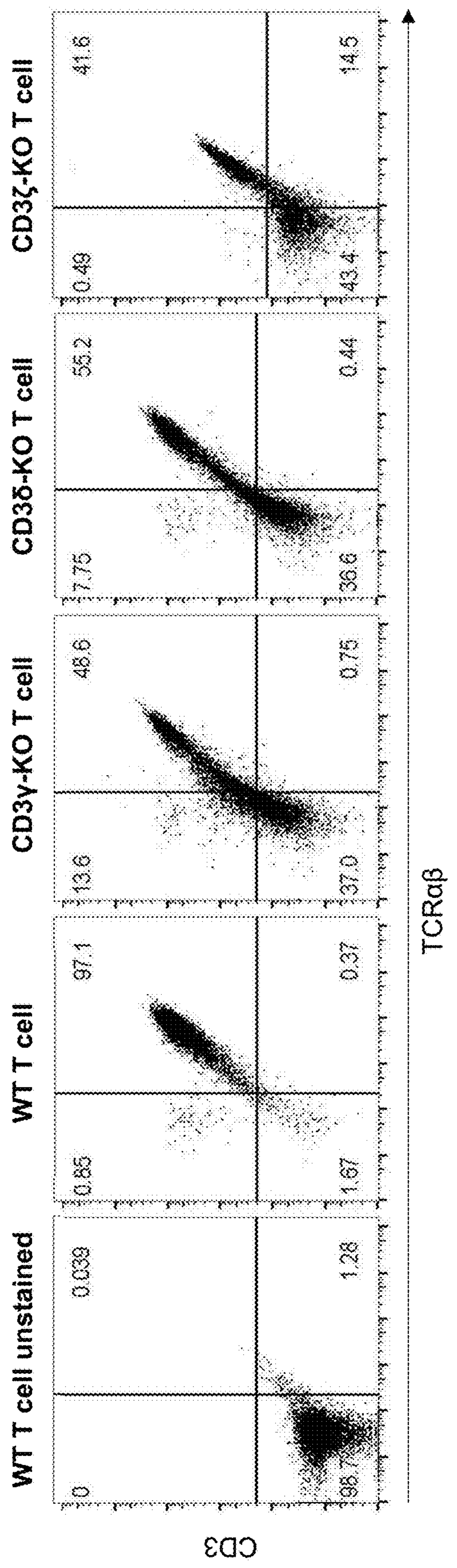
FIG. 19 depicts flow cytometry data showing CD3ε and TCRβ expression of human $CD8^+$ T cells 3 days after being electroporated to knock out the expression of CD3γ, CDδ, or CD3ζ using CRISPR-Cas9 . . . CD3γ-KO: CD3γ knocked out. CDδ-KO: CDδ knocked out. CD3ζ-KO: CD3ζ knocked out. WT: wild type.
Figure 20:
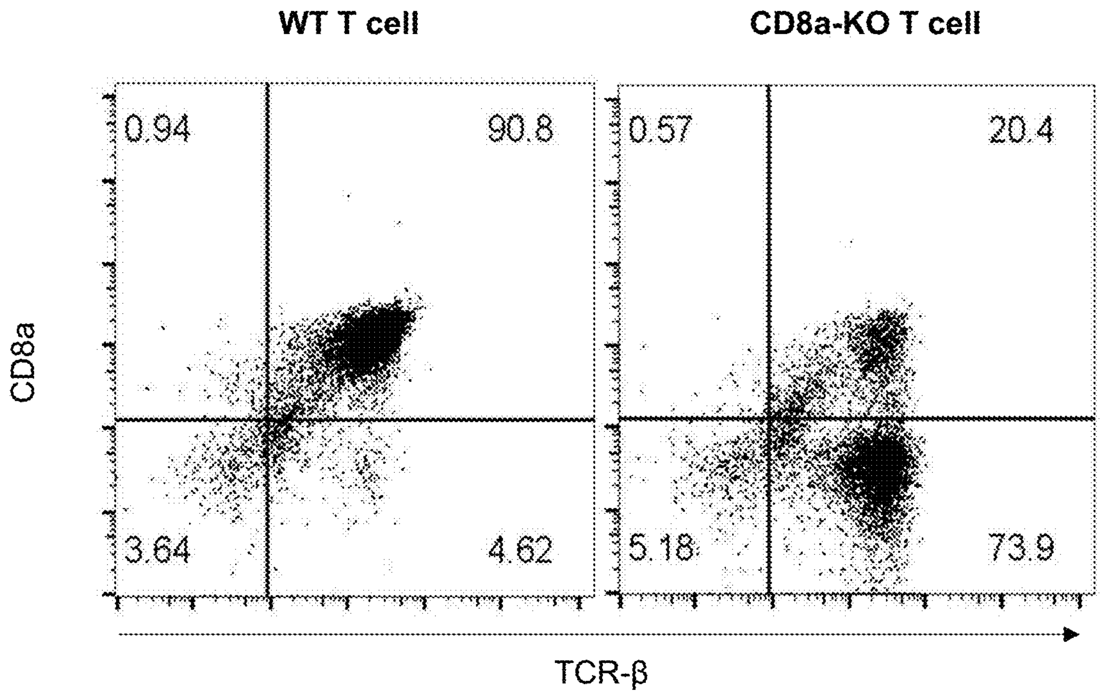
FIG. 20 depicts flow cytometry data for CD8α and TCRβ expression on human $CD8^+$ T cells 3 days after being electroporated to knock out the expression of CD8a using CRISPR-Cas9. CD8α-KO: knock out of CD8 α.

As shown in FIG. 19, at three days post electroporation for CD3γ KO, CDδ KO, and CD3ζ KO, more than 30% T cells were stained negative for both CD3ε and TCRβ. These data indicate efficient CD3 knockout and the intracellular retention of the TCR/CD3 complex as a result. As shown in FIG. 20, ~74% of T cells lost CD8 expression after CD8α KO and, as expected, the expression of TCR was not affected.

Example 15: Alloreactive Killing of $CD19^+$ Target Cells by CD3KO-19SN-εCS T Cells in Trans To determine the ability of CD3KO-195N-εCS T cells to kill $CD19^-$ target cells in the presence of $CD19^+$ target cells, CD3KO-195N-εCS T cells were generated as described in Example 16 except that lentiviral vectors encoding CD19-specific SynNotch, rather than lentiviral vectors encoding Her2-specific SynNotch, were used. Briefly, primary $CD8^+$ T cells from a donor with HLA-I (A11:01, A30:02; B18:01, B51:01; C05:01, C15:02) mismatched with MDA-MB-231 cells were stimulated with MDA-MB-231 cells, transduced and electroporated to knock out CD3ε as described in EXAMPLES 4, 5, and 6. The cells were sorted and $CD3\varepsilon^-$ $BFP^+MycTag^+$ cells were collected as CD3KO-19SN-εCS T cell. To prepare target cells for trans killing, MDA-MB-231 cells or MDA-MB-231 cells expressing CD19 (MDA-MB231-CD19) (FIG. 10) were mixed with MDA cells expressing luciferase (MDA-MB-231-luci) at a 1:1 ratio. CD3KO-19SN-εCS T cells were added at a 3:1 ratio (T cells to total MDA cells) and incubated for 48 hrs before the luciferase activities of the remaining live MDA-MB-231-luci cells were determined. MDA-MB-231 cell mixtures cultured alone without T cells were used for determining maximum luciferase activities.

Figure 21:
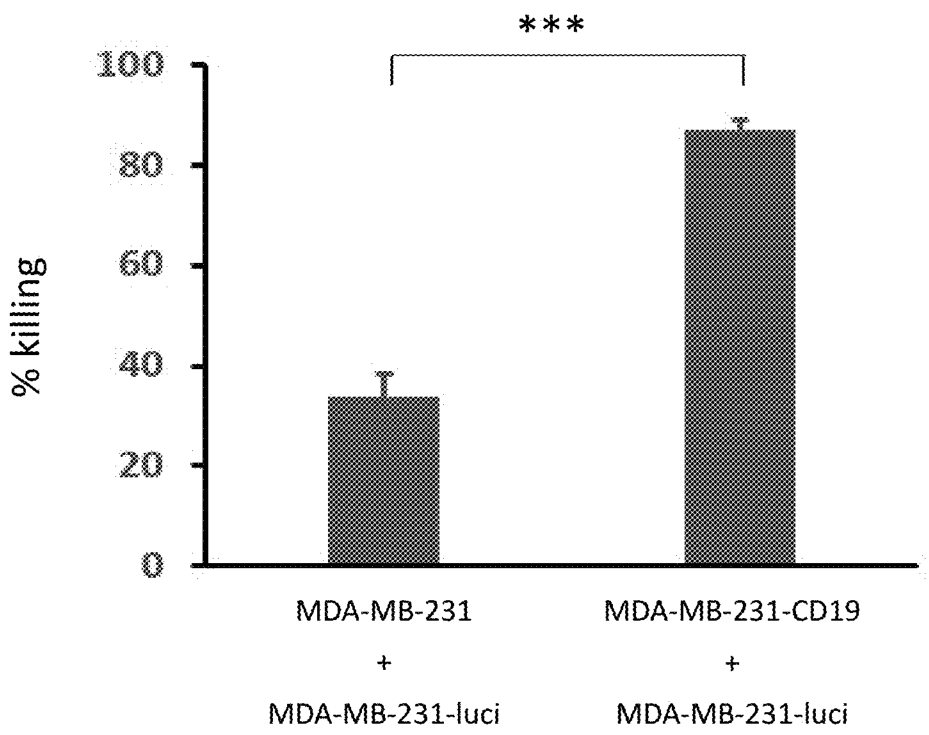
FIG. 21 depicts data indicating the trans killing of $CD19^-$ MDA-MB-231 cells by CD3KO-19SN-εCS T cells in the presence of $CD19^+$ MDA-MB-231 cells. MDA-MB-231 cells or MDA-MB-231 cells expressing CD19 (MDA-MB-231-CD19) were mixed with MDA cells expressing luciferase (MDA-MB-231-luci) at a 1:1 ratio. CD3KO-19SN-εCS T cells were added at a 3:1 ratio (T cells to total MDA cells) and incubated for 48 hrs before the luciferase activities of the remaining live MDA-MB-231-luci cells were determined. MDA-MB-231 cell mixtures cultured alone without T cells were used for determining maximum luciferase activities. The % killings were calculated as [1−(sample activity)/(max activity)]×100. Data are represented as mean±SD (n=3). ***: P<0.001.

As shown in FIG. 21, significantly higher killing of MDA-MB-231-luci cells was observed when mixed with MDA-MB-231-CD19 than with MDA-MB-231 cells. Since MDA-MB-231-luci cells did not express CD19, the higher % killing was the result of T cell alloreactivity regained through interactions with MDA-MB-231-CD19.

Example 16: Generation of Tumor-Activated Alloreactive T Cells Based on Her2-Specific SynNotch (CD3KO-Her2SN-εCS T Cells)

The transfer vector pHR_PGK_antiHer24D5-8_synNotch_Gal4VP64 (Addgene Cat. #85425) was used to package lentiviral vectors for Her2-specific SynNotch. The expression of Her2-specific SynNotch receptor was driven by a constitutively active PGK-1 promoter. The Her2-specific SynNotch receptor comprises a N-terminal MycTag followed by a Her2-specific extracellular single chain variable fragment (scFv), a Notch core sequence including the transmembrane domain, and an intracellular domain containing a cleavable artificial transcription activator Gal4-VP64, which consists of a Gal4 DNA binding domain and a VP64 transcription activation domain (14, 55).

To prepare lentiviral vectors for the CD3ε expression cassette, the transfer vector pHR_Gal4UAS_ IRES_mC_ pGK_tBFP (Addgene #79123) (14, 55) was modified by inserting a human CD3ε coding sequence downstream the Gal4 binding sites and removing the IRES-mCherry sequence. The human CD3ε coding sequence was codon optimized so that the target-specific sequence of the gRNA for CD3ε knockout no longer functions through recognizing the CD3ε coding sequence in the cassette and working with Cas9 to cleave it. The resulting transfer vector encodes a Gal4-CD3-PKG-BFP cassette (SEQ ID NO: 1) in which CD3ε expression is controlled by the Gal4 binding sequence and the expression of blue fluorescence protein (BFP) is driven by a constitutively active PGK-1 promotor (FIG. 15). BFP expression therefore serves as a marker for the presence of the cassette in transduced cells. Lentiviral vectors for both the Her2-specific SynNotch and the CD3ε expression cassette were packaged in Lenti-X 293T cells (Takara) and concentrated 100-fold using the Lentivirus Precipitation Solution (ALSTEM).

The following steps were used to generate tumor-activated alloreactive T cells based on Her-specific SynNotch, Step 1) T cell activation. On Day 0, $0.75\times10^6$ purified primary human $CD8^+$ T cells from a healthy donor with HLA-I (A11:01, A30:02; B18:01, B51:01; C05:01, C15:02) mismatched with MDA-MB-231 cells were co-cultured with $0.125\times10^6$ MDA-MB-231 cells in a 48 well plate in OpTmizer™ culture medium supplemented with 10 ng/ml rhIL-2 and 1 μg/ml Ultra-LEAF™ purified anti-CD28 monoclonal antibody (Biolegend, clone CD28.2). Step 2) Transduction. On Day 1, 50 μl concentrated lentiviral vectors each for Her2-specific SynNotch and Gal4-CD3-PKG-BFP cassette were added to the co-culture. Protamine sulfate was also added to the concentration of 10 μg/ml. On day 2, medium was replaced with fresh medium containing 10 ng/ml rhIL-2 and 1 μg/ml anti-human CD28 antibody to dilute protamine sulfate. On Day 5, the expanded T cells were transferred to a 6-well plate at a concentration of $10^6$/ml. Step 3) CD3ε knock out. On Day 6, the T cells were electroporated using the Neon Transfection System (ThermoFisher) to introduce CD3ε-targeting sgRNA and Cas9 as described in Example 6. Step 4) Analysis and purification of CD3KO-Her2SN-εCS T cells. On Day 9, the cells were harvested and stained with anti-CD3ε antibody for CD3 expression and anti-MycTag (Cell Signaling Technology, clone 9B 11) for SynNotch expression. The presence of CD3ε expression cassette in T cells was marked by the expression of BFP. $CD3^-MycTag^+$ $BFP^+$ cells were sorted as CD3KO-Her2SN-εCS T cells.

Figures 22A, 22B:
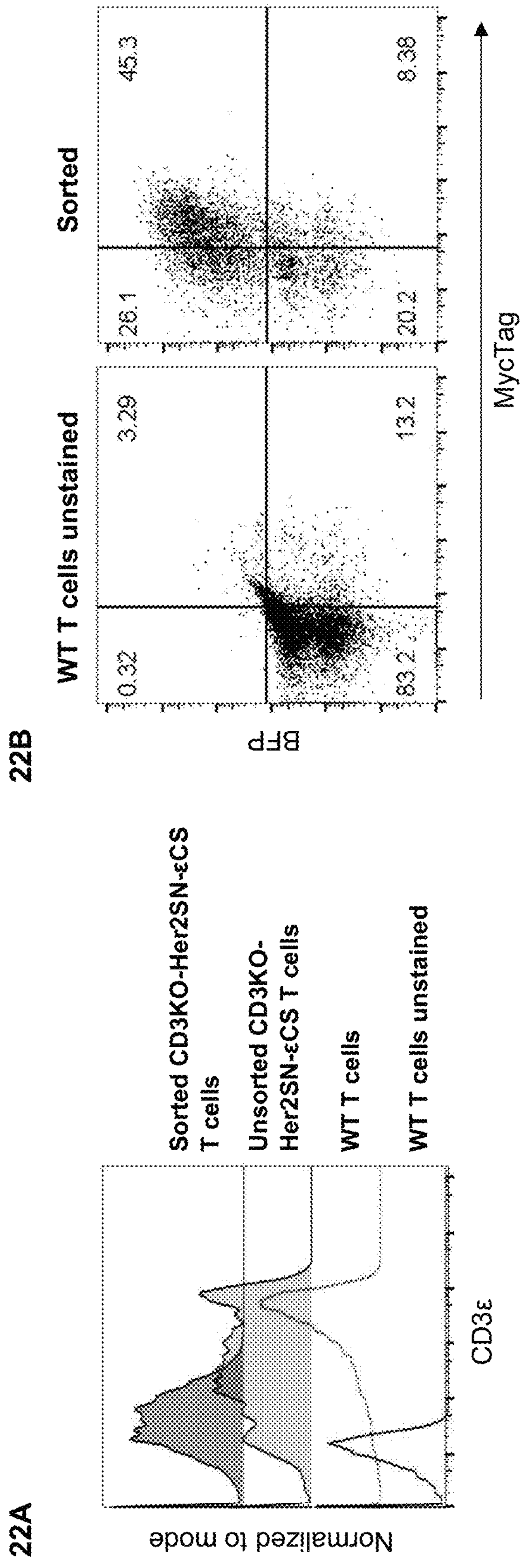
FIGS. 22A and 22B depict flow cytometry data characterizing the CD3KO-Her2SN-εCS T cells in terms of the expression of CD3ε and Her2-specific SynNotch and the incorporation of the CD3ε expression cassette.

As shown in FIGS. 22A and 22B, sorted CD3KO-Her2SN-εCS T cells showed negative to low CD3ε expression, positive MycTag expression indicating Her2-specific SynNotch expression and positive BFP expression indicating the incorporation of the CD3ε expression cassette.

Example 17: Engagement of Anti-Her2 SynNotch Restored CD3ε Expression on CD3KO-Her2SN-εCS T Cells and Enabled the Cells to Activate in Response to Anti-CD3 Stimulation To test the ability of CD3KO-Her2SN-εCS T cells to restore CD3 expression and react to anti-CD3 stimulation, 200,000 CD3KO-Her2SN-εCS T cells generated as described in Example 16 were stimulated for 16 hours with 80,000 MDA-MB-231 with the low levels of intrinsic Her2 expression knocked out (MDA-HerKO) or MDA-MB-231 cells transduced to express Her2 at high levels (MDA-Her2) (FIGS. 23A-23C) in a 96-well tissue culture plate. MDA-HER2KO cells were generated by knocking out Her2 expression in MDA-MB-231 cells using CRISPR/Cas9 with the sgRNA Hs.Cas9.ERBB2.1.AA (IDT) (crRNA sequence 5'-CAACUACCUUUCUACGGACG-3'; SEQ ID NO: 21). MDA-Her2 cells were generated by transducing MDA-MB-231 cells with a pLVx lentiviral vector encoding Her2 and were selected using puromycin for stable expressors. The T cells were then transferred to a separate well containing anti-CD3/CD28 Dynabeads (Life Technologies) at a 1:1 bead to T cell ratio and incubated for 6 hours in the presence of monensin (Biolegend) and FITC-conjugated anti-human-CD107a antibody (Biolegend, clone H4A3). Beads were then removed, and the cells were fixed in 4% formaldehyde, permeabilized with permeabilization buffer (0.5% BSA, 0.1% saponin, in DPBS/azide), stained with anti-human-CD3 and anti-human-IFNγ (Biolegend clone 4S.B3) antibodies and analyzed using a NovoCyte Quanteon flow cytometer.

Figures 24A, 24B:
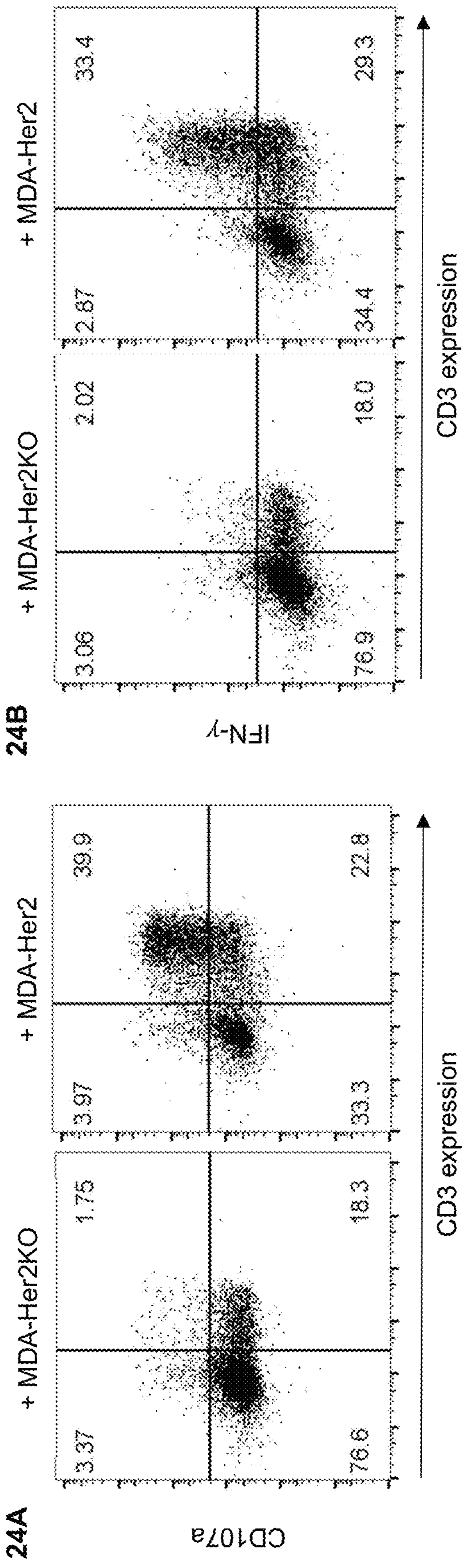
FIGS. 24A and 24B depict flow cytometry data illustrating that engagement of anti-Her2 SynNotch restores CD3 expression on CD3KO-Her2SN-εCS T cells and enables the cells to activate in response to anti-CD3 antibody stimulation in terms of degranulation (CD107a) (FIG. 24A) and IFNγ production (FIG. 24B). Cells were gated on $BFP^+$ population.

The data are shown in FIGS. 24A and 24B. A significant number of BFP+CD3KO-Her2SN-εCS T cells restored CD3 expression in response to MDA-Her2 cells but not to MDA-Her2KO cells. Among the T cells with restored CD3 expression, most degranulated as indicated by the positive CD107a staining (FIG. 24A) and produced IFNγ (FIG. 24B). The results demonstrate that in response to Her2-specific SynNotch engagement, CD3KO-Her2SN-εCS T cells were able to restore the expression of CD3, which is capable of mediating T cell activation in response to anti-CD3 stimulation.

Example 18: Alloreactive Killing of Herr Target Cells by CD3KO-Her2SN-εCS T Cells in Cis To determine the cytotoxicity of alloreactive CD3KO-Her2SN-εCS T cells to $Her2^+$ target cells, CD3KO-Her2SN-εCS T cells generated as described in Example 16 were cultured with MDA-MB-231 cells expressing firefly luciferase and Her2 (MDA-luci-Her2) (FIG. 23) at a 1:1 or 1.5:1 T cell ratio for 16 hours. As a control, T cells were cultured with MDA-MB-231 cells expressing luciferase and with the low levels of intrinsic Her2 expression knocked out (MDA-luci-Her2KO) (FIG. 23). MDA-luci-Her2 cells and MDA-luci-Her2KO cells were generated by transducing MDA-Her2 and MDA-Her2KO, respectively, using a pLX313 lentiviral vector encoding firefly luciferase and were selected using hygromycin for stable expressors. MDA-luci-Her2 and MDA-luci-Her2KO cells cultured alone were used as respective controls. The luciferase activities of the cultures were determined using the Bright-Glo reagent (Promega) and read on a Victor plate reader (PerkinElmer). The percentages of specific % killing were calculated as 100× [1−(luciferase activity of sample/luciferase activity of control)].

Figure 25:
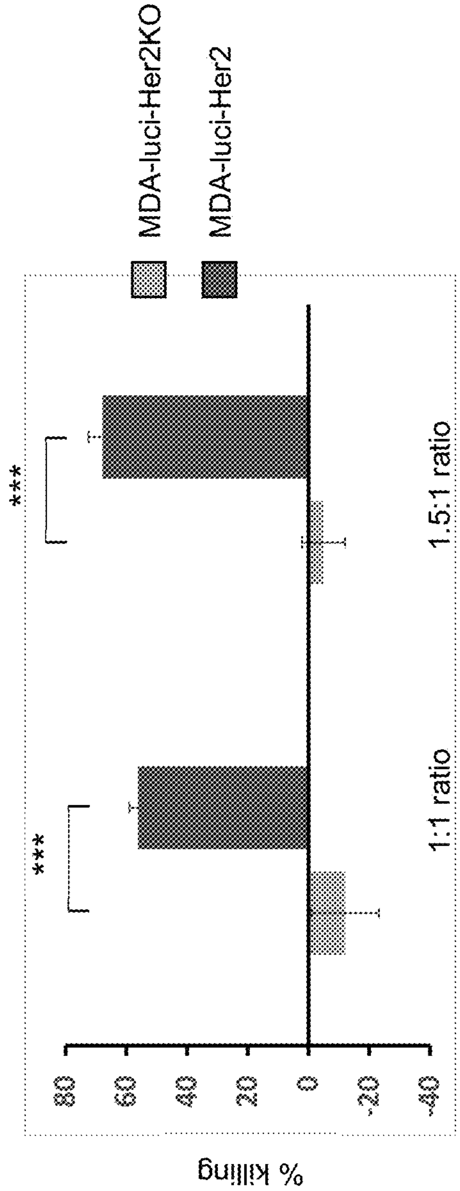
FIG. 25 depicts data showing the cytotoxicity of alloreactive CD3KO-Her2SN-εCS T cells to MDA-MB-231 cells expressing Her2. Alloreactive CD3KO-195N-εCS T cells display significant higher cytotoxicity toward MDA-MB-231 cells expressing Her2 (MDA-luci-Her2) than toward Her2-negative MDA cells (MDA-luci-Her2KO). T cells and target cells were cultured at a 1:1 or 1.5:1 ratio for 16 hours before the luciferase activities in the remaining live cells were determined. Data are represented as mean±SD (n=3). ***: P<0.001, Student's t-test.

As shown FIG. 25, alloreactive CD3KO-Her2SN-εCS T cells displayed a significant higher level of cytotoxicity to MDA-luci-Her2 cells than MDA-luci-Her2KO. Taken together with FIGS. 24A and 24B, the data demonstrate the ability of alloreactive CD3KO-19SN-εCS T cells to restore TCR/CD3 expression in response to SynNotch engagement and to kill HLA-I mismatched target cells through alloreaction.

Figures 23A, 23B, 23C:
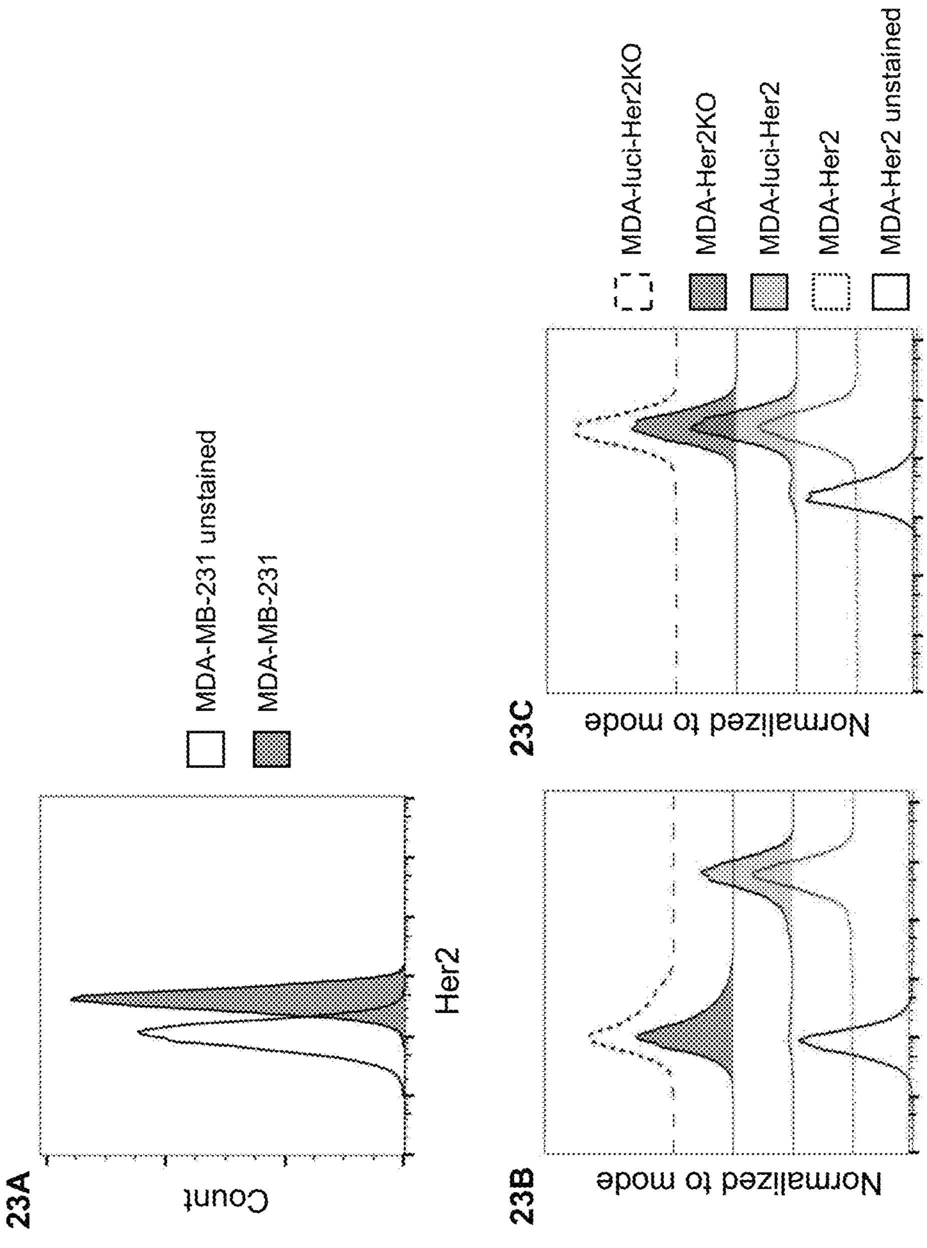
FIGS. 23A-23C depict flow cytometry data showing Her2 and HLA-I expression on wild type MDA-MB-231 cells, MDA-MB-231 cells transduced to express Her2 (MDA-Her2), MDA-MB-231 cells transduced to express both luciferase and Her2 (MDA-luci-Her2), MDA-MB-231 with the low level of intrinsic Her2 expression knocked out using CRISPR/Cas9 (MDA-Her2KO) and MDA-Her2KO cells transduced to express luciferase (MDA-luci-Her2KO).

Example 19: Alloreactive Killing of Her2+ Target Cells by CD3KO-Her2SN-εCS T Cells in Trans To determine the ability of CD3KO-Her2SN-εCS T cells to kill $Her2^-$ target cells in the presence of $Her2^+$ target cells, three types of MDA-MB-231 cells were used as target cells: $Her2^-$ MDA-luci-Her2KO, $Her2^-$ MDA-Her2KO, and $Her2^+$ MDA-Her2 (FIGS. 23B and 23C). To prepare target cells for trans killing, MDA-Her2-KO or MDA-Her2 were mixed with MDA-luci-Her2KO at a 1:1 ratio. CD3KO-Her2SN-εCS T cells generated as described in Example 16 were added at a 3:1 or 5:1 ratio (T cells to total MDA-MB-231 cells) and incubated for 48 hrs. MDA-MB-231 cell mixtures cultured alone without T cells were used for determining maximum luciferase activities.

Figure 26:
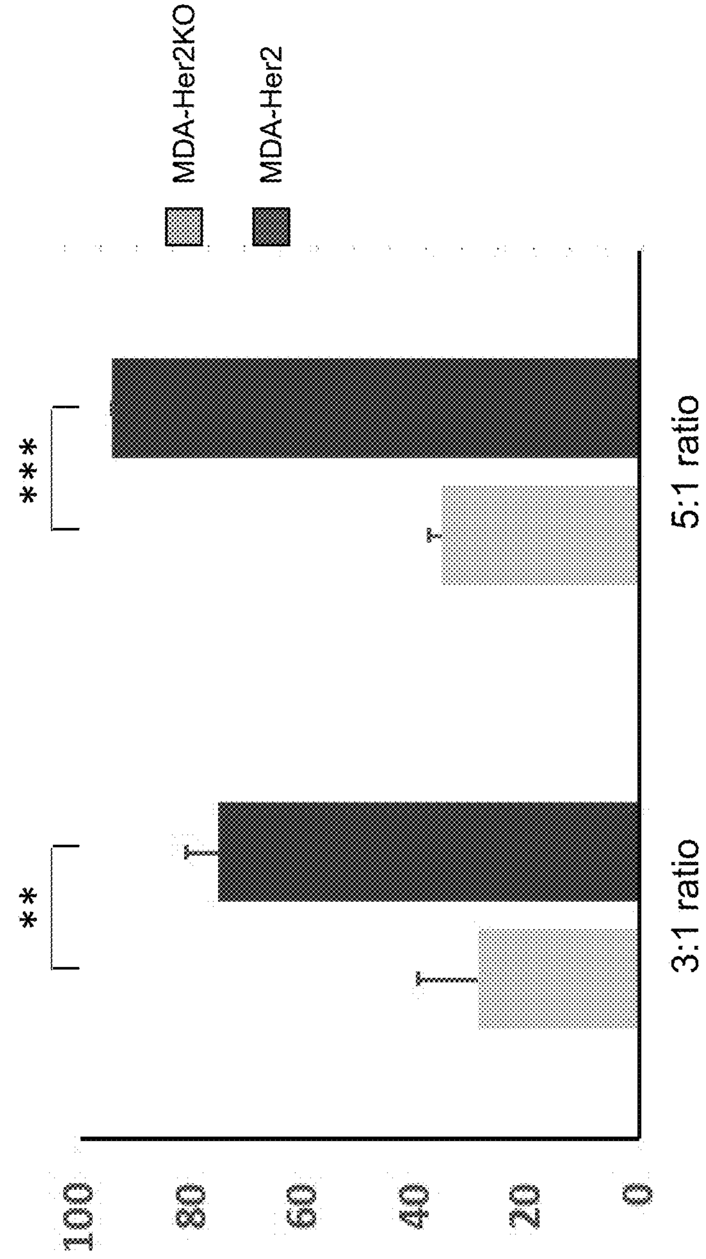
FIG. 26 depicts the trans killing of $Her2^-$ MDA-MB-231 cells by CD3KO-Her2SN-εCS T cells in the presence of $Her2^+$ MDA-MB-231 cells. $Her2^-$ MDA-Her2KO or $Her2^+$ MDA-Her2 cells were mixed with $Her2^-$ MDA cells expressing luciferase (MDA-luci-Her2KO) at a 1:1 ratio. CD3KO-Her2SN-εCS T cells were added at a 3:1 or 5:1 ratio (T cells to total MDA cells) and incubated for 48 hrs before the luciferase activities of the remaining live MDA-luci-Her2KO cells were determined. MDA cell mixtures cultured alone without T cells were used for determining maximum luciferase activities. The % killings were calculated as [1−(sample activity)/(max activity)]×100. Data are represented as mean±SD (n=3). : P<0.01. *: P<0.001, Student's t-test.

As shown in FIG. 26, significantly higher killings of MDA-luci-Her2KO cells were observed when mixed with MDA-Her2 than when mixed with MDA-Her2KO. Since MDA-luci-Her2KO cells did not express Her2, the higher % killings were the results of T cell alloreactivity regained through interactions with MDA-Her2.

Example 20: Generation of Tumor-Activated Alloreactive T Cells Based on Her2-Specific CAR (CD3KO-Her2CAR-εCS T Cells) and NFAT-Driven CD3ε Expression Cassette Lentiviral vectors for Her2-specific CAR were packaged using the transfer vector z368-EF1a-4D5-2gCAR. The vector encodes a Her2-specific second generation CAR (SEQ ID NO: 22) driven by an EF1α promoter. The Her2-specific CAR comprises an N-terminal 4D5 scFv followed by a CD8a linker, a transmembrane domain, a 4-1BB signaling domain and a CD3ζ signaling domain with three ITAMs.

To prepare lentiviral vectors for the NFAT-driven CD3ε expression cassette, the transfer vector pHR_Gal4UAS_IRES_mC_pGK_tBFP (Addgene #79123) (14, 55) was modified by inserting a human CD3ε coding sequence downstream the Gal4 binding sites, removing the IRES-mCherry sequence and then replacing the five Gal4 binding sequences and the minimal promoter with four NFAT (4×NFAT) binding sequences followed by a synthetic minimal promoter. The human CD3ε coding sequence was codon optimized so that the target-specific sequence of the gRNA for CD3ε knockout no longer functions through recognizing the CD3ε coding sequence in the cassette and working with Cas9 to cleave it. The resulting transfer vector encodes a 4×NFAT-CD3-PKG-BFP cassette (SEQ ID NO: 23) in which CD3ε expression is controlled by the 4×NFAT binding sequence and the expression of blue fluorescence protein (BFP) is driven by a constitutively active PGK-1 promotor (FIG. 15). BFP expression therefore serves as a marker for the presence of the cassette in transduced cells. Lentiviral vectors for both the Her2-specific CAR and the 4×NFAT-CD3-PKG-BFP cassette were packaged in Lenti-X 293T cells (Takara) and concentrated 100-fold using the Lentivirus Precipitation Solution (ALSTEM).

The following steps were used to generate tumor-activated alloreactive T cells based on Her-specific CAR, Step 1) T cell activation. On Day 0, $0.75\times10^6$ purified primary human $CD8^+$ T cells from a healthy donor with HLA-I (A11:01, A30:02; B18:01, B51:01; C05:01, C15:02) mismatched with MDA-MB-231 cells were co-cultured with $0.125\times10^6$ MDA-MB-231 cells in a 48 well pate in OpTmizer™ culture medium supplemented with 10 ng/ml rhIL-2 and 1 μg/ml Ultra-LEAF™ purified anti-CD28 monoclonal antibody (Biolegend, clone CD28.2). Step 2) Transduction. On Day 1, 50 μl concentrated lentiviral vectors each for Her2-specific CAR and 4×NFAT-CD3-PKG-BFP cassette were added to the co-culture. Protamine sulfate was also added to the concentration of 10 μg/ml. On day 2, the medium was replaced with fresh media containing 10 ng/ml rhIL-2 and 1 μg/ml anti-human CD28 antibody to dilute protamine sulfate. On Day 5, the expanded T cells were transferred to a 6-well plate at a concentration of $10^6$/m. Step 3) CD3ε knock out. On Day 6, the T cells were electroporated using the Neon Transfection System (ThermoFisher) to introduce CD3ε-targeting sgRNA and Cas9 as described in Example 6. Step 4) Analysis and purification of CD3KO-Her2CAR-εCS T cells. on Day 9, the cells were harvested and stained with anti-CD3ε antibody for CD3 expression. The cells were also stained with recombinant human Her2 followed by anti-Her2/CD340 antibody (Biolegend) for the expression of Her2-specific CAR. The presence of NFAT-driven CD3ε expression cassette in T cells was marked by the expression of BFP. $CD3^-$ $CAR^+BFP^+$ cells were sorted as CD3KO-Her2CAR-εCS T cells.

Figure 27A:
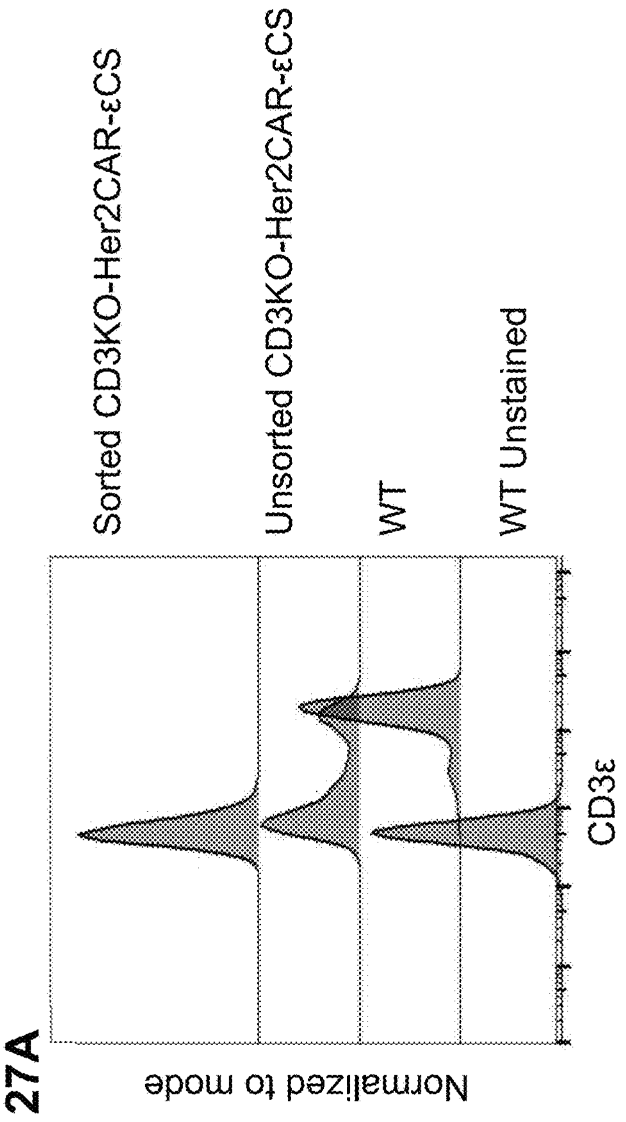
FIGS. 27A and 27B depict the flow cytometry data characterizing the CD3KO-Her2CAR-εCS T cells in terms of the expression of CD3ε and Her2-specific CAR and the incorporation of the CD3ε expression cassette.
Figure 27B:
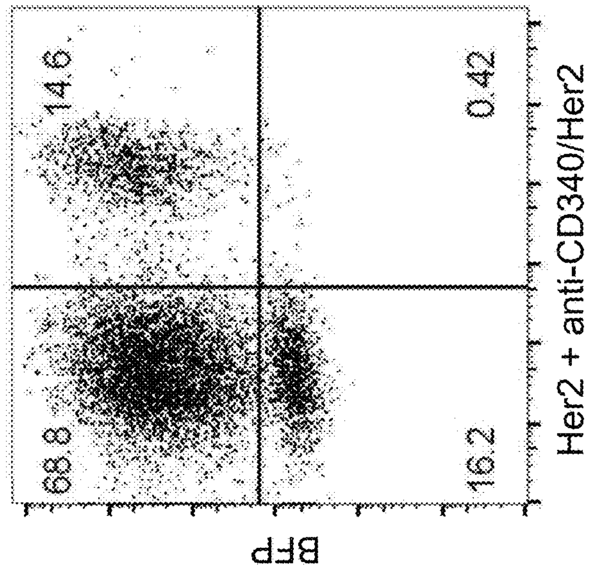

As shown in FIGS. 27A and 27B, sorted CD3KO-Her2CAR-εCS T cells showed negative to low CD3ε expression, positive Her2-specific CAR expression and positive BFP expression indicating the incorporation of the NFAT-driven CD3ε expression cassette.

Figures 28A, 28B:
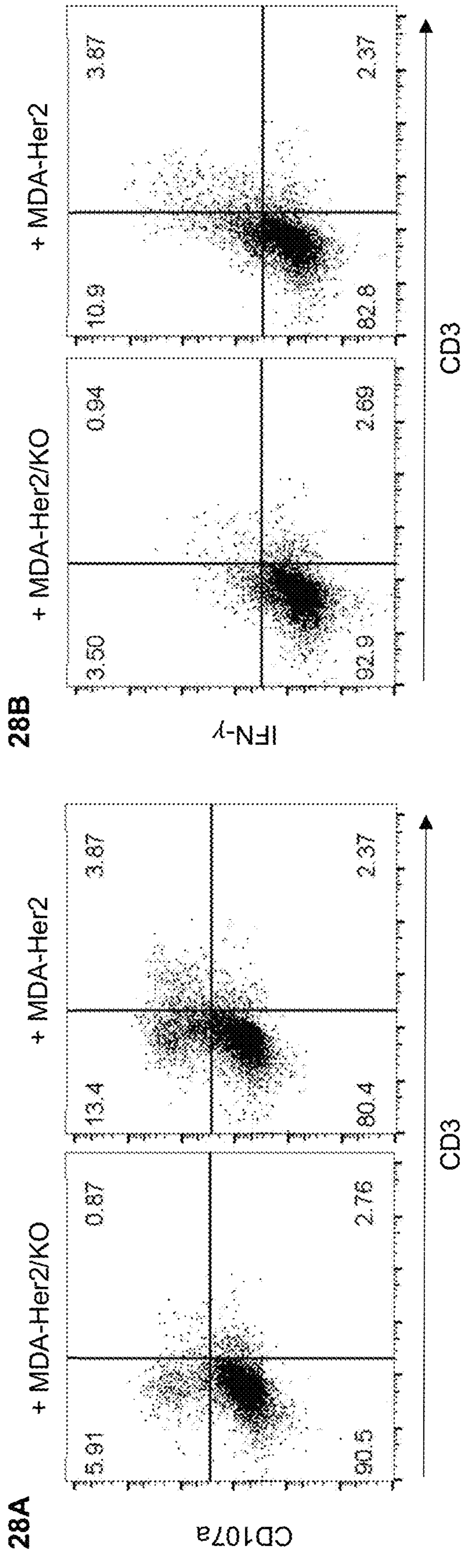
FIGS. 28A and 28B depict flow cytometry data illustrating that engagement of anti-Her2 CAR restores CD3 expression on CD3KO-Her2CAR-εCS T cells and enables the cells to activate in response to anti-CD3 antibody stimulation in terms of degranulation (CD107a) (A) and IFNγ production (B). Cells were gated on $BFP^+$ population.

Example 21: Engagement of Anti-Her2 CAR Restored CD3ε Expression on CD3KO-Her2CAR-εCS T Cells CD3-KO T Cells and Enabled the Cells to Activate in Response to Anti-CD3 Stimulation To test the ability of CD3KO-Her2CAR-εCS T cells to restore CD3 expression and react to anti-CD3 stimulation, 200,000 CD3KO-Her2CAR-εCS T cells generated as described in Example 20 were stimulated for 16 hours with 80,000 MDA-MB-231 with the low levels of intrinsic Her2 expression knocked out (MDA-HerKO) or MDA-MB-231 cells transduced to express Her2 at high levels (MDA-Her2) (FIG. 23) in a 96-well tissue culture plate. The T cells were then transferred to a separate well containing anti-CD3/CD28 Dynabeads (Life Technologies) at a 1:1 bead to T cell ratio and incubated for 6 hours in the presence of monensin (Biolegend) and FITC-conjugated anti-human-CD107a antibody (Biolegend, clone H4A3). Beads were then removed, and the cells were fixed in 4% formaldehyde, permeabilized with permeabilization buffer (0.5% BSA, 0.1% saponin, in DPBS/azide), stained with anti-human-CD3 and anti-human-IFNγ (Biolegend clone 4S.B3) antibodies and analyzed using a NovoCyte Quanteon flow cytometer. The results showed that compared to CD3KO-Her2CAR-εCS T cells stimulated with MDA-Her2KO, CD3KO-Her2CAR-εCS T cells stimulated with MDA-Her2 had 50% more $CD3\varepsilon^+$ cells, 4.4-fold more $CD3\varepsilon^+CD107a^+$ T cells and 4.1-fold more $CD3\varepsilon^+INF\gamma^+$ cells. See FIGS. 28A and 28B. These data demonstrate that in response to Her2CAR engagement, CD3KO-Her2CAR-εCS T cells were able to restore the expression of CD3, which is capable of mediating T cell activation in response to anti-CD3 stimulation.

Example 22: In Vivo Functional Study of Tumor-Activated Alloreactive T Cells in NSG-HLA-A2/HHD Mouse Models Xenograft mouse tumor models will be used to determine the ability of tumor-activated alloreactive T cells to suppress the growth of tumors with homogenous and heterogeneous tumor antigen expressions. To evaluate potential normal tissue damages by tumor-activated alloreactive T cells, we will establish the models using MDA-MB-231 cells in NSG-HLA-A2/HHD mice (Jax, #014570), which are highly immunodeficient NSG mice expressing human HLA-A02 in addition to mouse MHC class I and class II molecules (81, 82). MD-MB-231 cells form rapidly growing tumors in NSG mice (83) and the xenograft models have been widely used for testing T cell therapies against cancers (84-86). It has been shown that the expression of HLA-A02 enhances GvHD caused by transplanted HLA-A02-human T cells due to the combined alloreactivity and xenoreactivity (87). The models therefore serve as a sensitive platform to investigate the potential normal tissue damages and GvHDs caused by tumor-activated alloreactive T cells, which are generated using T cells from $HLA\text{-}A02^-$ donors to target $HLA\text{-}A02^+$ MDA-MB-231 cells. CD3KO-Her2CAR-εCS and CD3KO-Her2SN-εCS tumor-activated alloreactive T cells generated through MDA-MB-231 stimulation or MoDC stimulation as described in Examples 16 and 20 will be tested.

1) Determine the ability of tumor-activated alloreactive T cells to suppress the growth of tumors with homogenous tumor antigen expression. To establish the xenograft mouse models, a group of NSG-HLA-A2/HHD mice will be injected subcutaneously into the right flank with $5\times10^6$ $Her2^+$ MDA-luci-Her2 cells. At day 7 after injection, $1\times10^6$ tumor-activated alloreactive T cells will be administered via tail vein injection. As negative controls, a group of mice will be treated with T cells activated with anti-CD3/CD28 beads (ThermoFisher) from the same donor for tumor-activated alloreactive T cells. To confirm that tumor suppression is due to the alloreactivities of tumor-activated alloreactive T cells, mice with tumors established using $Her2^+HLA^-$ MDA-β2m-KO-luci cells will be treated. Tumor progression will be evaluated weekly by measuring the size of the tumor with a caliper and by measuring luminescence emission on a Lumina LT IVIS in vivo imaging system (Perkin Elmer) after intraperitoneal injection of d-luciferin (GoldBio). The survival of the mice will be recorded over time for Kalan-Meier survival analysis.
2) Determine the ability of tumor-activated alloreactive T cells to suppress the growth of tumors with heterogenous tumor antigen expression and compare tumor-activated alloreactive T cells with CAR T cells for efficacy. Tumors will be established in NSG-HLA-A2/HHD mice using $Her2^+$ NIDA-MB-231 cells and $Her2^-$ MDA-luci-Her2KO cells mixed at 10:1, 1:1 and 1:10 ratios. Two groups of mice will be each treated with tumor-activated alloreactive T cells or the Her2-specific CAR T cells and tumor progression and mouse survival will be analyzed.
3) Determine the degree of normal tissue damage and GvHDs in mice treated with tumor-activated alloreactive T cells. A group of tumor-free NSG-HLA-A2/HHD mice and a group of NSG-HLA-A2/HHD mice carrying $Her2^+$ MDA-MB-231 tumors will be treated with tumor-activated alloreactive T cells as described above and monitored for GVHD over 6 months. As positive controls, the mice will be treated with expanded but unmanipulated alloreactive T cells or expanded alloreactive T cells expressing Her2-specific CARs. All tumor-activated alloreactive T cells, unmanipulated alloreactive T cells and CAR T cells will be generated with T cells from the same $HLA\text{-}A02^-$ donor. The severity of GVHD will be assessed three times a week by a scoring system that incorporates four clinical parameters: weight loss>10% of initial weight, hunching posture, skin lesions, dull fur, and diarrhea (88). Each of the five parameters will be scored 0 (if absent) or 1 (if present). Mice will be sacrificed in case of weight loss>30% of initial weight or upon reaching the maximal clinical grade (i.e., 5/5). In addition, histology analyses will be carried out on small and large bowel, liver, and skin samples of dead or sacrifice mice. Six parameters will be scored for small and large bowel and seven parameters for the liver as described by Cooke et al. (89). Three parameters will be scored for the skin according as described by Ferrara et al. (90). The presence of tumor-activated alloreactive T cells or CAR T cells in these tissues will also be recorded based on BFP expression and anti-CD3 staining, respectively.

The disclosures of each and every patent, patent application, and publication cited herein are hereby incorporated herein by reference in their entirety.

Although the present embodiments have been described in detail with reference to examples above, it is understood that various modifications can be made without departing from the spirit of these embodiments, and would readily be known to the skilled artisan. The appended Embodiments are intended to be construed to include all such embodiments and equivalent variations.

LIST OF REFERENCES

1. Porter D L, Levine B L, Kalos M, Bagg A, June C H. Chimeric antigen receptor-modified T cells in chronic lymphoid leukemia. N Engl J Med. 2011; 365(8):725-33. Epub 2011/08/13. doi: 10.1056/NEJMoa1103849. PubMed PMID: 21830940; PMCID: 3387277.
2. Kochenderfer J N, Dudley M E, Feldman S A, Wilson W H, Spaner D E, Maric I, Stetler-Stevenson M, Phan G Q, Hughes M S, Sherry R M, Yang J C, Kammula U S, Devillier L, Carpenter R, Nathan D A, Morgan R A, Laurencot C, Rosenberg S A. B-cell depletion and remissions of malignancy along with cytokine-associated toxicity in a clinical trial of anti-CD19 chimeric-antigen-receptor-transduced T cells. Blood. 2012; 119(12):2709-20. Epub 2011/12/14. doi: blood-2011-10-384388 [pii] 10.1182/blood-2011-10-384388. PubMed PMID: 22160384; PMCID: 3327450.
3. Grupp S A, Kalos M, Barrett D, Aplenc R, Porter D L, Rheingold S R, Teachey D T, Chew A, Hauck B, Wright J F, Milone M C, Levine B L, June C H. Chimeric antigen receptor-modified T cells for acute lymphoid leukemia. N Engl J Med. 2013; 368(16):1509-18. Epub 2013/03/27. doi: 10.1056/NEJMoa1215134. PubMed PMID: 23527958.
4. Brentjens R J, Davila M L, Riviere I, Park J, Wang X, Cowell L G, Bartido S, Stefanski J, Taylor C, Olszewska M, Borquez-Ojeda O, Qu J, Wasielewska T, He Q, Bernal Y, Rijo I V, Hedvat C, Kobos R, Curran K, Steinherz P, Jurcic J, Rosenblat T, Maslak P, Frattini M, Sadelain M. CD19-targeted T cells rapidly induce molecular remissions in adults with chemotherapy-refractory acute lymphoblastic leukemia. Sci Transl Med. 2013; 5(177): 177ra38. Epub 2013/03/22. doi: 5/177/177ra38 [pii] 10.1126/scitranslmed.3005930. PubMed PMID: 23515080.
5. Kochenderfer J N, Wilson W H, Janik J E, Dudley M E, Stetler-Stevenson M, Feldman S A, Maric I, Raffeld M, Nathan D A, Lanier B J, Morgan R A, Rosenberg S A. Eradication of B-lineage cells and regression of lymphoma in a patient treated with autologous T cells genetically engineered to recognize CD19. Blood. 2010; 116 (20):4099-102. Epub 2010/07/30. doi: blood-2010-04-281931 [pii] 10.1182/blood-2010-04-281931. PubMed PMID: 20668228; PMCID: 2993617.
6. Morgan R A, Yang J C, Kitano M, Dudley M E, Laurencot C M, Rosenberg S A. Case report of a serious adverse event following the administration of T cells transduced with a chimeric antigen receptor recognizing ERBB2. Mol Ther. 2010; 18(4):843-51. Epub 2010/02/25. doi: mt201024 [pii] 10.1038/mt.2010.24. PubMed PMID: 20179677; PMCID: 2862534.
7. Hosonaga M, Arima Y, Sampetrean O, Komura D, Koya I, Sasaki T, Sato E, Okano H, Kudoh J, Ishikawa S, Saya H, Ishikawa T. HER2 Heterogeneity Is Associated with Poor Survival in HER2-Positive Breast Cancer. Int J Mol Sci. 2018; 19(8). doi: 10.3390/ijms19082158. PubMed PMID: 30042341; PMCID: PMC6121890.
8. Fennemann F L, de Vries I J M, Figdor C G, Verdoes M. Attacking Tumors From All Sides: Personalized Multiplex Vaccines to Tackle Intratumor Heterogeneity. Front Immunol. 2019; 10:824. doi: 10.3389/fimmu.2019.00824. PubMed PMID: 31040852; PMCID: PMC6476980.
9. Fargion S, Carney D, Mulshine J, Rosen S, Bunn P, Jewett P, Cuttitta F, Gazdar A, Minna J. Heterogeneity of cell surface antigen expression of human small cell lung cancer detected by monoclonal antibodies. Cancer Res. 1986; 46(5):2633-8. PubMed PMID: 3008997.
10. O'Rourke D M, Nasrallah M P, Desai A, Melenhorst J J, Mansfield K, Morrissette J J D, Martinez-Lage M, Brem S, Maloney E, Shen A, Isaacs R, Mohan S, Plesa G, Lacey S F, Navenot J M, Zheng Z, Levine B L, Okada H, June C H, Brogdon J L, Maus M V. A single dose of peripherally infused EGFRvIII-directed CAR T cells mediates antigen loss and induces adaptive resistance in patients with recurrent glioblastoma. Sci Transl Med. 2017; 9(399). doi: 10.1126/scitranslmed.aaa0984. PubMed PMID: 28724573; PMCID: PMC5762203.
11. Liu X, Jiang S, Fang C, Yang S, Olalere D, Pequignot E C, Cogdill A P, Li N, Ramones M, Granda B, Zhou L, Loew A, Young R M, June C H, Zhao Y. Affinity-Tuned ErbB2 or EGFR Chimeric Antigen Receptor T Cells Exhibit an Increased Therapeutic Index against Tumors in Mice. Cancer Res. 2015; 75(17):3596-607. doi: 10.1158/0008-5472.CAN-15-0159. PubMed PMID: 26330166; PMCID: PMC4560113.
12. Kloss C C, Condomines M, Cartellieri M, Bachmann M, Sadelain M. Combinatorial antigen recognition with balanced signaling promotes selective tumor eradication by engineered T cells. Nat Biotechnol. 2013; 31(1):71-5. doi: 10.1038/nbt.2459. PubMed PMID: 23242161; PMCID: PMC5505184.
13. Wilkie S, van Schalkwyk M C, Hobbs S, Davies D M, van der Stegen S J, Pereira A C, Burbridge S E, Box C, Eccles S A, Maher J. Dual targeting of ErbB2 and MUC1 in breast cancer using chimeric antigen receptors engineered to provide complementary signaling. J Clin Immunol. 2012; 32(5):1059-70. doi: 10.1007/s10875-012-9689-9. PubMed PMID: 22526592.
14. Roybal K T, Rupp L J, Morsut L, Walker W J, McNally K A, Park J S, Lim W A. Precision Tumor Recognition by T Cells With Combinatorial Antigen-Sensing Circuits. Cell. 2016; 164(4):770-9. doi: 10.1016/j.cell.2016.01.011. PubMed PMID: 26830879; PMCID: PMC4752902.
15. Krenciute G, Prinzing B L, Yi Z, Wu M F, Liu H, Dotti G, Balyasnikova I V, Gottschalk S. Transgenic Expression of IL15 Improves Antiglioma Activity of IL13Ralpha2-CAR T Cells but Results in Antigen Loss Variants. Cancer Immunol Res. 2017; 5(7):571-81. doi: 10.1158/2326-6066.CIR-16-0376. PubMed PMID: 28550091; PMCID: PMC5746871.

16. Cummins K D, Gill S. Chimeric antigen receptor T-cell therapy for acute myeloid leukemia: how close to reality? Haematologica. 2019; 104(7):1302-8. doi: 10.3324/haematol.2018.208751. PubMed PMID: 31221785; PMCID: PMC6601074.
17. Ehninger A, Kramer M, Rollig C, Thiede C, Bornhauser M, von Bonin M, Wermke M, Feldmann A, Bachmann M, Ehninger G, Oelschlagel U. Distribution and levels of cell surface expression of CD33 and CD123 in acute myeloid leukemia. Blood Cancer J. 2014; 4:e218. doi: 10.1038/bcj.2014.39. PubMed PMID: 24927407; PMCID: PMC4080210.
18. Testa U, Pelosi E, Frankel A. CD 123 is a membrane biomarker and a therapeutic target in hematologic malignancies. Biomark Res. 2014; 2(1):4. doi: 10.1186/2050-7771-2-4. PubMed PMID: 24513123; PMCID: PMC3928610.
19. Friedman K M, Garrett T E, Evans J W, Horton H M, Latimer H J, Seidel S L, Horvath C J, Morgan R A. Effective Targeting of Multiple B-Cell Maturation Antigen-Expressing Hematological Malignances by Anti-B-Cell Maturation Antigen Chimeric Antigen Receptor T Cells. Hum Gene Ther. 2018; 29(5):585-601. doi: 10.1089/hum.2018.001. PubMed PMID: 29641319; PMCID: PMC5930946.
20. Gaida M M, Welsch T, Herpel E, Tschaharganeh D F, Fischer L, Schirmacher P, Hansch G M, Bergmann F. MEW class II expression in pancreatic tumors: a link to intratumoral inflammation. Virchows Arch. 2012; 460(1): 47-60. doi: 10.1007/s00428-011-1175-x. PubMed PMID: 22120497.
21. Suchin E J, Langmuir P B, Palmer E, Sayegh M H, Wells A D, Turka L A. Quantifying the frequency of alloreactive T cells in vivo: new answers to an old question. J Immunol. 2001; 166(2):973-81. doi: 10.4049/jimmunol.166.2.973. PubMed PMID: 11145675.
22. DeWolf S, Grinshpun B, Savage T, Lau S P, Obradovic A, Shonts B, Yang S, Morris H, Zuber J, Winchester R, Sykes M, Shen Y. Quantifying size and diversity of the human T cell alloresponse. JCI Insight. 2018; 3(15). doi: 10.1172/jci.insight.121256. PubMed PMID: 30089728; PMCID: PMC6129121.
23. Heeger P S. T-cell allorecognition and transplant rejection: a summary and update. Am J Transplant. 2003; 3(5):525-33. doi: 10.1034/j.1600-6143.2003.00123.x. PubMed PMID: 12752308.
24. Shlomchik W D. Graft-versus-host disease. Nat Rev Immunol. 2007; 7(5):340-52. doi: 10.1038/nri2000. PubMed PMID: 17438575.
25. Lee S J, Klein J, Haagenson M, Baxter-Lowe L A, Confer D L, Eapen M, Fernandez-Vina M, Flomenberg N, Horowitz M, Hurley C K, Noreen H, Oudshoorn M, Petersdorf E, Setterholm M, Spellman S, Weisdorf D, Williams T M, Anasetti C. High-resolution donor-recipient HLA matching contributes to the success of unrelated donor marrow transplantation. Blood. 2007; 110(13): 4576-83. doi: 10.1182/blood-2007-06-097386. PubMed PMID: 17785583.
26. Tahara H, Ide K, Basnet N, Tanaka Y, Ohdan H. Determination of the precursor frequency and the reaction intensity of xenoreactive human T lymphocytes. Xenotransplantation. 2010; 17(3):188-96. doi: 10.1111/j.1399-3089.2010.00575.x. PubMed PMID: 20636539.
27. Kolb H J, Schmid C, Barrett A J, Schendel D J. Graft-versus-leukemia reactions in allogeneic chimeras. Blood. 2004; 103(3):767-76. doi: 10.1182/blood-2003-02-0342. PubMed PMID: 12958064.
28. Scarisbrick J J, Dignan F L, Tulpule S, Gupta E D, Kolade S, Shaw B, Evison F, Shah G, Tholouli E, Mufti G, Pagliuca A, Malladi R, Raj K. A multicentre UK study of GVHD following DLI: rates of GVHD are high but mortality from GVHD is infrequent. Bone Marrow Transplant. 2015; 50(1):62-7. doi: 10.1038/bmt.2014.227. PubMed PMID: 25310308.
29. Marcus A, Eshhar Z. Allogeneic adoptive cell transfer therapy as a potent universal treatment for cancer. Oncotarget. 2011; 2(7):525-6. doi: 10.18632/oncotarget.300. PubMed PMID: 21719916; PMCID: PMC3248176.
30. Ren J, Liu X, Fang C, Jiang S, June C H, Zhao Y. Multiplex Genome Editing to Generate Universal CAR T Cells Resistant to PD1 Inhibition. Clin Cancer Res. 2017; 23(9):2255-66. doi: 10.1158/1078-0432.CCR-16-1300. PubMed PMID: 27815355; PMCID: PMC5413401.
31. Torikai H, Reik A, Soldner F, Warren E H, Yuen C, Zhou Y, Crossland D L, Huls H, Littman N, Zhang Z, Tykodi S S, Kebriaei P, Lee D A, Miller J C, Rebar E J, Holmes M C, Jaenisch R, Champlin R E, Gregory P D, Cooper L J. Toward eliminating HLA class I expression to generate universal cells from allogeneic donors. Blood. 2013; 122(8):1341-9. doi: 10.1182/blood-2013-03-478255. PubMed PMID: 23741009; PMCID: PMC3750336.
32. Gornalusse G G, Hirata R K, Funk S E, Riolobos L, Lopes V S, Manske G, Prunkard D, Colunga A G, Hanafi L A, Clegg D O, Turtle C, Russell D W. HLA-E-expressing pluripotent stem cells escape allogeneic responses and lysis by NK cells. Nat Biotechnol. 2017; 35(8):765-72. doi: 10.1038/nbt.3860. PubMed PMID: 28504668; PMCID: PMC5548598.
33. Bach F, Hirschhorn K. Lymphocyte Interaction: A Potential Histocompatibility Test in Vitro. Science. 1964; 143 (3608):813-4. doi: 10.1126/science.143.3608.813. PubMed PMID: 14088078.
34. Thurner B, Roder C, Dieckmann D, Heuer M, Kruse M, Glaser A, Keikavoussi P, Kampgen E, Bender A, Schuler G. Generation of large numbers of fully mature and stable dendritic cells from leukapheresis products for clinical application. J Immunol Methods. 1999; 223(1):1-15. doi: 10.1016/s0022-1759(98)00208-7. PubMed PMID: 10037230.
35. Feuerstein B, Berger T G, Maczek C, Roder C, Schreiner D, Hirsch U, Haendle I, Leisgang W, Glaser A, Kuss O, Diepgen T L, Schuler G, Schuler-Thurner B. A method for the production of cryopreserved aliquots of antigen-preloaded, mature dendritic cells ready for clinical use. J Immunol Methods. 2000; 245(1-2):15-29. doi: 10.1016/s0022-1759(00)00269-6. PubMed PMID: 11042280.
36. Jonuleit H, Kuhn U, Muller G, Steinbrink K, Paragnik L, Schmitt E, Knop J, Enk A H. Pro-inflammatory cytokines and prostaglandins induce maturation of potent immunostimulatory dendritic cells under fetal calf serum-free conditions. Eur J Immunol. 1997; 27(12):3135-42. doi: 10.1002/eji.1830271209. PubMed PMID: 9464798.
37. Romani N, Gruner S, Brang D, Kampgen E, Lenz A, Trockenbacher B, Konwalinka G, Fritsch P O, Steinman R M, Schuler G. Proliferating dendritic cell progenitors in human blood. J Exp Med. 1994; 180(1):83-93. doi: 10.1084/jem.180.1.83. PubMed PMID: 8006603; PMCID: PMC2191538.
38. Bender A, Sapp M, Schuler G, Steinman R M, Bhardwaj N. Improved methods for the generation of dendritic cells from nonproliferating progenitors in human blood. J Immunol Methods. 1996; 196(2):121-35. doi: 10.1016/0022-1759(96)00079-8. PubMed PMID: 8841451.

39. Romani N, Reider D, Heuer M, Ebner S, Kampgen E, Eibl B, Niederwieser D, Schuler G. Generation of mature dendritic cells from human blood. An improved method with special regard to clinical applicability. J Immunol Methods. 1996; 196(2):137-51. doi: 10.1016/0022-1759(96)00078-6. PubMed PMID: 8841452.
40. Wu X, Xu F, Liu J, Wang G. Comparative study of dendritic cells matured by using IL-1beta, IL-6, TNF-alpha and prostaglandins E2 for different time span. Exp Ther Med. 2017; 14(2):1389-94. doi: 10.3892/etm.2017.4649. PubMed PMID: 28810601; PMCID: PMC5526128.
41. John J, Hutchinson J, Dalgleish A, Pandha H. Cryopreservation of immature monocyte-derived dendritic cells results in enhanced cell maturation but reduced endocytic activity and efficiency of adenoviral transduction. J Immunol Methods. 2003; 272(1-2):35-48. doi: 10.1016/s0022-1759(02)00430-1. PubMed PMID: 12505710.
42. Dauer M, Obermaier B, Herten J, Haerle C, Pohl K, Rothenfusser S, Schnurr M, Endres S, Eigler A. Mature dendritic cells derived from human monocytes within 48 hours: a novel strategy for dendritic cell differentiation from blood precursors. J Immunol. 2003; 170(8):4069-76. doi: 10.4049/jimmunol.170.8.4069. PubMed PMID: 12682236.
43. Cunningham S, Hackstein H. Recent Advances in Good Manufacturing Practice-Grade Generation of Dendritic Cells. Transfus Med Hemother. 2020; 47(6):454-63. doi: 10.1159/000512451. PubMed PMID: 33442340; PMCID: PMC7768120.
44. Hopewell E L, Cox C. Manufacturing Dendritic Cells for Immunotherapy: Monocyte Enrichment. Mol Ther Methods Clin Dev. 2020; 16:155-60. doi: 10.1016/j.omtm.2019.12.017. PubMed PMID: 32055643; PMCID: PMC7005329.
45. Hatfield P, Merrick A E, West E, O'Donnell D, Selby P, Vile R, Melcher A A. Optimization of dendritic cell loading with tumor cell lysates for cancer immunotherapy. J Immunother. 2008; 31(7):620-32. doi: 10.1097/CJI.0b013e31818213df. PubMed PMID: 18600182; PMCID: PMC3901408.
46. Reyes D, Salazar L, Espinoza E, Pereda C, Castellon E, Valdevenito R, Huidobro C, Ines Becker M, Lladser A, Lopez M N, Salazar-Onfray F. Tumour cell lysate-loaded dendritic cell vaccine induces biochemical and memory immune response in castration-resistant prostate cancer patients. Br J Cancer. 2013; 109(6):1488-97. doi: 10.1038/bjc.2013.494. PubMed PMID: 23989944; PMCID: PMC3777003.
47. Gonzalez F E, Gleisner A, Falcon-Beas F, Osorio F, Lopez M N, Salazar-Onfray F. Tumor cell lysates as immunogenic sources for cancer vaccine design. Hum Vaccin Immunother. 2014; 10(11):3261-9. doi: 10.4161/21645515.2014.982996. PubMed PMID: 25625929; PMCID: PMC4514089.
48. Gaj T, Sirk S J, Shui S L, Liu J. Genome-Editing Technologies: Principles and Applications. Cold Spring Harb Perspect Biol. 2016; 8(12). doi: 10.1101/cshperspect.a023754. PubMed PMID: 27908936; PMCID: PMC5131771.
49. Hirakawa M P, Krishnakumar R, Timlin J A, Carney J P, Butler K S. Gene editing and CRISPR in the clinic: current and future perspectives. Biosci Rep. 2020; 40(4). doi: 10.1042/BSR20200127. PubMed PMID: 32207531; PMCID: PMC7146048.
50. Bailey S R, Maus M V. Gene editing for immune cell therapies. Nat Biotechnol. 2019; 37(12):1425-34. doi: 10.1038/s41587-019-0137-8. PubMed PMID: 31160723.
51. Osborn M J, Webber B R, Knipping F, Lonetree C L, Tennis N, DeFeo A P, McElroy A N, Starker C G, Lee C, Merkel S, Lund T C, Kelly-Spratt K S, Jensen M C, Voytas D F, von Kalle C, Schmidt M, Gabriel R, Hippen K L, Miller J S, Scharenberg A M, Tolar J, Blazar B R. Evaluation of TCR Gene Editing Achieved by TALENs, CRISPR/Cas9, and megaTAL Nucleases. Mol Ther. 2016; 24(3):570-81. doi: 10.1038/mt.2015.197. PubMed PMID: 26502778; PMCID: PMC4786913.
52. Choi B D, Yu X, Castano A P, Darr H, Henderson D B, Bouffard A A, Larson R C, Scarfo I, Bailey S R, Gerhard G M, Frigault M J, Leick M B, Schmidts A, Sagert J G, Curry W T, Carter B S, Maus M V. CRISPR-Cas9 disruption of PD-1 enhances activity of universal EGFRvIII CAR T cells in a preclinical model of human glioblastoma. J Immunother Cancer. 2019; 7(1):304. doi: 10.1186/s40425-019-0806-7. PubMed PMID: 31727131; PMCID: PMC6857271.
53. Nagarsheth N, Wicha M S, Zou W. Chemokines in the cancer microenvironment and their relevance in cancer immunotherapy. Nat Rev Immunol. 2017; 17(9):559-72. doi: 10.1038/nri.2017.49. PubMed PMID: 28555670; PMCID: PMC5731833.
54. Chesnokova V, Melmed S. Growth hormone in the tumor microenvironment. Arch Endocrinol Metab. 2019; 63(6): 568-75. doi: 10.20945/2359-3997000000186. PubMed PMID: 31939481; PMCID: PMC7025769.
55. Morsut L, Roybal K T, Xiong X, Gordley R M, Coyle S M, Thomson M, Lim W A. Engineering Customized Cell Sensing and Response Behaviors Using Synthetic Notch Receptors. Cell. 2016; 164(4):780-91. doi: 10.1016/j.cell.2016.01.012. PubMed PMID: 26830878; PMCID: PMC4752866.
56. Schwarz K A, Daringer N M, Dolberg T B, Leonard J N. Rewiring human cellular input-output using modular extracellular sensors. Nat Chem Biol. 2017; 13(2):202-9. doi: 10.1038/nchembio.2253. PubMed PMID: 27941759.
57. Barnea G, Strapps W, Herrada G, Berman Y, Ong J, Kloss B, Axel R, Lee K J. The genetic design of signaling cascades to record receptor activation. Proc Natl Acad Sci USA. 2008; 105(1):64-9. doi: 10.1073/pnas.0710487105. PubMed PMID: 18165312; PMCID: PMC2224232.
58. Chmielewski M, Abken H. CAR T cells transform to trucks: chimeric antigen receptor-redirected T cells engineered to deliver inducible IL-12 modulate the tumour stroma to combat cancer. Cancer Immunol Immunother. 2012; 61(8):1269-77. doi: 10.1007/s00262-012-1202-z. PubMed PMID: 22274776.
59. Liu Y, Di S, Shi B, Zhang H, Wang Y, Wu X, Luo H, Wang H, Li Z, Jiang H. Armored Inducible Expression of IL-12 Enhances Antitumor Activity of Glypican-3-Targeted Chimeric Antigen Receptor-Engineered T Cells in Hepatocellular Carcinoma. J Immunol. 2019; 203(1):198-207. doi: 10.4049/jimmunol.1800033. PubMed PMID: 31142602.
60. Chmielewski M, Abken H. CAR T Cells Releasing IL-18 Convert to T-Bet(high) FoxO1(low) Effectors that Exhibit Augmented Activity against Advanced Solid Tumors. Cell Rep. 2017; 21(11):3205-19. doi: 10.1016/j.celrep.2017.11.063. PubMed PMID: 29241547.
61. Clevers H, Alarcon B, Wileman T, Terhorst C. The T cell receptor/CD3 complex: a dynamic protein ensemble. Annu Rev Immunol. 1988; 6:629-62. doi: 10.1146/annurev.iy.06.040188.003213. PubMed PMID: 3289580.

62. Labrecque N, Whitfield L S, Obst R, Waltzinger C, Benoist C, Mathis D. How much TCR does a T cell need? Immunity. 2001; 15(1):71-82. doi: 10.1016/s1074-7613 (01)00170-4. PubMed PMID: 11485739.
63. Srivastava S, Salter A I, Liggitt D, Yechan-Gunja S, Sarvothama M, Cooper K, Smythe K S, Dudakov J A, Pierce R H, Rader C, Riddell S R. Logic-Gated ROR1 Chimeric Antigen Receptor Expression Rescues T Cell-Mediated Toxicity to Normal Tissues and Enables Selective Tumor Targeting. Cancer Cell. 2019; 35(3):489-503 e8. doi: 10.1016/j.ccell.2019.02.003. PubMed PMID: 30889382; PMCID: PMC6450658.
64. Choe J H, Watchmaker P B, Simic M S, Gilbert R D, Li A W, Krasnow N A, Downey K M, Yu W, Carrera D A, Celli A, Cho J, Briones J D, Duecker J M, Goretsky Y E, Dannenfelser R, Cardarelli L, Troyanskaya O, Sidhu S S, Roybal K T, Okada H, Lim W A. SynNotch-CAR T cells overcome challenges of specificity, heterogeneity, and persistence in treating glioblastoma. Sci Transl Med. 2021; 13(591). doi: 10.1126/scitranslmed.abe7378. PubMed PMID: 33910979; PMCID: PMC8362330.
65. Natsume T, Kanemaki M T. Conditional Degrons for Controlling Protein Expression at the Protein Level. Annu Rev Genet. 2017; 51:83-102. doi: 10.1146/annurev-genet-120116-024656. PubMed PMID: 29178817.
66. Ishigami S, Natsugoe S, Nakajo A, Arigami T, Kitazono M, Okumura H, Matsumoto M, Uchikado Y, Setoyama T, Sasaki K, Aikou T. HLA-class I expression in gastric cancer. J Surg Oncol. 2008; 97(7):605-8. doi: 10.1002/jso.21029. PubMed PMID: 18459158.
67. Mizukami Y, Kono K, Maruyama T, Watanabe M, Kawaguchi Y, Kamimura K, Fujii H. Downregulation of HLA Class I molecules in the tumour is associated with a poor prognosis in patients with oesophageal squamous cell carcinoma. Br J Cancer. 2008; 99(9):1462-7. doi: 10.1038/sj.bjc.6604715. PubMed PMID: 18841157; PMCID: PMC2579690.
68. Tsukahara T, Kawaguchi S, Torigoe T, Asanuma H, Nakazawa E, Shimozawa K, Nabeta Y, Kimura S, Kaya M, Nagoya S, Wada T, Yamashita T, Sato N. Prognostic significance of HLA class I expression in osteosarcoma defined by anti-pan HLA class I monoclonal antibody, EMR8-5. Cancer Sci. 2006; 97(12):1374-80. doi: 10.1111/j.1349-7006.2006.00317.x. PubMed PMID: 16995877.
69. Kaneko K, Ishigami S, Kijima Y, Funasako Y, Hirata M, Okumura H, Shinchi H, Koriyama C, Ueno S, Yoshinaka H, Natsugoe S. Clinical implication of HLA class I expression in breast cancer. BMC Cancer. 2011; 11:454. doi: 10.1186/1471-2407-11-454. PubMed PMID: 22014037; PMCID: PMC3214195.
70. Kikuchi E, Yamazaki K, Torigoe T, Cho Y, Miyamoto M, Oizumi S, Hommura F, Dosaka-Akita H, Nishimura M. HLA class I antigen expression is associated with a favorable prognosis in early stage non-small cell lung cancer. Cancer Sci. 2007; 98(9):1424-30. doi: 10.1111/j.1349-7006.2007.00558.x. PubMed PMID: 17645781.
71. Hanahan D, Coussens L M. Accessories to the crime: functions of cells recruited to the tumor microenvironment. Cancer Cell. 2012; 21(3):309-22. doi: 10.1016/j.ccr.2012.02.022. PubMed PMID: 22439926.
72. Veglia F, Perego M, Gabrilovich D. Myeloid-derived suppressor cells coming of age. Nat Immunol. 2018; 19(2):108-19. doi: 10.1038/s41590-017-0022-x. PubMed PMID: 29348500; PMCID: PMC5854158.
73. Park H S, Cho U, Im S Y, Yoo C Y, Jung J H, Suh Y J, Choi H J. Loss of Human Leukocyte Antigen Class I Expression Is Associated with Poor Prognosis in Patients with Advanced Breast Cancer. J Pathol Transl Med. 2019; 53(2):75-85. doi: 10.4132/jptm.2018.10.11. PubMed PMID: 30424591; PMCID: PMC6435992.
74. Cabrera T, Lopez-Nevot M A, Gaforio J J, Ruiz-Cabello F, Garrido F. Analysis of HLA expression in human tumor tissues. Cancer Immunol Immunother. 2003; 52(1):1-9. doi: 10.1007/s00262-002-0332-0. PubMed PMID: 12536234.
75. Connor M E, Stern P L. Loss of MHC class-I expression in cervical carcinomas. Int J Cancer. 1990; 46(6):1029-34. doi: 10.1002/ijc.2910460614. PubMed PMID: 2174412.
76. Okamoto M, Inaba T, Yamada N, Uchida R, Fuchida S I, Okano A, Shimazaki C, Taniwaki M. Expression and role of MHC class I-related chain in myeloma cells. Cytotherapy. 2006; 8(5):509-16. doi: 10.1080/14653240600957586. PubMed PMID: 17050256.
77. Campanelli R, Palermo B, Garbelli S, Mantovani S, Lucchi P, Necker A, Lantelme E, Giachino C. Human CD8 co-receptor is strictly involved in WIC-peptide tetramer-TCR binding and T cell activation. Int Immunol. 2002; 14(1):39-44. doi: 10.1093/intimm/14.1.39. PubMed PMID: 11751750.
78. Wooldridge L, Hutchinson S L, Choi E M, Lissina A, Jones E, Mirza F, Dunbar P R, Price D A, Cerundolo V, Sewell A K. Anti-CD8 antibodies can inhibit or enhance peptide-MHC class I (pMHCI) multimer binding: this is paralleled by their effects on CTL activation and occurs in the absence of an interaction between pMHCI and CD8 on the cell surface. J Immunol. 2003; 171(12):6650-60. doi: 10.4049/jimmunol.171.12.6650. PubMed PMID: 14662868.
79. Rozanov D V, Rozanov N D, Chiotti K E, Reddy A, Wilmarth P A, David L L, Cha S W, Woo S, Pevzner P, Bafna V, Burrows G G, Rantala J K, Levin T, Anur P, Johnson-Camacho K, Tabatabaei S, Munson D J, Bruno T C, Slansky J E, Kappler J W, Hirano N, Boegel S, Fox B A, Egelston C, Simons D L, Jimenez G, Lee P P, Gray J W, Spellman P T. MHC class I loaded ligands from breast cancer cell lines: A potential HLA-I-typed antigen collection. J Proteomics. 2018; 176:13-23. doi: 10.1016/j.jprot.2018.01.004. PubMed PMID: 29331515; PMCID: PMC5999401.
80. Scheinberg P, Price D A, Ambrozak D R, Barrett A J, Douek D C. Alloreactive T cell clonotype recruitment in a mixed lymphocyte reaction: implications for graft engineering. Exp Hematol. 2006; 34(6):788-95. doi: 10.1016/j.exphem.2006.03.001. PubMed PMID: 16728284.
81. Pascolo S, Bervas N, Ure J M, Smith A G, Lemonnier F A, Perarnau B. HLA-A2.1-restricted education and cytolytic activity of CD8(+) T lymphocytes from beta2 microglobulin (beta2m) HLA-A2.1 monochain transgenic H-2db beta2m double knockout mice. J Exp Med. 1997; 185(12):2043-51. doi: 10.1084/jem.185.12.2043. PubMed PMID: 9182675; PMCID: PMC2196346.
82. Shultz L D, Saito Y, Najima Y, Tanaka S, Ochi T, Tomizawa M, Doi T, Sone A, Suzuki N, Fujiwara H, Yasukawa M, Ishikawa F. Generation of functional human T-cell subsets with HLA-restricted immune responses in HLA class I expressing NOD/SCID/IL2r gamma(null) humanized mice. Proc Natl Acad Sci USA. 2010; 107 (29):13022-7. doi: 10.1073/pnas.1000475107. PubMed PMID: 20615947.
83. Iorns E, Drews-Elger K, Ward T M, Dean S, Clarke J, Berry D, El Ashry D, Lippman M. A new mouse model for the study of human breast cancer metastasis. PLoS One.

2012; 7(10):e47995. doi: 10.1371/journal.pone.0047995. PubMed PMID: 23118918; PMCID: PMC3485320.
84. Seitz C M, Schroeder S, Knopf P, Krahl A C, Hau J, Schleicher S, Martella M, Quintanilla-Martinez L, Kneilling M, Pichler B, Lang P, Atar D, Schilbach K, Handgretinger R, Schlegel P. GD2-targeted chimeric antigen receptor T cells prevent metastasis formation by elimination of breast cancer stem-like cells. Oncoimmunology. 2020; 9(1):1683345. doi: 10.1080/2162402X.2019.1683345. PubMed PMID: 32002293; PMCID: PMC6959445.
85. Wei H, Wang Z, Kuang Y, Wu Z, Zhao S, Zhang Z, Li H, Zheng M, Zhang N, Long C, Guo W, Nie C, Yang H, Tong A. Intercellular Adhesion Molecule-1 as Target for CAR-T-Cell Therapy of Triple-Negative Breast Cancer. Front Immunol. 2020; 11:573823. doi: 10.3389/fimmu.2020.573823. PubMed PMID: 33072116; PMCID: PMC7539633.
86. Han Y, Xie W, Song D G, Powell D J, Jr. Control of triple-negative breast cancer using ex vivo self-enriched, costimulated NKG2D CART cells. J Hematol Oncol. 2018; 11(1):92. doi: 10.1186/s13045-018-0635-z. PubMed PMID: 29980239; PMCID: PMC6035420.
87. Ehx G, Somja J, Warnatz H J, Ritacco C, Hannon M, Delens L, Fransolet G, Delvenne P, Muller J, Beguin Y, Lehrach H, Belle L, Humblet-Baron S, Baron F. Xenogeneic Graft-Versus-Host Disease in Humanized NSG and NSG-HLA-A2/HHD Mice. Front Immunol. 2018; 9:1943. doi: 10.3389/fimmu.2018.01943. PubMed PMID: 30214443; PMCID: PMC6125392.
88. Naserian S, Leclerc M, Thiolat A, Pilon C, Le Bret C, Belkacemi Y, Maury S, Charlotte F, Cohen J L. Simple, Reproducible, and Efficient Clinical Grading System for Murine Models of Acute Graft-versus-Host Disease. Front Immunol. 2018; 9:10. doi: 10.3389/fimmu.2018.00010. PubMed PMID: 29403494; PMCID: PMC5786520.
89. Cooke K R, Hill G R, Crawford J M, Bungard D, Brinson Y S, Delmonte J, Jr., Ferrara J L. Tumor necrosis factor-alpha production to lipopolysaccharide stimulation by donor cells predicts the severity of experimental acute graft-versus-host disease. J Clin Invest. 1998; 102(10):1882-91. doi: 10.1172/JCI4285. PubMed PMID: 9819375; PMCID: PMC509139.
90. Ferrara J, Guillen F J, Sleckman B, Burakoff S J, Murphy G F. Cutaneous acute graft-versus-host disease to minor histocompatibility antigens in a murine model: histologic analysis and correlation to clinical disease. J Invest Dermatol. 1986; 86(4):371-5. doi: 10.1111/1523-1747.ep12285612. PubMed PMID: 3528309.

What is claimed is:

1. A genetically modified alloreactive or xenoreactive T cell comprising:

(i) genetic disruption of expression of at least one endogenous gene encoding a molecule necessary for T cell receptor (TCR) signaling and T cell activation, (ii) an exogenous nucleotide sequence encoding a tumor-sensing receptor that releases or activates a transcription activator in response to direct or indirect binding to molecules enriched on tumor cells, present in the tumor microenvironment or present in tissues with blood cancer cell accumulation, and (iii) an exogenous nucleotide sequence comprising an expression cassette that expresses a restorative copy of the disrupted endogenous gene of (i) in response to the released or activated transcription activator of (ii), wherein the genetically modified T cell is alloreactive or xenoreactive.

2. The genetically modified T cell of claim 1, wherein the at least one disrupted endogenous gene encoding a molecule necessary for TCR signaling and T cell activation encodes a transmembrane protein selected from CD3ε, CD3ζ, CD3γ, CD3δ, CD4, CD8α, CD8β, LAT, TRIM, CD45, CD28, LFA-1, CD2, CD54, CD52, CD148, and CD58, or encodes an intracellular signaling molecule chosen from Lck, Zap70, calcineurin, PI3K, Fyn, PLCγ, SLP76, PKCθ, AKT, and PDK1.

3. The genetically modified T cell of claim 1, wherein the tumor-sensing receptor comprises (i) an extracellular domain that binds directly or indirectly to a target molecule enriched on or in at least one of tumor cells, tumor microenvironment, and tissues with blood cancer cell accumulation; and (ii) an intracellular domain that activates or releases a transcription activator in response to extracellular domain binding to the target molecule.

4. The genetically modified T cell of claim 3, wherein the tumor-sensing receptor is a Synthetic Notch (SynNotch) receptor, a Modular Extracellular Sensor Architecture (MESA) receptor, or a Tango receptor, and wherein an intracellular transcription activator is released from the receptor in response to extracellular domain binding to the target molecule.

5. The genetically modified T cell of claim 3, wherein the tumor-sensing receptor is a chimeric antigen receptor (CAR) with intracellular ITAM domains, wherein an endogenous transcription factor is activated through signaling pathways in response to extracellular domain binding to the target molecule.

6. The genetically modified T cell of claim 1, wherein the extracellular domain of the tumor-sensing receptor is a single chain variable fragment (scFv), a Fab fragment, a designed ankyrin repeat protein (DARPin), a TCR, a nanobody, a Fc receptor, a growth factor receptor, a chemokine receptor, or a hormone receptor.

7. The genetically modified T cell of claim 3, wherein the target molecule is enriched on tumor cells and/or in the tumor microenvironment and is chosen from CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvlll, vascular endothelial growth factor receptor-2 (VEGFR2), high molecular weight-melanoma associated antigen (HMW-MAA), MAGE-A1, IL-13R-a2, GD2, 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (lgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, FAP, fibronectin extra domain-B, folate receptor 1, GD2, GD3 ganglioside, glycoprotein 75, GPNMB, HGF, human scatter factor receptor kinase, IGF-1 receptor, IGF-I, IgGI, LI-CAM, IL-13, IL-6, insulin-like growth factor I receptor, integrin αvβ3, MORAb-009, MS4A1, MUC1, mucin CanAg, N-glycolylneuraminic acid, NPC-IC, PDGF-Ra, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-RI, TRAIL-R2, tumor antigen CTAA16.88, VEGF-A, VEGFR-1, VEGFR2, mesothelin, NKG2D, CD147, NKR2, B7H3, and vimentin, or wherein the target molecule is enriched in a tissue with blood cancer cell accumulation, wherein the tissue is lymphoid and/or bone marrow tissue, and wherein the target molecule is chosen from CD45, CD19, CD20, CD4, CD8, CD2, CCR4, CD58, CD28, CD23, CD69, CD25, CD33, CD123 and CCL-1.

8. The genetically modified T cell of claim 1, wherein the expression cassette comprises a transcription control element operably linked to a copy of the disrupted gene of claim 1(ii), wherein the expression of the disrupted gene is driven by the binding of the transcription control unit by a transcription activator selected from the group consisting of Gal4-VP64, Notch, tet transactivator, NFAT, AP-1, NFκB/Rel, NR4A1 (Nur77), T-Bet, IRF4, STATs and eomesodermin (Eomes).

9. A method for producing the tumor-activated alloreactive or xenoreactive T cells according to claim 1, said method comprising:

a) selecting a sample of T cells from a donor individual, or from a donor animal;

b) optionally stimulating the sample of T cells to proliferate;

c) abrogating the expression or function of at least one molecule necessary for TCR signaling and T cell activation in the T cells to render the T cells activation-incompetent; and d) modifying the T cells to (i) express a recombinant receptor that specifically binds to a target molecule enriched on or in at least one of tumor cells, tumor microenvironment, and a tissue with blood cancer cell accumulation, wherein binding of the recombinant receptor with the target molecule releases or activates a transcription activator; and (ii) introduce an expression cassette that enables the transcription activator in (i) to drive the expression of the molecule abrogated in c), thereby restores the expression or function of the abrogated molecule, and thereby restores the ability of the T cells to activate through antigen recognition by TCR, thereby producing tumor-activated alloreactive or xenoreactive T cells.

10. The method of claim 9, wherein step d) is performed before step c), step c) is performed before step d), or steps c) and d) are performed at the same time.

11. The method of claim 9, wherein the sample of T cells is from a donor individual, and wherein the donor individual has at least one HLA allele mismatch relative to an intended recipient and the at least one HLA allele mismatch is located in a locus selected from the group consisting of: HLA-A, HLA-B, HLA-C, HLA-DRB1, HLA-DQA1, HLA-DQB1, HLA-DPA1 and HLA-DPB1.

12. The method of claim 9, wherein step b) comprises: (i) co-culturing donor T cells with cells from an intended recipient; (ii) co-culturing donor T cells with cells from a second donor that (1) has at least one HLA allele matched with the intended recipient, and (2) is mismatched with the T cell donor; (3) co-culturing donor T cells with at least one cell line expressing a least one HLA allele of the intended recipient; (4) co-culturing donor T cells with an artificial surface coated with at least one protein encoded by at least one HLA allele of the intended recipient.

13. The method of claim 9, wherein the at least one molecule necessary for TCR signaling and T cell activation is a cell surface molecule chosen from CD38, CD37, CD3y, CD30, CD4, CD8a, CD8B, LAT, TRIM, CD45, CD28, LFA-1, CD2,CD54, CD52, CD148, and CD58, or an intracellular signaling molecule chosen from Lck, Zap70, calcineurin, PI3K, Fyn, PLCy, SLP76, PKCO, AKT, and PDK1.

14. The method of claim 9, wherein step d) comprises introducing a nucleic acid encoding a tumor-sensing receptor into T cells, wherein the tumor-sensing receptor comprises (i) an extracellular domain that binds directly or indirectly to a target molecule enriched on or in at least one of tumor cells, tumor microenvironment, and tissues with blood cancer cell accumulation; and (ii) an intracellular domain that activates or releases a transcription activator in response to extracellular domain binding to the target molecule.

15. The method of claim 14, wherein the tumor-sensing receptor is a Synthetic Notch (SynNotch) receptor, a Modular Extracellular Sensor Architecture (MESA) receptor, or a Tango receptor, and wherein an intracellular transcription activator is released from the receptor in response to extracellular domain binding to the target molecule.

16. The method of claim 14, wherein the tumor-sensing receptor is a chimeric antigen receptor (CAR) with intracellular ITAM domains, wherein an endogenous transcription factor is activated through signaling pathways activated in response to extracellular domain binding to the target molecule.

17. The method of claim 9, where in the tumor-sensing receptor is a single chain variable fragment (scFv), a Fab fragment, a designed ankyrin repeat protein (DARPin), a nanobody, a TCR, a Fc receptor, a growth factor receptor, a chemokine receptor, or a hormone receptor.

18. The method of claim 9, wherein the target molecule is enriched on tumor cells and/or in the tumor microenvironment and is chosen from CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvlll, vascular endothelial growth factor receptor-2 (VEGFR2), high molecular weight-melanoma associated antigen (HMW-MAA), MAGE-A1, IL-13R-a2, GD2, 4-1BB, 5T4,adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200,CD22, CD221, CD23 (lgE receptor), CD28, CD30 (TNFRSF8), CD33, CD4, CD40,CD44 v6, CD51, CD52, CD56, CD74, CD80, CEA, CNT0888, CTLA-4, DRS, EGFR, EpCAM, FAP, fibronectin extra domain-B, folate receptor 1, GD2, GD3 ganglioside, glycoprotein 75, GPNMB, HGF, human scatter factor receptor kinase, IGF-1 receptor, IGF-I, IgGI, LI-CAM, IL-13, IL-6, insulin-like growth factor I receptor, integrin avß3,MORAb-009, MS4A1, MUC1, mucin CanAg, N-glycolylneuraminic acid, NPC-IC, PDGF-Ra, PDL192, phosphatidylserine, prostatic carcinoma cells, RANKL, RON, ROR1, SCH 900105, SDC1, SLAMF7, TAG-72, tenascin C, TGF beta 2, TGF-ß, TRAIL-RI, TRAIL-R2, tumor antigen CTAA16.88, VEGF-A, VEGFR-1, VEGFR2, mesothelin, NKG2D, CD147, NKR2, B7H3, and vimentin, or wherein the target molecule is enriched in a tissue with blood cancer cell accumulation, wherein the tissue is lymphoid and/or bone marrow tissue, and wherein the target molecule is chosen from CD45, CD19, CD20, CD4, CD8, CD2, CCR4, CD58, CD28,CD23, CD69, CD25, CD33, CD123 and CCL-1.

19. The method of claim 9, wherein step d) comprises introducing an expression cassette comprising a transcription control element operably linked to a copy of the disrupted gene of claim 9c), wherein the expression of the disrupted gene is driven by the binding of the transcription control unit by a transcription activator selected from the group consisting of Gal4-VP64, Notch, tet transactivator, NFAT, AP-1, NFKB/Rel, NR4A1 (Nur77), T-Bet, IRF4, STATs and eomesodermin (Eomes).

20. A method of treating cancer in a patient by administering T cells of claim 1.

* * * * *

SEQUENCE LISTING

```
<160> NUMBER OF SEQ ID NOS: 23

<210> SEQ ID NO 1
<211> LENGTH: 2219
<212> TYPE: DNA
<213> ORGANISM: Artificial Sequence
<220> FEATURE:
<223> OTHER INFORMATION: Synthetic Construct (Gal4-CD3-PGK-BFP)

<400> SEQUENCE: 1

cggagcactg tcctccgaac gtcggagcac tgtcctccga acgtcggagc actgtcctcc      60

gaacgtcgga gcactgtcct ccgaacggag catgtcctcc gaacgtcgga gcactgtcct     120

ccgaacgact agttaggcgt gtacggtggg aggcctatat aagcagagct cgtttagtga     180

accgtcagat cgcctggaga cgccatccac gctgttttga cctccataga agacaccggg     240

accgatccag cctctcgaca ttcgttgcat atggccacca tgcagagtgg gactcattgg     300

agagttttgg gcctgtgcct tctctcagtt ggcgtctggg ggcaggatgg aaacgaggaa     360

atgggaggta taacgcaaac accctacaaa gtctcaatat ccggaacgac ggttattttg     420

acatgccccc agtatccggg ctcagagatt ttgtggcagc ataacgataa aaatatcggg     480

ggcgatgagg acgacaagaa tatcggctcc gatgaagatc atctcagtct gaaagaattt     540

tccgaattgg aacagagcgg atattacgta tgttaccctc gagggtctaa acccgaggat     600

gctaactttt acctttattt gcgcgctagg gtctgcgaaa actgcatgga gatggatgta     660

atgtcagtgg ctacaatagt catagtggat atatgcatta ccgggggact gttgcttctc     720

gtctattact ggtctaaaaa ccgaaaagct aaggctaagc ccgttactcg aggagcaggc     780

gctggtgggc ggcagagggg gcaaaataaa gagcgcccac caccagtgcc taatccggat     840

tacgagccca tacgcaaagg tcagcgggat ctctatagtg ggcttaacca gcgaagaatc     900

tgagcggccg ccttgacttg cggccggccg caactcccac ctgcaacatg cgtgactgac     960

tgaggccgcg actctagagt cgacctgcac gaggttaacg aattctaccg ggtaggggag    1020

gcgcttttcc caaggcagtc tggagcatgc gctttagcag ccccgctggg cacttggcgc    1080
```

```
tacacaagtg gcctctggcc tcgcacacat tccacatcca ccggtaggcg ccaaccggct   1140

ccgttctttg gtggcccctt cgcgccacct tctactcctc ccctagtcag gaagttcccc   1200

cccgccccgc agctcgcgtc gtgcaggacg tgacaaatgg aagtagcacg tctcactagt   1260

ctcgtgcaga tggacagcac cgctgagcaa tggaagcggg taggcctttg gggcagcggc   1320

caatagcagc tttgctcctt cgctttctgg gctcagaggc tgggaagggg tgggtccggg   1380

ggcgggctca ggggcggggc gggcgcccga aggtcctccg gaggcccggc attctgcacg   1440

cttcaaaagc gcacgtctgc cgcgctgttc tcctcttcct catctccggg cctttcgacc   1500

tgcagcccaa gcttaccatg agcgagctga ttaaggagaa catgcacatg aagctgtaca   1560

tggagggcac cgtggacaac catcacttca agtgcacatc cgagggcgaa ggcaagccct   1620

acgagggcac ccagaccatg agaatcaagg tggtcgaggg cggccctctc cccttcgcct   1680

tcgacatcct ggctactagc ttcctctacg gcagcaagac cttcatcaac cacacccagg   1740

gcatccccga cttcttcaag cagtccttcc ctgagggctt cacatgggag agagtcacca   1800

catacgaaga cgggggcgtg ctgaccgcta cccaggacac cagcctccag gacggctgcc   1860

tcatctacaa cgtcaagatc agaggggtga acttcacatc caacggccct gtgatgcaga   1920

agaaaacact cggctgggag gccttcaccg agacgctgta ccccgctgac ggcggcctgg   1980

aaggcagaaa cgacatggcc ctgaagctcg tgggcgggag ccatctgatc gcaaacatca   2040

agaccacata tagatccaag aaacccgcta agaacctcaa gatgcctggc gtctactatg   2100

tggactacag actggaaaga atcaaggagg ccaacaacga gacctacgtc gagcagcacg   2160

aggtggcagt ggccagatac tgcgacctcc ctagcaaact ggggcacaag cttaattaa    2219
```

<210> SEQ ID NO 2
<211> LENGTH: 2259
<212> TYPE: DNA
<213> ORGANISM: Artificial Sequence
<220> FEATURE:
<223> OTHER INFORMATION: Synthetic Construct (NFAT-CD3-PKG-BFP)

<400> SEQUENCE: 2

```
ggaggaaaaa ctgtttcata cagaaggcgt ggaggaaaaa ctgtttcata cagaaggcgt     60

ggaggaaaaa ctgtttcata cagaaggcgt ggaggaaaaa ctgtttcata cagaaggcgt    120

ggaggaaaaa ctgtttcata cagaaggcgt ggaggaaaaa ctgtttcata cagaaggcgt    180

ccccgggaca ttttgacacc cccataatat ttttccagaa ttaacagtat aaattgcatc    240

tcttgttcaa gagttcccta tcactctctt taatcactac tcacagtaac ctcaactcct    300

gaattcccat atggccacca tgcagagtgg gactcattgg agagttttgg gcctgtgcct    360

tctctcagtt ggcgtctggg ggcaggatgg aaacgaggaa atgggaggta taacgcaaac    420

accctacaaa gtctcaatat ccggaacgac ggttattttg acatgccccc agtatccggg    480

ctcagagatt ttgtggcagc ataacgataa aaatatcggg ggcgatgagg acgacaagaa    540

tatcggctcc gatgaagatc atctcagtct gaaagaattt tccgaattgg aacagagcgg    600

atattacgta tgttaccctc gagggtctaa acccgaggat gctaactttt acctttattt    660

gcgcgctagg gtctgcgaaa actgcatgga gatggatgta atgtcagtgg ctacaatagt    720

catagtggat atatgcatta ccgggggact gttgcttctc gtctattact ggtctaaaaa    780

ccgaaaagct aaggctaagc ccgttactcg aggagcaggc gctggtgggc ggcagagggg    840

gcaaaataaa gagcgcccac caccagtgcc taatccggat tacgagccca tacgcaaagg    900
```

```
tcagcgggat ctctatagtg ggcttaacca gcgaagaatc tgagcggccg ccttgacttg     960

cggccggccg caactcccac ctgcaacatg cgtgactgac tgaggccgcg actctagagt    1020

cgacctgcac gaggttaacg aattctaccg ggtaggggag gcgcttttcc caaggcagtc    1080

tggagcatgc gctttagcag ccccgctggg cacttggcgc tacacaagtg gcctctggcc    1140

tcgcacacat tccacatcca ccggtaggcg ccaaccggct ccgttctttg gtggcccctt    1200

cgcgccacct tctactcctc ccctagtcag gaagttcccc cccgccccgc agctcgcgtc    1260

gtgcaggacg tgacaaatgg aagtagcacg tctcactagt ctcgtgcaga tggacagcac    1320

cgctgagcaa tggaagcggg taggcctttg gggcagcggc caatagcagc tttgctcctt    1380

cgctttctgg gctcagaggc tgggaagggg tgggtccggg ggcgggctca ggggcggggc    1440

gggcgcccga aggtcctccg gaggcccggc attctgcacg cttcaaaagc gcacgtctgc    1500

cgcgctgttc tcctcttcct catctccggg cctttcgacc tgcagcccaa gcttaccatg    1560

agcgagctga ttaaggagaa catgcacatg aagctgtaca tggagggcac cgtggacaac    1620

catcacttca agtgcacatc cgagggcgaa ggcaagccct acgagggcac ccagaccatg    1680

agaatcaagg tggtcgaggg cggccctctc cccttcgcct tcgacatcct ggctactagc    1740

ttcctctacg gcagcaagac cttcatcaac cacacccagg gcatccccga cttcttcaag    1800

cagtccttcc ctgagggctt cacatgggag agagtcacca catacgaaga cgggggcgtg    1860

ctgaccgcta cccaggacac cagcctccag gacggctgcc tcatctacaa cgtcaagatc    1920

agaggggtga acttcacatc caacggccct gtgatgcaga agaaaacact cggctgggag    1980

gccttcaccg agacgctgta ccccgctgac ggcggcctgg aaggcagaaa cgacatggcc    2040

ctgaagctcg tgggcgggag ccatctgatc gcaaacatca agaccacata tagatccaag    2100

aaacccgcta agaacctcaa gatgcctggc gtctactatg tggactacag actggaaaga    2160

atcaaggagg ccaacaacga gacctacgtc gagcagcacg aggtggcagt ggccagatac    2220

tgcgacctcc ctagcaaact ggggcacaag cttaattaa                           2259
```

```
<210> SEQ ID NO 3
<211> LENGTH: 2164
<212> TYPE: DNA
<213> ORGANISM: Artificial Sequence
<220> FEATURE:
<223> OTHER INFORMATION: Synthetic Construct (AP1-CD3-PKG-BFP)

<400> SEQUENCE: 3

ttgagtcaag attgagtcat cgttgagtca gacttgagtc actattgagt caactttgag      60

tcatgcttga gtcagtattg agtcaccccg ggacattttg acacccccat aatatttttc     120

cagaattaac agtataaatt gcatctcttg ttcaagagtt ccctatcact ctctttaatc     180

actactcaca gtaacctcaa ctcctgaatt cccatatggc caccatgcag agtgggactc     240

attggagagt tttgggcctg tgccttctct cagttggcgt ctgggggcag gatggaaacg     300

aggaaatggg aggtataacg caaacaccct acaaagtctc aatatccgga acgacggtta     360

ttttgacatg cccccagtat ccgggctcag agattttgtg gcagcataac gataaaaata     420

tcgggggcga tgaggacgac aagaatatcg gctccgatga agatcatctc agtctgaaag     480

aattttccga attggaacag agcggatatt acgtatgtta ccctcgaggg tctaaacccg     540

aggatgctaa cttttacctt tatttgcgcg ctagggtctg cgaaaactgc atggagatgg     600

atgtaatgtc agtggctaca atagtcatag tggatatatg cattaccggg ggactgttgc     660

ttctcgtcta ttactggtct aaaaaccgaa aagctaaggc taagcccgtt actcgaggag     720
```

```
caggcgctgg tgggcggcag agggggcaaa ataaagagcg cccaccacca gtgcctaatc    780
cggattacga gcccatacgc aaaggtcagc gggatctcta tagtgggctt aaccagcgaa    840
gaatctgagc ggccgccttg acttgcggcc ggccgcaact cccacctgca acatgcgtga    900
ctgactgagg ccgcgactct agagtcgacc tgcacgaggt taacgaattc taccgggtag    960
gggaggcgct tttcccaagg cagtctggag catgcgcttt agcagccccg ctgggcactt   1020
ggcgctacac aagtggcctc tggcctcgca cacattccac atccaccggt aggcgccaac   1080
cggctccgtt ctttggtggc cccttcgcgc caccttctac tcctccccta gtcaggaagt   1140
tcccccccgc cccgcagctc gcgtcgtgca ggacgtgaca aatggaagta gcacgtctca   1200
ctagtctcgt gcagatggac agcaccgctg agcaatggaa gcgggtaggc ctttggggca   1260
gcggccaata gcagctttgc tccttcgctt tctgggctca gaggctggga aggggtgggt   1320
ccgggggcgg gctcaggggc ggggcgggcg cccgaaggtc ctccggaggc ccggcattct   1380
gcacgcttca aaagcgcacg tctgccgcgc tgttctcctc ttcctcatct ccgggccttt   1440
cgacctgcag cccaagctta ccatgagcga gctgattaag gagaacatgc acatgaagct   1500
gtacatggag ggcaccgtgg acaaccatca cttcaagtgc acatccgagg gcgaaggcaa   1560
gccctacgag ggcacccaga ccatgagaat caaggtggtc gagggcggcc ctctcccctt   1620
cgccttcgac atcctggcta ctagcttcct ctacggcagc aagaccttca tcaaccacac   1680
ccagggcatc cccgacttct tcaagcagtc cttccctgag ggcttcacat gggagagagt   1740
caccacatac gaagacgggg gcgtgctgac cgctacccag gacaccagcc tccaggacgg   1800
ctgcctcatc tacaacgtca agatcagagg ggtgaacttc acatccaacg gccctgtgat   1860
gcagaagaaa acactcggct gggaggcctt caccgagacg ctgtaccccg ctgacggcgg   1920
cctggaaggc agaaacgaca tggccctgaa gctcgtgggc gggagccatc tgatcgcaaa   1980
catcaagacc acatatagat ccaagaaacc cgctaagaac ctcaagatgc ctggcgtcta   2040
ctatgtggac tacagactgg aaagaatcaa ggaggccaac aacgagacct acgtcgagca   2100
gcacgaggtg gcagtggcca gatactgcga cctccctagc aaactggggc acaagcttaa   2160
ttaa                                                                2164
```

<210> SEQ ID NO 4
<211> LENGTH: 2198
<212> TYPE: DNA
<213> ORGANISM: Artificial Sequence
<220> FEATURE:
<223> OTHER INFORMATION: Synthetic Construct (NFkB-CD3-PKG-BFP)

<400> SEQUENCE: 4

```
ggggaaattc ccctagaggg gaaattcccc ttcgggggaa attcccctga cggggaaatt     60
cccctctagg ggaaattccc ctactgggga aattcccctt gcggggaaat tcccctgtac    120
cccgggacat tttgacaccc ccataatatt tttccagaat taacagtata aattgcatct    180
cttgttcaag agttccctat cactctcttt aatcactact cacagtaacc tcaactcctg    240
aattcccata tggccaccat gcagagtggg actcattgga gagttttggg cctgtgcctt    300
ctctcagttg gcgtctgggg gcaggatgga aacgaggaaa tgggaggtat aacgcaaaca    360
ccctacaaag tctcaatatc cggaacgacg gttattttga catgccccca gtatccgggc    420
tcagagattt tgtggcagca taacgataaa aatatcgggg gcgatgagga cgacaagaat    480
atcggctccg atgaagatca tctcagtctg aaagaatttt ccgaattgga acagagcgga    540
```

```
tattacgtat gttaccctcg agggtctaaa cccgaggatg ctaactttta cctttatttg    600
cgcgctaggg tctgcgaaaa ctgcatggag atggatgtaa tgtcagtggc tacaatagtc    660
atagtggata tatgcattac cgggggactg ttgcttctcg tctattactg gtctaaaaac    720
cgaaaagcta aggctaagcc cgttactcga ggagcaggcg ctggtgggcg gcagaggggg    780
caaaataaag agcgcccacc accagtgcct aatccggatt acgagcccat acgcaaaggt    840
cagcgggatc tctatagtgg gcttaaccag cgaagaatct gagcggccgc cttgacttgc    900
ggccggccgc aactcccacc tgcaacatgc gtgactgact gaggccgcga ctctagagtc    960
gacctgcacg aggttaacga attctaccgg gtaggggagg cgcttttccc aaggcagtct   1020
ggagcatgcg ctttagcagc cccgctgggc acttggcgct acacaagtgg cctctggcct   1080
cgcacacatt ccacatccac cggtaggcgc caaccggctc cgttctttgg tggccccttc   1140
gcgccacctt ctactcctcc cctagtcagg aagttccccc ccgccccgca gctcgcgtcg   1200
tgcaggacgt gacaaatgga agtagcacgt ctcactagtc tcgtgcagat ggacagcacc   1260
gctgagcaat ggaagcgggt aggcctttgg ggcagcggcc aatagcagct ttgctccttc   1320
gctttctggg ctcagaggct gggaaggggt gggtccgggg gcgggctcag gggcggggcg   1380
ggcgcccgaa ggtcctccgg aggcccggca ttctgcacgc ttcaaaagcg cacgtctgcc   1440
gcgctgttct cctcttcctc atctccgggc ctttcgacct gcagcccaag cttaccatga   1500
gcgagctgat taaggagaac atgcacatga agctgtacat ggagggcacc gtggacaacc   1560
atcacttcaa gtgcacatcc gagggcgaag gcaagcccta cgagggcacc cagaccatga   1620
gaatcaaggt ggtcgagggc ggccctctcc ccttcgcctt cgacatcctg gctactagct   1680
tcctctacgg cagcaagacc ttcatcaacc acacccaggg catccccgac ttcttcaagc   1740
agtccttccc tgagggcttc acatgggaga gagtcaccac atacgaagac gggggcgtgc   1800
tgaccgctac ccaggacacc agcctccagg acggctgcct catctacaac gtcaagatca   1860
gaggggtgaa cttcacatcc aacggccctg tgatgcagaa gaaaacactc ggctgggagg   1920
ccttcaccga gacgctgtac cccgctgacg gcggcctgga aggcagaaac gacatggccc   1980
tgaagctcgt gggcgggagc catctgatcg caaacatcaa gaccacatat agatccaaga   2040
aacccgctaa gaacctcaag atgcctggcg tctactatgt ggactacaga ctggaaagaa   2100
tcaaggaggc caacaacgag acctacgtcg agcagcacga ggtggcagtg gccagatact   2160
gcgacctccc tagcaaactg ggcacaagc ttaattaa                            2198
```

<210> SEQ ID NO 5
<211> LENGTH: 2172
<212> TYPE: DNA
<213> ORGANISM: Artificial Sequence
<220> FEATURE:
<223> OTHER INFORMATION: Synthetic Construct (NR4A-CD3-PKG-BFP)

<400> SEQUENCE: 5

```
aaaggtcaca gaaaaggtca ctcgaaaggt cacgacaaag gtcacctaaa aggtcacact     60
aaaggtcact gcaaaggtca cgtaaaaggt cacccccggg acattttgac acccccataa    120
tatttttcca gaattaacag tataaattgc atctcttgtt caagagttcc ctatcactct    180
ctttaatcac tactcacagt aacctcaact cctgaattcc catatggcca ccatgcagag    240
tgggactcat tggagagttt tgggcctgtg ccttctctca gttggcgtct gggggcagga    300
tggaaacgag gaaatgggag gtataacgca aacaccctac aaagtctcaa tatccggaac    360
gacggttatt ttgacatgcc cccagtatcc gggctcagag attttgtggc agcataacga    420
```

```
taaaaatatc gggggcgatg aggacgacaa gaatatcggc tccgatgaag atcatctcag    480

tctgaaagaa ttttccgaat tggaacagag cggatattac gtatgttacc ctcgagggtc    540

taaacccgag gatgctaact tttaccttta tttgcgcgct agggtctgcg aaaactgcat    600

ggagatggat gtaatgtcag tggctacaat agtcatagtg gatatatgca ttaccggggg    660

actgttgctt ctcgtctatt actggtctaa aaaccgaaaa gctaaggcta agcccgttac    720

tcgaggagca ggcgctggtg ggcggcagag ggggcaaaat aaagagcgcc caccaccagt    780

gcctaatccg gattacgagc ccatacgcaa aggtcagcgg gatctctata gtgggcttaa    840

ccagcgaaga atctgagcgg ccgccttgac ttgcggccgg ccgcaactcc cacctgcaac    900

atgcgtgact gactgaggcc gcgactctag agtcgacctg cacgaggtta acgaattcta    960

ccgggtaggg gaggcgcttt tcccaaggca gtctggagca tgcgctttag cagccccgct   1020

gggcacttgg cgctacacaa gtggcctctg gcctcgcaca cattccacat ccaccggtag   1080

gcgccaaccg gctccgttct ttggtggccc cttcgcgcca ccttctactc ctcccctagt   1140

caggaagttc ccccccgccc cgcagctcgc gtcgtgcagg acgtgacaaa tggaagtagc   1200

acgtctcact agtctcgtgc agatggacag caccgctgag caatggaagc gggtaggcct   1260

ttggggcagc ggccaatagc agctttgctc cttcgctttc tgggctcaga ggctgggaag   1320

gggtgggtcc gggggcgggc tcaggggcgg ggcgggcgcc cgaaggtcct ccggaggccc   1380

ggcattctgc acgcttcaaa agcgcacgtc tgccgcgctg ttctcctctt cctcatctcc   1440

gggcctttcg acctgcagcc caagcttacc atgagcgagc tgattaagga gaacatgcac   1500

atgaagctgt acatggaggg caccgtggac aaccatcact tcaagtgcac atccgagggc   1560

gaaggcaagc cctacgaggg cacccagacc atgagaatca aggtggtcga gggcggccct   1620

ctcccottcg ccttcgacat cctggctact agcttcctct acggcagcaa gaccttcatc   1680

aaccacaccc agggcatccc cgacttcttc aagcagtcct tccctgaggg cttcacatgg   1740

gagagagtca ccacatacga agacgggggc gtgctgaccg ctacccagga caccagcctc   1800

caggacggct gcctcatcta caacgtcaag atcagagggg tgaacttcac atccaacggc   1860

cctgtgatgc agaagaaaac actcggctgg gaggccttca ccgagacgct gtaccccgct   1920

gacggcggcc tggaaggcag aaacgacatg gccctgaagc tcgtgggcgg gagccatctg   1980

atcgcaaaca tcaagaccac atatagatcc aagaaacccg ctaagaacct caagatgcct   2040

ggcgtctact atgtggacta cagactggaa agaatcaagg aggccaacaa cgagacctac   2100

gtcgagcagc acgaggtggc agtggccaga tactgcgacc tccctagcaa actggggcac   2160

aagcttaatt aa                                                       2172
```

<210> SEQ ID NO 6
<211> LENGTH: 8
<212> TYPE: DNA
<213> ORGANISM: Artificial Sequence
<220> FEATURE:
<223> OTHER INFORMATION: Synthetic Sequence (AP-1 Transcription factor binding motif)

<400> SEQUENCE: 6

```
ttgagtca                                                               8
```

<210> SEQ ID NO 7
<211> LENGTH: 85
<212> TYPE: DNA
<213> ORGANISM: Artificial Sequence
<220> FEATURE:
<223> OTHER INFORMATION: Synthetic Sequence (AP-1 Transcription factor
binding site)

<400> SEQUENCE: 7
ttgagtcaag attgagtcat cgttgagtca gacttgagtc actattgagt caactttgag 60
tcatgcttga gtcagtattg agtca 85

<210> SEQ ID NO 8
<211> LENGTH: 30
<212> TYPE: DNA
<213> ORGANISM: Artificial Sequence
<220> FEATURE:
<223> OTHER INFORMATION: Synthetic Sequence (NFAT Transcription factor
binding motif)

<400> SEQUENCE: 8
ggaggaaaaa ctgtttcata cagaaggcgt 30

<210> SEQ ID NO 9
<211> LENGTH: 180
<212> TYPE: DNA
<213> ORGANISM: Artificial Sequence
<220> FEATURE:
<223> OTHER INFORMATION: Synthetic Sequence (NFAT Transcription factor
binding site)

<400> SEQUENCE: 9
ggaggaaaaa ctgtttcata cagaaggcgt ggaggaaaaa ctgtttcata cagaaggcgt 60
ggaggaaaaa ctgtttcata cagaaggcgt ggaggaaaaa ctgtttcata cagaaggcgt 120
ggaggaaaaa ctgtttcata cagaaggcgt ggaggaaaaa ctgtttcata cagaaggcgt 180

<210> SEQ ID NO 10
<211> LENGTH: 9
<212> TYPE: DNA
<213> ORGANISM: Artificial Sequence
<220> FEATURE:
<223> OTHER INFORMATION: Synthetic Sequence (NR4A1 Transcription factor
binding motif)

<400> SEQUENCE: 10 aaaggtcac 9

<210> SEQ ID NO 11
<211> LENGTH: 93
<212> TYPE: DNA
<213> ORGANISM: Artificial Sequence
<220> FEATURE:
<223> OTHER INFORMATION: Synthetic Sequence (NR4A1 Transcription factor
binding site)

<400> SEQUENCE: 11
aaaggtcaca gaaaaggtca ctcgaaaggt cacgacaaag gtcacctaaa aggtcacact 60
aaaggtcact gcaaaggtca cgtaaaaggt cac 93

<210> SEQ ID NO 12
<211> LENGTH: 14
<212> TYPE: DNA
<213> ORGANISM: Artificial Sequence
<220> FEATURE:
<223> OTHER INFORMATION: Synthetic Sequence (NFkB Transcription factor
binding motif)

<400> SEQUENCE: 12

```
ggggaaattc ccct                                                    14


<210> SEQ ID NO 13
<211> LENGTH: 119
<212> TYPE: DNA
<213> ORGANISM: Artificial Sequence
<220> FEATURE:
<223> OTHER INFORMATION: Synthetic Sequence (NFkB Transcription factor
      binding site)

<400> SEQUENCE: 13

ggggaaattc ccctagaggg gaaattcccc ttcgggggaa attcccctga cggggaaatt     60

cccctctagg ggaaattccc ctactgggga aattcccctt gcggggaaat tcccctgta     119


<210> SEQ ID NO 14
<211> LENGTH: 20
<212> TYPE: RNA
<213> ORGANISM: Artificial Sequence
<220> FEATURE:
<223> OTHER INFORMATION: Synthetic Sequence (mouse CD3 zeta crRNA)

<400> SEQUENCE: 14

cuccugggaa ccgcacgugg                                              20


<210> SEQ ID NO 15
<211> LENGTH: 20
<212> TYPE: RNA
<213> ORGANISM: Artificial Sequence
<220> FEATURE:
<223> OTHER INFORMATION: Synthetic Sequence (human beta-2-microglobulin
      crRNA)

<400> SEQUENCE: 15

cgugaguaaa ccugaaucuu                                              20


<210> SEQ ID NO 16
<211> LENGTH: 20
<212> TYPE: RNA
<213> ORGANISM: Artificial Sequence
<220> FEATURE:
<223> OTHER INFORMATION: Synthetic Sequence (human CD3 epsilon crRNA)

<400> SEQUENCE: 16

agggcauguc aauauuacug                                              20


<210> SEQ ID NO 17
<211> LENGTH: 23
<212> TYPE: RNA
<213> ORGANISM: Artificial Sequence
<220> FEATURE:
<223> OTHER INFORMATION: Synthetic Sequence (human CD3 gamma crRNA)

<400> SEQUENCE: 17

guaaugccaa ggacccucga ggg                                          23


<210> SEQ ID NO 18
<211> LENGTH: 20
<212> TYPE: RNA
<213> ORGANISM: Artificial Sequence
<220> FEATURE:
<223> OTHER INFORMATION: Synthetic Sequence (human CD3 delta crRNA)

<400> SEQUENCE: 18

ccccuucaag auaccuauag                                              20
```

<210> SEQ ID NO 19
<211> LENGTH: 20
<212> TYPE: RNA
<213> ORGANISM: Artificial Sequence
<220> FEATURE:
<223> OTHER INFORMATION: Synthetic Sequence (human CD3 zeta crRNA)

<400> SEQUENCE: 19
gauggaaucc ucuucaucua 20

<210> SEQ ID NO 20
<211> LENGTH: 20
<212> TYPE: RNA
<213> ORGANISM: Artificial Sequence
<220> FEATURE:
<223> OTHER INFORMATION: Synthetic Sequence (human CD8 alpha crRNA)

<400> SEQUENCE: 20
gcugcugucc aacccgacgu 20

<210> SEQ ID NO 21
<211> LENGTH: 20
<212> TYPE: RNA
<213> ORGANISM: Artificial Sequence
<220> FEATURE:
<223> OTHER INFORMATION: Synthetic Sequence (human Her2/ERBB2 crRNA)

<400> SEQUENCE: 21
caacuaccuu ucuacggacg 20

<210> SEQ ID NO 22
<211> LENGTH: 1524
<212> TYPE: DNA
<213> ORGANISM: Artificial Sequence
<220> FEATURE:
<223> OTHER INFORMATION: Synthetic Sequence (human Her2-specific second-generation CAR)

<400> SEQUENCE: 22
atggattttc aggtgcagat tttcagcttc ctgctaatca gtgcctcagt cataatgtcc 60
agaggagata tccagatgac ccagtccccg agctccctgt ccgcctctgt gggcgatagg 120
gtcaccatca cctgccgtgc cagtcaggat gtgaatactg ctgtagcctg gtatcaacag 180
aaaccaggaa aagctccgaa actactgatt tactcggcat ccttccttta ttctggagtc 240
ccttctcgct tctctggatc tagatctggg acggatttca ctctgaccat cagcagtctg 300
cagccggaag acttcgcaac ttattactgt cagcaacatt atactactcc tcccacgttc 360
ggacagggta ccaaggtgga gatcaaacgc actgggtcta catctggatc tgggaagccg 420
ggttctggtg agggttctga ggttcagctg gtggagtctg gcggtggcct ggtgcagcca 480
gggggctcac tccgtttgtc ctgtgcagct tctggcttca acattaaaga cacctatata 540
cactgggtgc gtcaggcccc gggtaagggc ctggaatggg ttgcaaggat ttatcctacg 600
aatggttata ctagatatgc cgatagcgtc aagggccgtt tcactataag cgcagacaca 660
tccaaaaaca cagcctacct gcagatgaac agcctgcgtg ctgaggacac tgccgtctat 720
tattgttcta gatggggagg ggacggcttc tatgctatgg acgtgtgggg tcaaggaacc 780
ctggtcaccg tctcctcggc ggccgcattc gtgccggtct tcctgccagc gaagcccacc 840
acgacgccag cgccgcgacc accaacaccg gcgcccacca tcgcgtcgca gcccctgtcc 900
ctgcgcccag aggcgtgccg gccagcagca ggaggagcag tgcacacgag ggggctggac 960
ttcgcctgtg atatctacat ctgggcgccc ttggccggga cttgtggggt ccttctcctg 1020

```
tcactggtta tcaccctttta ctgcaaccac aggaacaaac ggggcagaaa gaagctcctg   1080

tatatattca aacaaccatt tatgagacca gtacaaacta ctcaagagga agatggctgt   1140

agctgccgat ttccagaaga agaagaagga ggatgtgaac tgagagtgaa gttcagcagg   1200

agcgcagacg cccccgcgta ccagcagggc cagaaccagc tctataacga gctcaatcta   1260

ggacgaagag aggagtacga tgttttggac aagagacgtg gccgggaccc tgagatgggg   1320

ggaaagccgc agagaaggaa gaaccctcag gaaggcctgt acaatgaact gcagaaagat   1380

aagatggcgg aggcctacag tgagattggg atgaaaggcg agcgccggag gggcaagggg   1440

cacgatggcc tttaccaggg tctcagtaca gccaccaagg acacctacga cgcccttcac   1500

atgcaggccc tgccccctcg ctaa                                            1524
```

<210> SEQ ID NO 23
<211> LENGTH: 2178
<212> TYPE: DNA
<213> ORGANISM: Artificial Sequence
<220> FEATURE:
<223> OTHER INFORMATION: Synthetic Sequence (4xNFAT-CD3-PKG-BFP cassette)

<400> SEQUENCE: 23

```
agactgccgg atccaagctg gaggaaaaac tgtttcatac agaaggcgtg gaggaaaaac     60

tgtttcatac agaaggcgtg gaggaaaaac tgtttcatac agaaggcgtg gaggaaaaac    120

tgtttcatac agaaggcgtc gcgaattcgc ggagactcta gagggtatat aatggaagct    180

cgatttccag cttggcattc cggtactgtt ggtaaacacc aagcttcata tggccaccat    240

gcagagtggg actcattgga gagttttggg cctgtgcctt ctctcagttg gcgtctgggg    300

gcaggatgga aacgaggaaa tgggaggtat aacgcaaaca ccctacaaag tctcaatatc    360

cggaacgacg gttattttga catgccccca gtatccgggc tcagagattt tgtggcagca    420

taacgataaa aatatcgggg gcgatgagga cgacaagaat atcggctccg atgaagatca    480

tctcagtctg aaagaatttt ccgaattgga acagagcgga tattacgtat gttaccctcg    540

agggtctaaa cccgaggatg ctaactttta cctttatttg cgcgctaggg tctgcgaaaa    600

ctgcatggag atggatgtaa tgtcagtggc tacaatagtc atagtggata tatgcattac    660

cgggggactg ttgcttctcg tctattactg gtctaaaaac cgaaaagcta aggctaagcc    720

cgttactcga ggagcaggcg ctggtgggcg gcagaggggg caaaataaag agcgcccacc    780

accagtgcct aatccggatt acgagcccat acgcaaaggt cagcgggatc tctatagtgg    840

gcttaaccag cgaagaatct gagcggccgc cttgacttgc ggccggccgc aactcccacc    900

tgcaacatgc gtgactgact gaggccgcga ctctagagtc gacctgcacg aggttaacga    960

attctaccgg gtaggggagg cgcttttccc aaggcagtct ggagcatgcg ctttagcagc   1020

cccgctgggc acttggcgct acacaagtgg cctctggcct cgcacacatt ccacatccac   1080

cggtaggcgc caaccggctc cgttctttgg tggccccttc gcgccacctt ctactcctcc   1140

cctagtcagg aagttccccc ccgccccgca gctcgcgtcg tgcaggacgt gacaaatgga   1200

agtagcacgt ctcactagtc tcgtgcagat ggacagcacc gctgagcaat ggaagcgggt   1260

aggcctttgg ggcagcggcc aatagcagct ttgctccttc gctttctggg ctcagaggct   1320

gggaaggggt gggtccgggg gcgggctcag gggcggggcg ggcgcccgaa ggtcctccgg   1380

aggcccggca ttctgcacgc ttcaaaagcg cacgtctgcc gcgctgttct cctcttcctc   1440

atctccgggc ctttcgacct gcagcccaag cttaccatga gcgagctgat taaggagaac   1500
```

-continued

```
atgcacatga agctgtacat ggagggcacc gtggacaacc atcacttcaa gtgcacatcc   1560

gagggcgaag gcaagcccta cgagggcacc cagaccatga gaatcaaggt ggtcgagggc   1620

ggccctctcc ccttcgcctt cgacatcctg gctactagct tcctctacgg cagcaagacc   1680

ttcatcaacc acacccaggg catccccgac ttcttcaagc agtccttccc tgagggcttc   1740

acatgggaga gagtcaccac atacgaagac gggggcgtgc tgaccgctac ccaggacacc   1800

agcctccagg acggctgcct catctacaac gtcaagatca gaggggtgaa cttcacatcc   1860

aacggccctg tgatgcagaa gaaaacactc ggctgggagg ccttcaccga gacgctgtac   1920

cccgctgacg gcggcctgga aggcagaaac gacatggccc tgaagctcgt gggcgggagc   1980

catctgatcg caaacatcaa gaccacatat agatccaaga aacccgctaa gaacctcaag   2040

atgcctggcg tctactatgt ggactacaga ctggaaagaa tcaaggaggc caacaacgag   2100

acctacgtcg agcagcacga ggtggcagtg gccagatact gcgacctccc tagcaaactg   2160

gggcacaagc ttaattaa                                                 2178
```